(12) United States Patent
Bathe et al.

(10) Patent No.: US 8,542,898 B2
(45) Date of Patent: Sep. 24, 2013

(54) BAYESIAN INFERENCE OF PARTICLE MOTION AND DYNAMICS FROM SINGLE PARTICLE TRACKING AND FLUORESCENCE CORRELATION SPECTROSCOPY

(75) Inventors: Mark Bathe, Cambridge, MA (US); Jun He, San Diego, CA (US); Syuan-Ming Guo, Cambridge, MA (US); Nilah Monnier, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 97 days.

(21) Appl. No.: 13/328,879

(22) Filed: Dec. 16, 2011

(65) Prior Publication Data
US 2012/0155725 A1  Jun. 21, 2012

Related U.S. Application Data

(60) Provisional application No. 61/423,863, filed on Dec. 16, 2010.

(51) Int. Cl.
*G06K 9/00* (2006.01)
(52) U.S. Cl.
USPC .......................................... 382/128; 703/11
(58) Field of Classification Search
USPC ....................................................... 382/128
See application file for complete search history.

(56) References Cited

U.S. PATENT DOCUMENTS 6,219,440 B1 * 4/2001 Schaff et al. .................. 382/128
2009/0226521 A1 * 9/2009 Smyth et al. .................. 424/484
2011/0073531 A1 * 3/2011 Mezic et al. ............... 209/127.1

OTHER PUBLICATIONS

Mark A. Beaumont and Bruce Rannald, "The Bayesian Revolution in Genetics", "Nature Reviews: Genetics", 2004, pp. 251-261, vol. 5, Publisher: Nature, Published in: www.nature.com/reviews/genetics.
J. Bronson, J. Fei, et al., "Learning Rates and States from Biophysical Time Series: A Bayesian Approach to Model Selection and Single-Molecule FRET ", "Biophysical Journal", Dec. 2009, pp. 3196-3205, vol. 97, No. 12, Publisher: Cell Press, Published in: http://www.sciencedirect.com/science/article/pii/S0006349509015136.
D. Frenkel and B. Smit, "Understanding Molecular Simulation: From Algorithms to Applications", 2002, pp. 525-532, Publisher: Academic Press, Published in: San Diego, Calif.

(Continued)

*Primary Examiner* — Samir Ahmed
*Assistant Examiner* — Totam Le
(74) *Attorney, Agent, or Firm* — Evans & Molinelli PLLC; Eugene J. Molinelli

(57) ABSTRACT

Techniques for inferring particle dynamics from certain data include determining multiple models for motion of particles in a biological sample. Each model includes a corresponding set of one or more parameters. Measured data is obtained based on measurements at one or more voxels of an imaging system sensitive to motion of particles in the biological sample; and, determining noise correlation of the measured data. Based at least in part on the noise correlation, a marginal likelihood is determined of the measured data given each model of the multiple models. A relative probability for each model is determined based on the marginal likelihood. Based at least in part on the relative probability for each model, a value is determined for at least one parameter of the set of one or more parameters corresponding to a selected model of the multiple models.

23 Claims, 36 Drawing Sheets

(56) References Cited

OTHER PUBLICATIONS

Nir Friedman et al., "Using Bayesian Networks to Analyze Expression Data", "Journal of Computational Biology", 2000, pp. 601-620, vol. 7, No. 3/4, Publisher: Mary Ann Liebert Inc., Published in: http://online.liebertpub.com/doi/pdfplus/10.1089/106652700750050961.

Nir Friedman, "Inferring Cellular Networks Using Probabilistic Graphical Models", "Sceince", 2004, pp. 799-805, vol. 303, No. 799, Publisher: AAAS, Published in: http://www.sciencemag.org/content/303/5659/799.full.html.

Nir Friedman et al., "Linking Stochastic Dynamics to Population Distribution: An Analytical Framework of Gene Expression", "Physical Review Letters", Oct. 20, 2006, pp. 168302-1-168302-4, vol. 97, No. 16, Publisher: American Physical Society, Published in: http://prl.aps.org/toc/PRL/v97/i16.

Khuloud Jaqaman and Gaudenz Danuser, "Linking Data to Models: Data Regression", "Nature Reviews: Molecular Cell Biology", 2006, pp. 813-819, vol. 7, No. 11, Publisher: Nature Publishing Group, Published in: http://www.nature.com/nrm/journal/v7/n11/pdf/nrm2030.pdf.

Hong Qian et al., "Single particle tracking: Analysis of diffusion and flow in two-dimensional systems", "Biophysical Journal", 1991, pp. 910-921, vol. 60, No. 10, Publisher: Biophysical Society, Published in: http://ac.els-cdn.com/S0006349591821257/1-s2.0-S0006349591821257-main.pdf?_tid=84860a6ba0b381f711b860bd21fefa4e&acdnat=1333991135_aeca0807f439430ac2fd.

Karen Sachs et al., "Causal Protein-Signaling Networks Derived from Multiparameter Single-Cell Data", "Science", 2005, pp. 532-529, vol. 308, Publisher: AAAS, Published in: www.sciencemag.org/cgi/content/full/308/5721/523/.

Karen Sachs et al., "Learning Signaling Network Structures with Sparsely Distributed Data", "Journal of Computational Biology", 2009, pp. 201-212, vol. 16, No. 2, Publisher: Mary Ann Liebert Inc., Published in: http://online.liebertpub.com/doi/pdfplus/10.1089/cmb.2008.07TT.

Michael J. Saxton and Ken Jacobson, "Single-Particle Tracking: Applications to Membrane Dynamics", "Annual Review of Biophysics and Biomolecular Structure", 1997, pp. 373-399, vol. 26, Publisher: Annual Reviews Inc., Published in: www.annualreviews.org.

\* cited by examiner

TRAJECTORIES

MSD CURVES

MEAN MSD

NOISE COVARIANCE

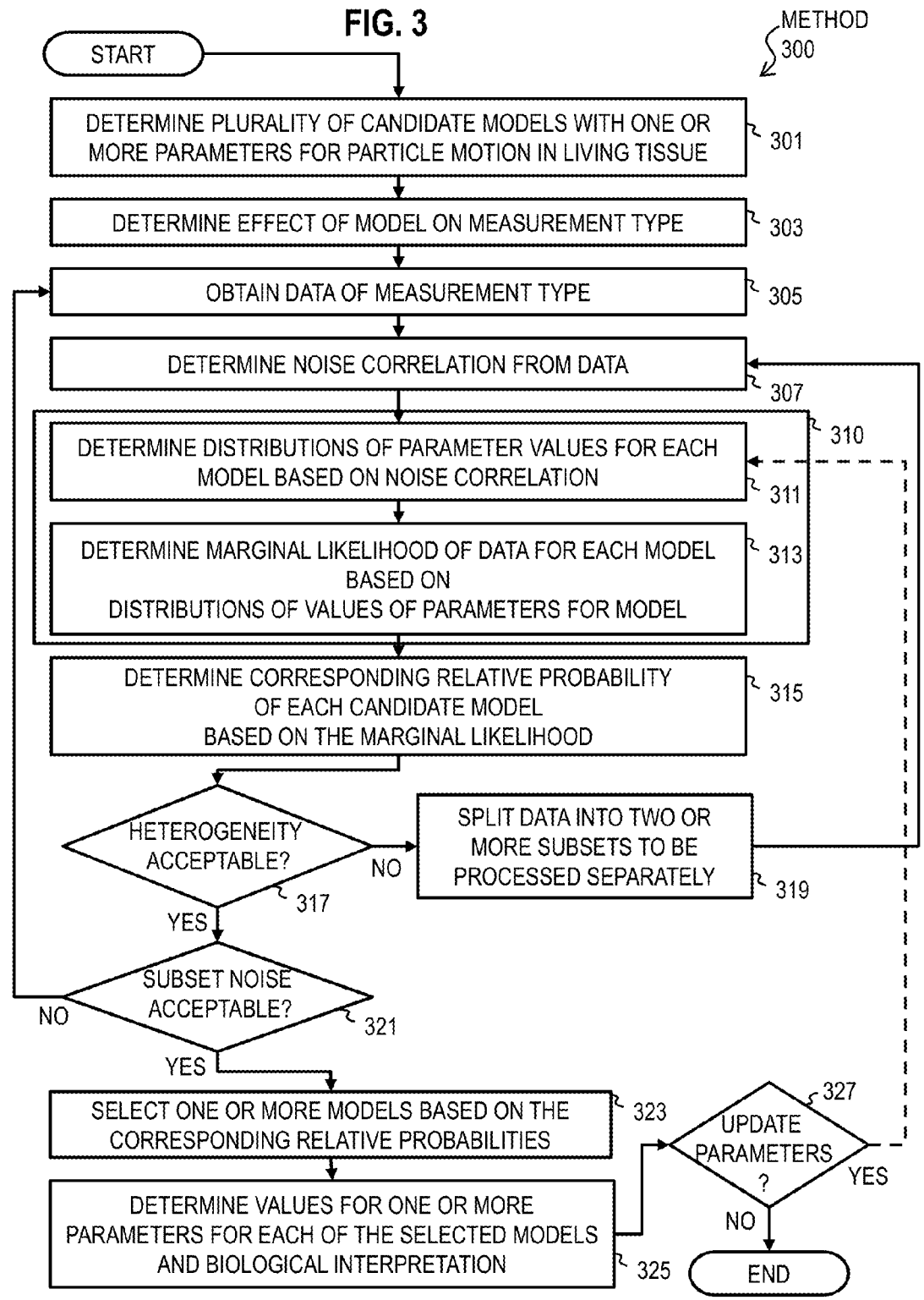

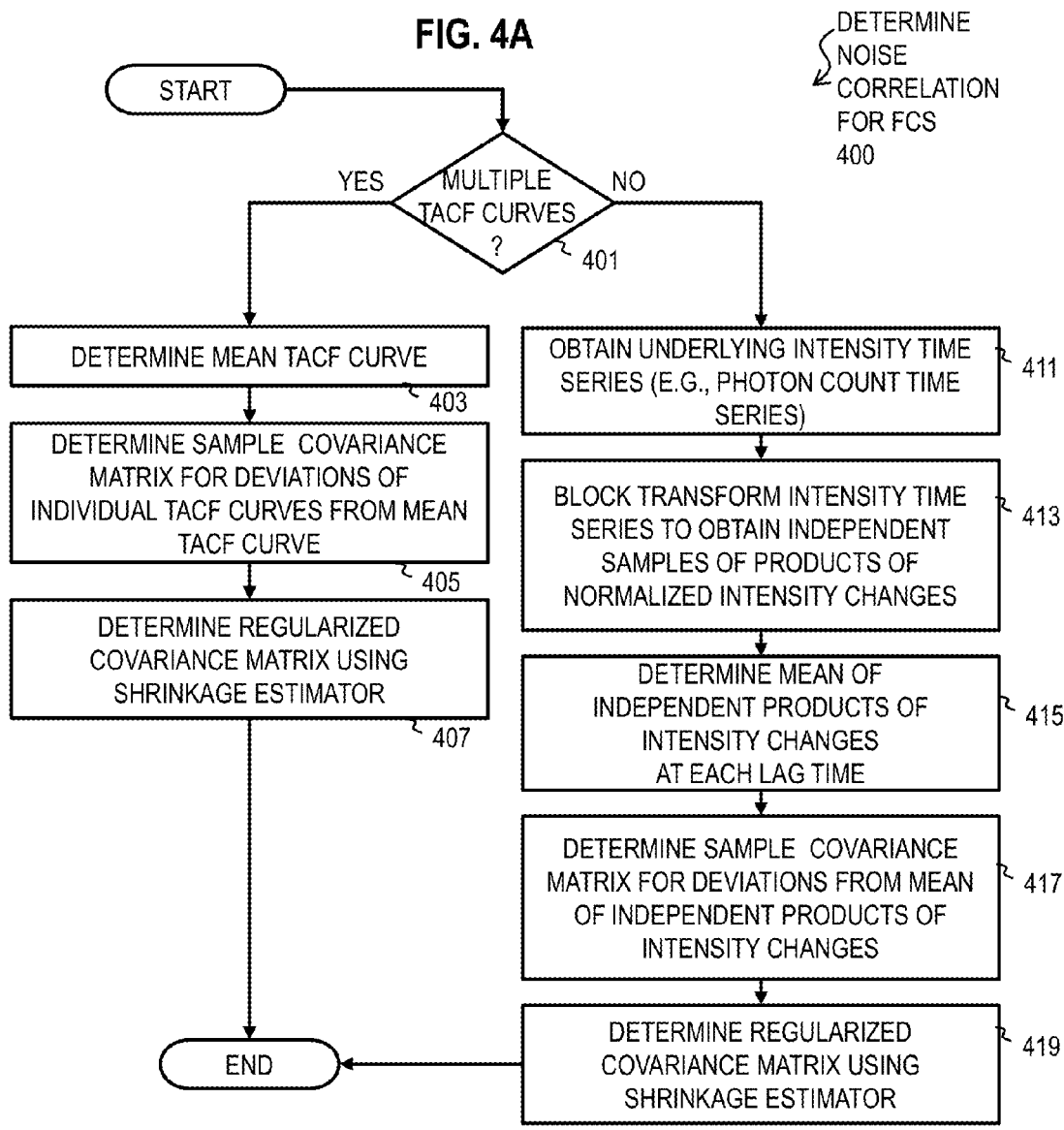

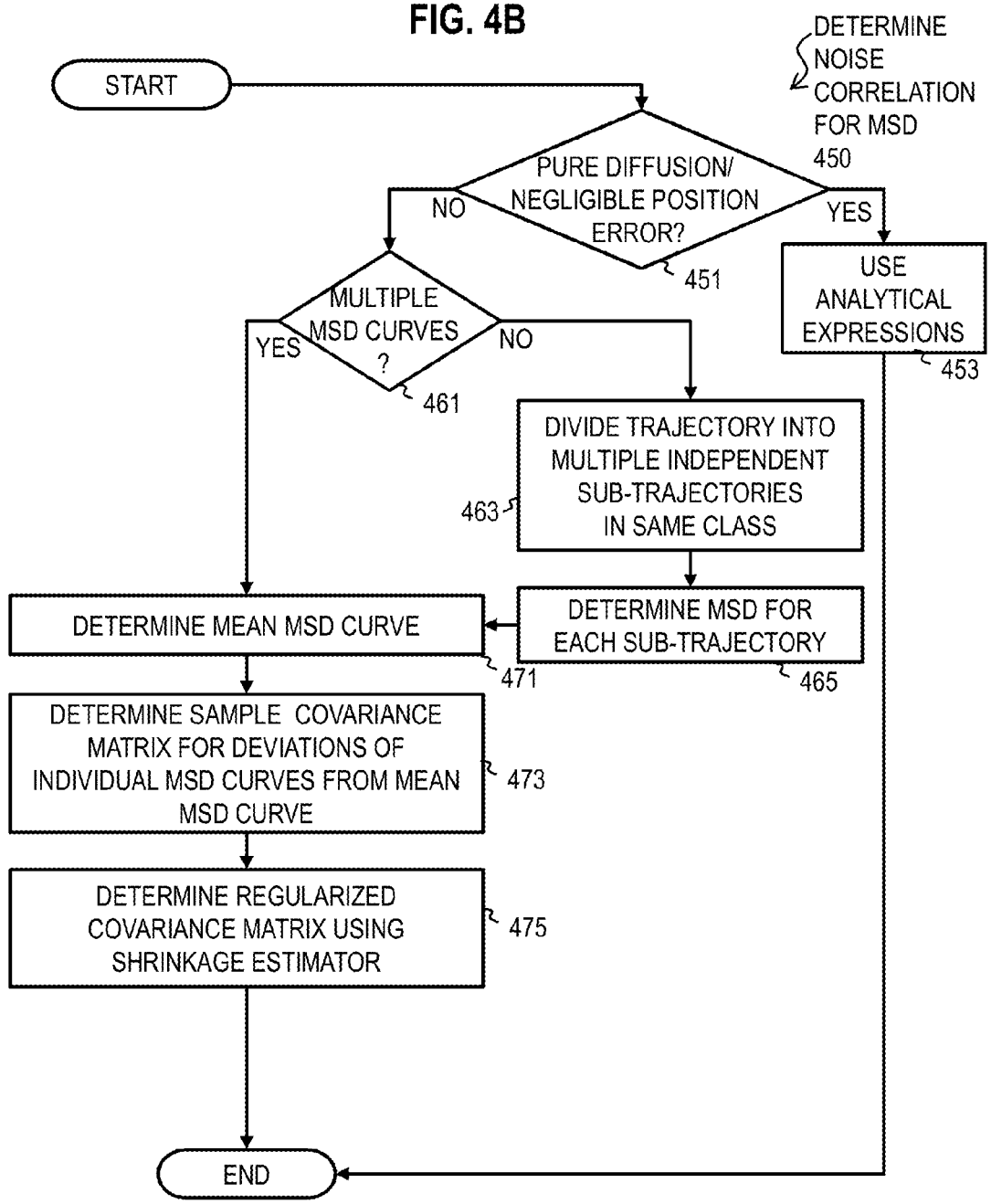

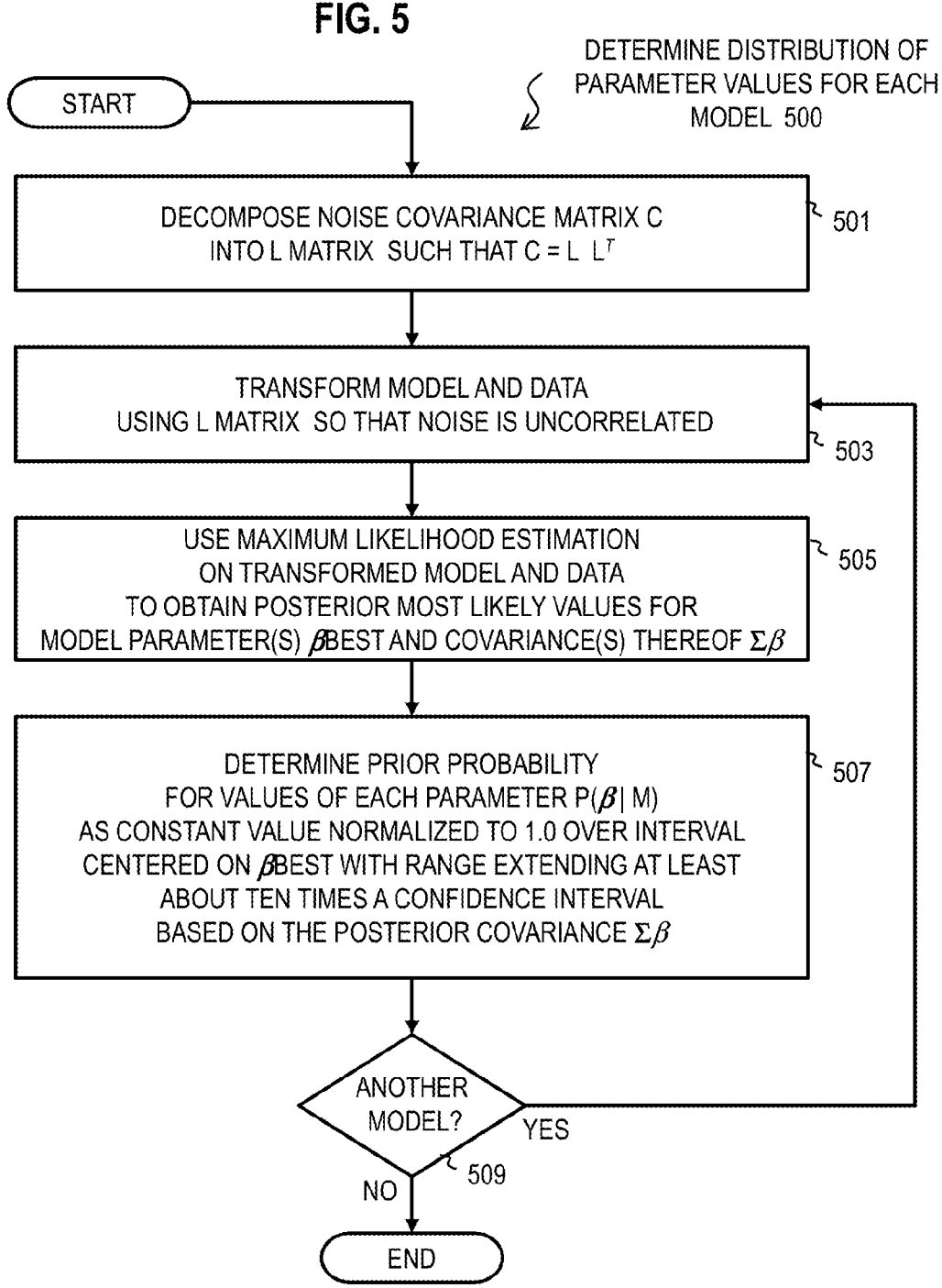

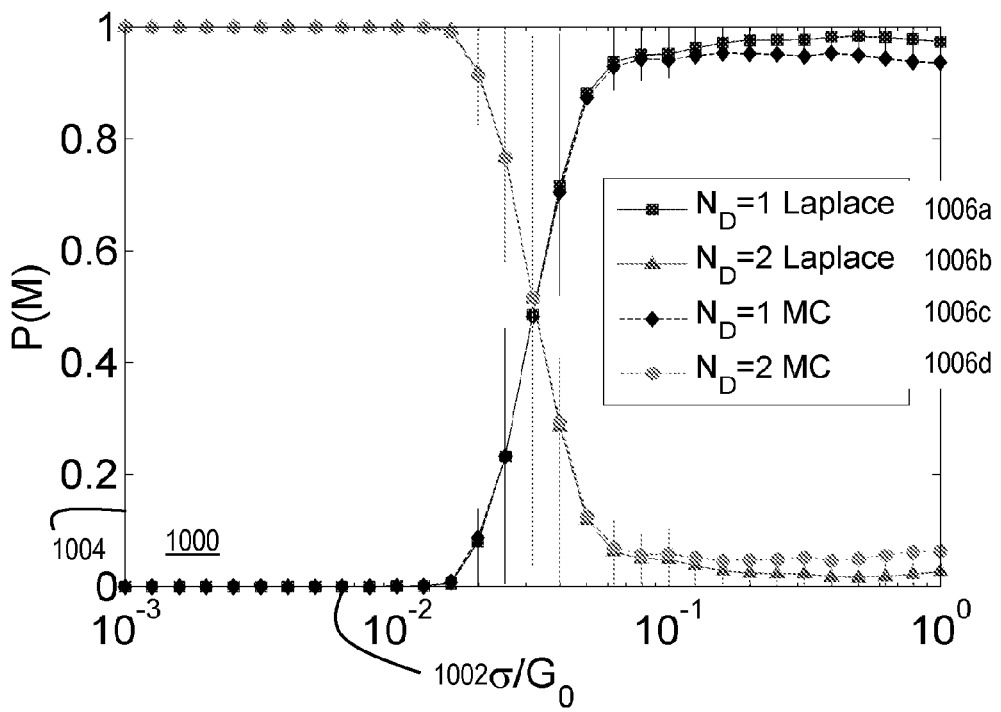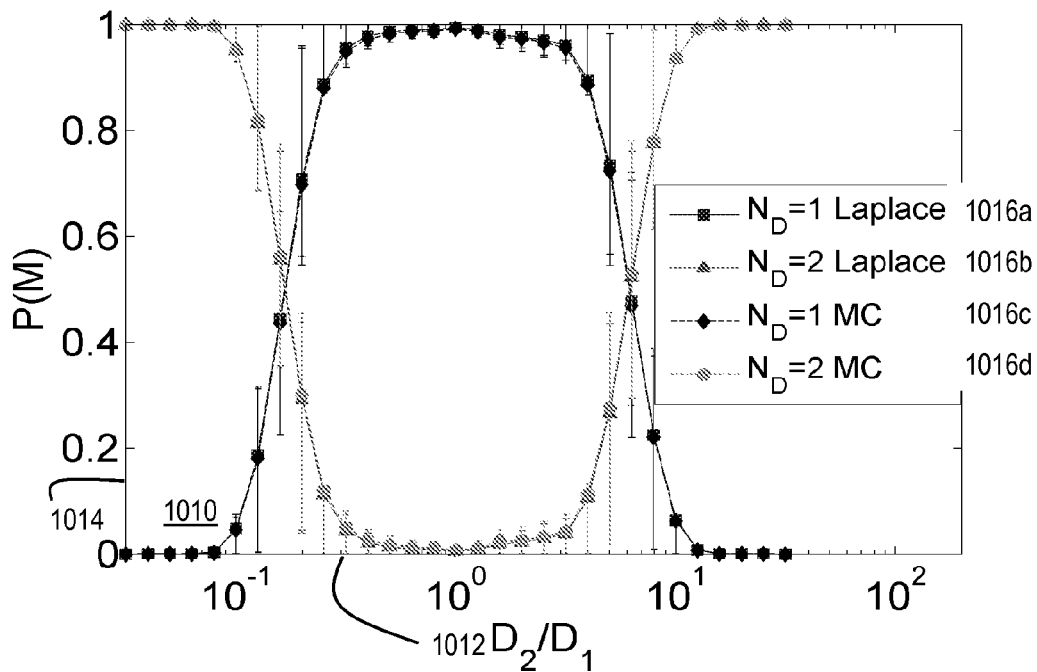

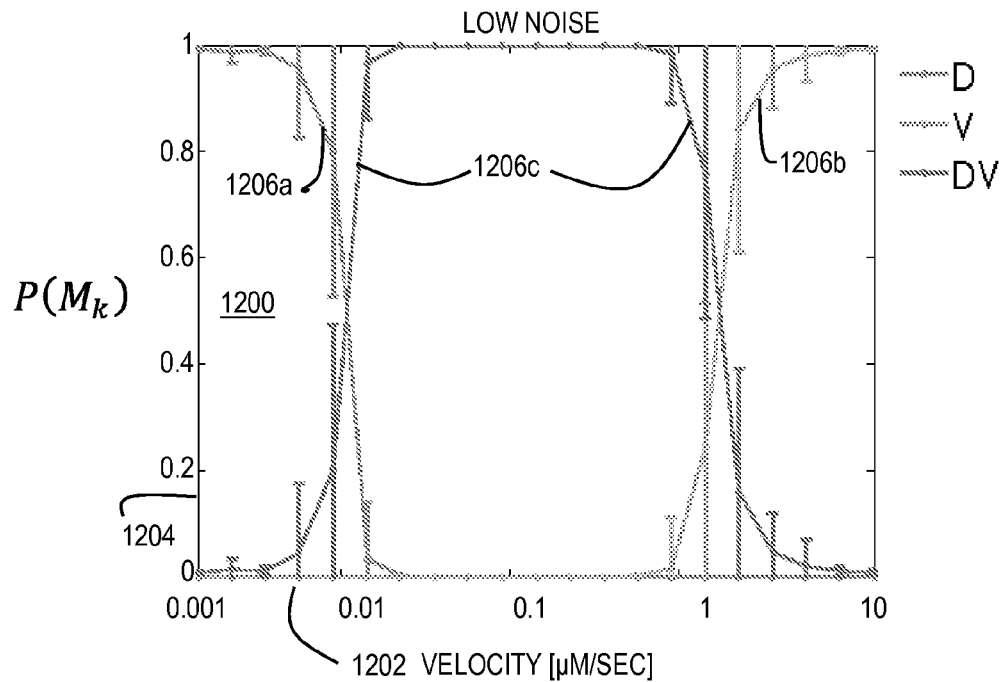
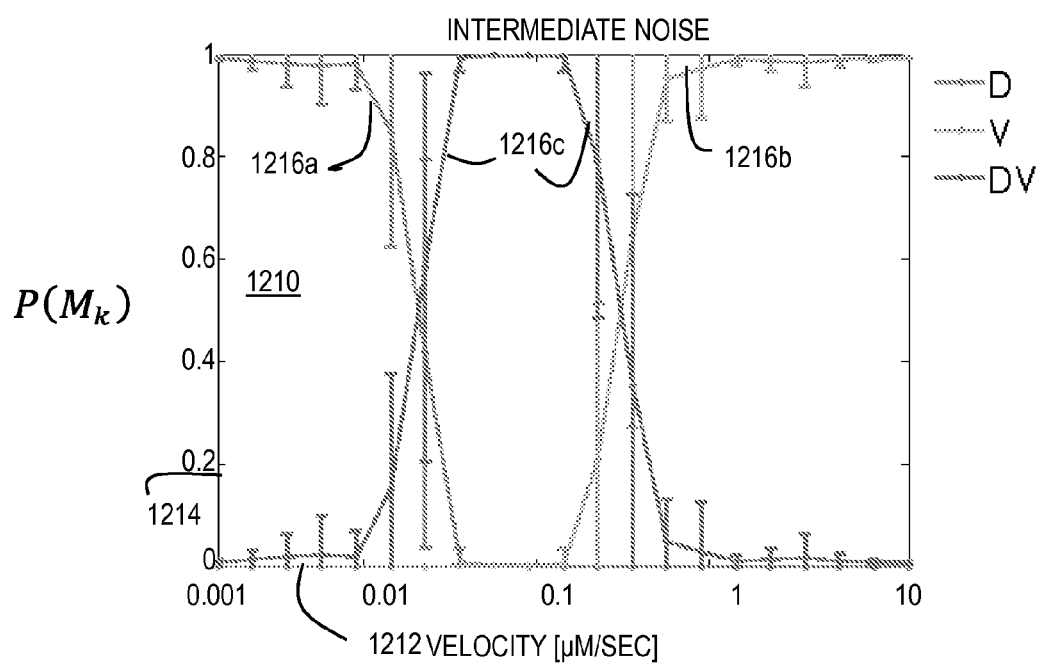

HIGH NOISE

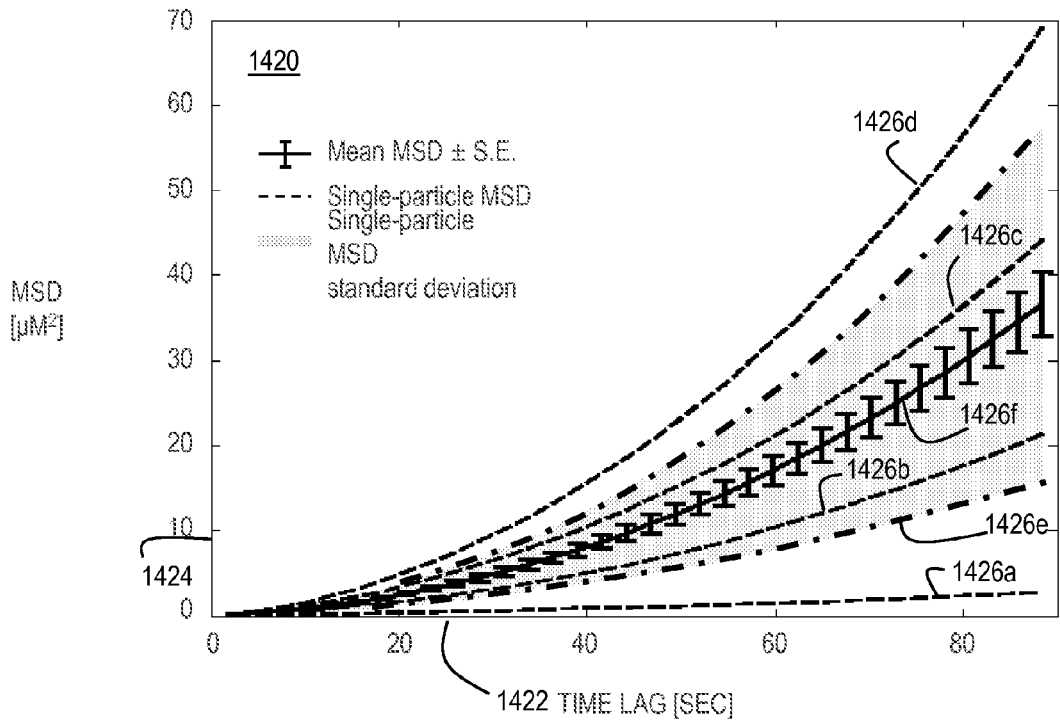
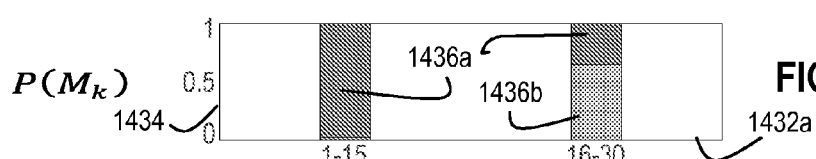
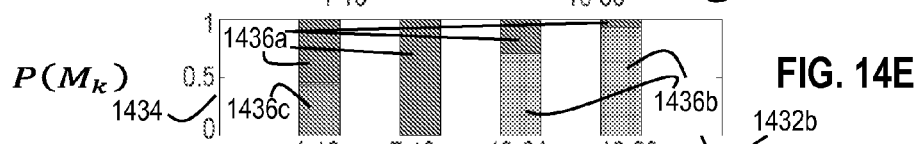
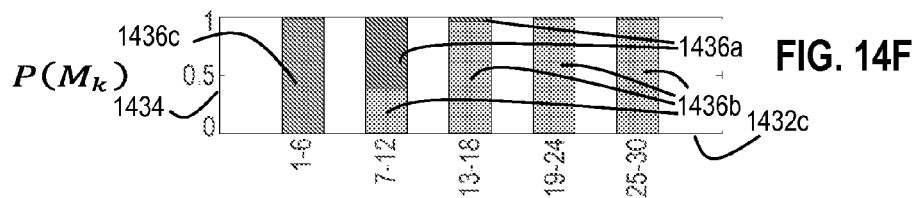

KINETOCHORE TRAJECTORIES DURING MOUSE OOCYTE MEIOSIS I

BAYESIAN INFERENCE OF PARTICLE MOTION AND DYNAMICS FROM SINGLE PARTICLE TRACKING AND FLUORESCENCE CORRELATION SPECTROSCOPY

CROSS-REFERENCE TO RELATED APPLICATIONS

This application claims benefit of Provisional Appln. 61/423,863, filed Dec. 16, 2010, the entire contents of which are hereby incorporated by reference as if fully set forth herein, under 35 U.S.C. §119(e).

BACKGROUND OF THE INVENTION

Physical processes inside a living cell or tissue, including binding and transport, are of interest in understanding and controlling cell functions, such as protein transport and signaling, energy generation and utilization, differentiation, growth, replication and apoptosis. These functions are important to the detection and treatment of disease, such as cancer. Modern techniques for measuring and monitoring temporal fluctuations in fluorescent particle spatial distributions and single particle trajectories (SPT) provide data to elucidate those physical processes.

Classical fluorescence correlation spectroscopy (FCS) measures fluctuations in fluorescence intensity in a small detection volume to infer molecular properties from governing continuum reaction-diffusion-convection equations, for example. Whereas classical FCS is performed at a single point with a photomultiplier tube (PMT) or Avalanche Photodiode (APD), the relatively recent advent of laser-scanning microscopy and electron multiplying charge coupled device (EM-CCD) cameras has enabled spatially-resolved FCS to be performed in living cells and tissues using confocal microscopy, thus providing a rich source of spatiotemporal information upon which to base biophysical models of biomolecular dynamics Quantitative measurement and tracking of the trajectories of single particles in living cells and tissues is increasingly common and provides a rich source of information about the physical environments and modes of transport of biological structures. A common metric for inferring the physical mode of particle motion is the mean-squared displacement (MSD) of the particle over time, which takes distinct functional forms depending on the type of motion that generated the trajectory.

SUMMARY OF THE INVENTION

Data from such techniques have the potential to be used to distinguish competing hypothesized models of particle motion and transport inside a cell. However, interpretations of FCS data and single particle trajectory (SPT) for one or more MSD curves are nontrivial due to the limits of measurement resolutions and the presence of noise. Here are presented techniques to utilize Bayesian inference to analyze data sensitive to motion of particles such as fluorescent particles including proteins, DNA, and other small molecules in order to determine the most probable mechanisms of particle motion in the context of living cells or tissues as well as extracts thereof, collectively termed biological samples herein. As used herein, living tissue refers to one or more living cells or intercellular structures or some combination thereof. A voxel refers to a volume element in an imaging system that measures a physical property, such as light absorption or light emissions at each of one or more wavelengths. As used herein, an imaging system measures a physical property at one or more voxels.

In a first set of embodiments, a method comprises determining multiple models for motion of particles in a biological sample. Each model includes a corresponding set of one or more parameters. The method also includes obtaining measured data based on measurements at one or more voxels of an imaging system sensitive to motion of particles in the biological sample; and, determining noise correlation of the measured data. The method also includes determining, based at least in part on the noise correlation, a marginal likelihood of the measured data for each model of the multiple models. The method further includes determining a relative probability for each model of the multiple models based on the marginal likelihood. The method still further includes determining, based at least in part on the relative probability for each model, a value for a parameter of the set of one or more parameters corresponding to a selected model of the multiple models.

In other sets of embodiments, a computer-readable medium or apparatus performs one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3 is a flow diagram that illustrates an example method for determining relative probability of models for particle motion in biological sample and corresponding values of model parameters, according to an embodiment;

FIG. 4A and FIG. 4B are flow diagrams for different data type that each illustrates an example method for performing a step in FIG. 3, which determines noise correlation, according to an embodiment;

FIG. 5 is a flow diagram that illustrates an example method for performing a step in FIG. 3, which determines distribution of values for one or more parameters of a model, according to an embodiment;

FIG. 10A and FIG. 10B are graphs that illustrate an example dependence on the method of integration for the marginal probability, according to various embodiments;

FIG. 12A through FIG. 12D are graphs that illustrate an example effect of noise on analysis of simulated SPT data, according to an embodiment;

FIG. 14C through FIG. 14G are graphs that illustrate an example effect of heterogeneity on analysis of chromosome MSD data, according to an embodiment;

DETAILED DESCRIPTION

Figure 1A:
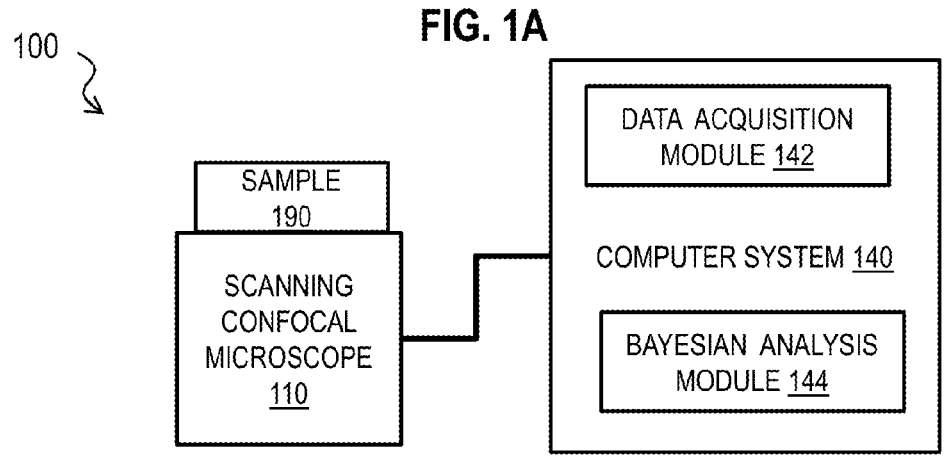
FIG. 1A is a block diagram that illustrates an example experimental setup to obtain measured data, according to an embodiment.

A method and apparatus are described for Bayesian analysis to determine parameters of particle motion in a biological sample. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. Several references are cited herein, and are hereby incorporated by reference as if fully set forth herein, except as the terminology is inconsistent with the terminology used herein.

Some embodiments of the invention are described below in the context of fluorescence correlation spectroscopy (FCS) data and mean square displacement (MSD) data. However, the invention is not limited to these contexts, but can be applied to any data sensitive to particle motion in a biological sample. For example, in other embodiments, these techniques are applied to image correlation spectroscopy (ICS) data, such as temporal image correlation spectroscopy (TICS) and spatial temporal image correlation spectroscopy (STICS0 which both tend to experience correlated noise.

As stated above, interpretations of FCS data and MSD curves are nontrivial due to limitations in measurement resolutions and the presence of noise. While the choice of a model representing a physical process may be unambiguous for certain cases such as free molecular diffusion or convective transport in homogeneous solutions, the correct choice of model becomes considerably more ambiguous in complex biological processes in living cells or extracellular matrices. Indeed, such processes may be governed by a combination of physical processes that is unknown a priori, and inference of molecular properties such as diffusion coefficients, rates of transport, or association-dissociation kinetics from a single assumed model may lead to erroneous results. The problem of complexity is made worse by the fact that measurements obtained from living cells often suffer from low signal-to-noise ratios and limited temporal sampling rate and total time. With such data, even fitting the correct model to the data can derive erroneous values for one or more model constants (called parameters, herein). For these reasons, an objective and unbiased approach to model evaluation in the analysis of FCS and MDS data is of interest. Bayesian inference provides one such framework. The work here adapts the processing of the types of data sensitive to particle motion in a biological sample to be effectively used with Bayesian analysis so as to yield useful descriptions of the movement of particles, such as probes and drug delivery nanoparticles and large molecules like proteins, peptides, deoxyribonucleic acid (DNA) and ribonucleic acid (RNA), and large objects such as organelles or cells.

Traditional analysis of FCS data typically involves the use of maximum likelihood estimation (MLE) to fit one or more models to measured temporal autocorrelation functions (TACF), and reduced chi-squared values to select the best fitting model. While useful for obtaining parameter estimates and uncertainties for a given model at the point estimate provided by least-squares fitting, MLE tends to favor complex models that over-fit measured data because the reduced chi-squared approach does not penalize model complexity appropriately. Thus model parameter values may be meaningless as they are used to fit noise. Moreover, MLE does not allow for the direct ranking of multiple competing models by their relative probabilities, supporting only pair-wise comparisons of nested models, where the simpler model provides the null hypothesis and a standard chi-squared test is performed.

Analytical forms for the dependence of MSD on temporal lag are known for many common modes of motion, so the observed MSD curve may in principle be used to infer both the mode of motion as well as the relevant parameter values, such as the diffusion coefficient, anomalous exponent, confinement radius, or speed of advection. In most biological applications, however, the underlying mode of motion is unknown a priori. Furthermore, experimental limitations (sampling rate and number and length of trajectories) and heterogeneity between the motions of different particles in a biological dataset can increase noise in the observed MSD curve, confounding objective analysis of single particle trajectories (SPTs). Strong correlations intrinsic to MSD curves further complicate the analysis process.

Successfully adapting Bayesian analysis to these types of data, at least, is shown herein to provide the advantages of Bayesian analysis, such as selecting the simplest hypothesis that describes the data based on the quality of the evidence for the data and the complexities of the competing models, naturally satisfying Okham's razor.

1. Overview

Approaches are developed for estimating the noise in data types sensitive to particle motion in a biological sample, which is a crucial step in the unbiased evaluation of competing models, and for developing useful approximations that render Bayesian analysis practical for deciphering particle motion in living tissue. The data types described herein include fluorescence correlation spectroscopy (FCS) data and mean square displacement (MSD) data, both well known in the art. FCS is based on measurements of fluorescent emission intensity time series, such as photon arrival time data or photon counts per time increment, detected in each of one or more femtoliter volumes (1 femtoliter, fl,=$10^{-15}$ liters). This kind of resolution is provided by confocal microscopy. MSD data is based on measurements of single particle trajectories (SPTs) as a few fluorescently-labeled particles move in time from one voxel to another of a multi-voxel imaging system, like a scanning confocal microscope.

FIG. 1A is a block diagram that illustrates an example experimental setup 100 to obtain measured data, according to an embodiment. The setup includes a biological sample 190, such as a glass slide on which is fixed one or more cells of living tissue. The sample 190 is disposed in a viewing port of a confocal microscope, such as scanning confocal microscope 110. The confocal microscope is connected to a computer system of one or more computers or chip sets, as described below with reference to FIG. 18 and FIG. 19, which control the operation of the microscope. The computer system 140 includes a module of hardware or software or some combination controlling the microscope (not shown) as well as a data acquisition module 142 of hardware or software or some combination to acquire, condition and store data from the microscope. In the illustrated embodiment, the computer system 140 includes a Bayesian analysis module 144 of hardware or software or some combination to implement one or more steps of the methods described below.

A confocal microscope, as is well known, is capable of focusing excitation illumination onto a small volume of the sample and focusing a detector of light emissions in the same volume (hence the name "confocal"). For example, both a laser light source and a detector use light passed through a common pinhole. This procedure reduces the confounding effects of light scattered into the detector from surrounding volumes. The light emission detected in the volume constitutes the data represented by one volume element (voxel) of the microscope system. Any detector can be used. In various embodiments, a sensitive photon counting device such as a Photomultiplier Tube (PMT) or Avalanche Photodiode (APD) is used. Both position and depth of the voxel in the sample can be controlled with precision on the order of a micron (1 micron, also called a micrometer, µm,=$10^{-6}$ meters). A scanning confocal microscope, such as microscope 110, rapidly moves the voxel through the sample 190, e.g., using a spinning disk with multiple pinholes. In various embodiments, any confocal microscope known in the art may be used.

Although processes, equipment, and data structures are depicted in FIG. 1A as integral blocks in a particular arrangement for purposes of illustration, in other embodiments one or more processes or data structures, or portions thereof, are arranged in a different manner, on the same or different equipment, in one or more databases, or are omitted, or one or more different processes or data structures are included on the same or different equipment.

Figure 1B:
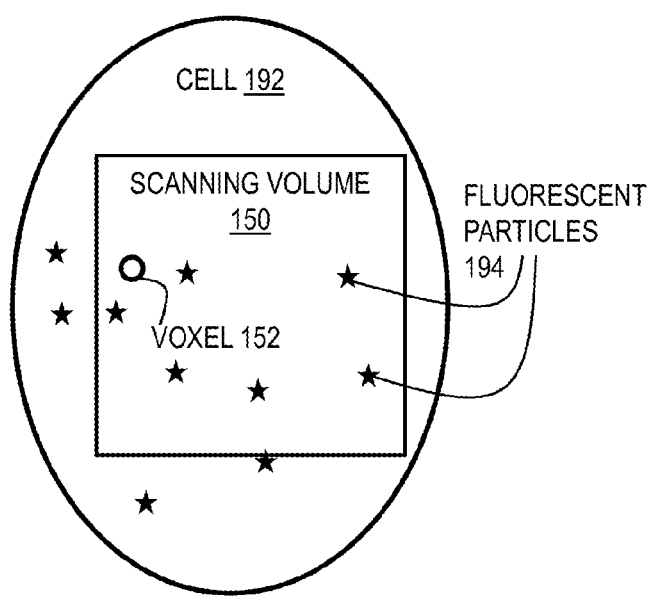
FIG. 1B is a block diagram that illustrates an example scanning volume sensitive to particle motion, according to an embodiment.

FIG. 1B is a block diagram that illustrates an example scanning volume 150 sensitive to particle motion, according to an embodiment. The scanning volume 150 is covered by voxels, such as voxel 152, arranged in one, two or three dimensions. In the illustrated embodiment, the scanning volume 150 is disposed inside a living cell 192 of the sample 190. Fluorescent particles 194 in the scanning volume 150 are detected in a corresponding voxel. A fluorescent particle is any particle that includes any fluorophore that emits light at a particular wavelength when illuminated by excitation light at different one or more wavelengths. Typically probes comprising a fluorophore bound to a molecule of interest are introduced into the sample 190, such as cell 192, during preparation of the sample 190. Typically, the fluorescent particles 194 are much smaller than the volume of the sample 192 corresponding to the voxel. At any particular voxel, e.g., voxel 152, the detected fluorescence will change in intensity over time as one or more of the fluorescent particles 194 move into and out of the volume of the sample corresponding to the voxel. This provides the intensity time series upon which FCS data, for example, is based.

Figure 1D:
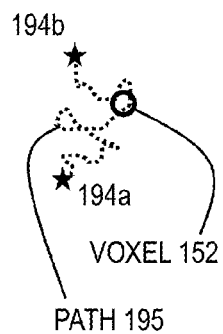
FIG. 1D is a block diagram that illustrates an example single particle motion relative to a scanning element, according to an embodiment.
Figure 1C:
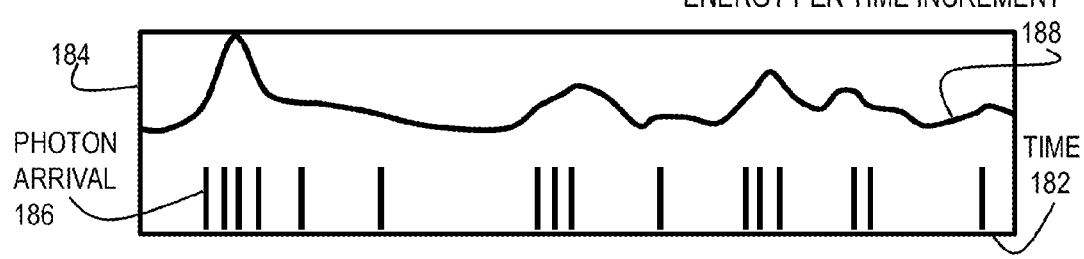
FIG. 1C is a block diagram that illustrates example intensity time series at a voxel, according to an embodiment.

FIG. 1C is a block diagram that illustrates example intensity time series at a voxel, according to an embodiment. The horizontal axis 182 is time in arbitrary units, and the vertical axis 184 is intensity in arbitrary units. In some systems, arrivals of individual photons at the fluorescent wavelength is detected in the voxel as an intensity time series, as indicated by photon arrival spike 186. In some systems, the power or energy per time increment, such as photon-count trace 188, is detected as the intensity time series, or computed from the photon arrival times.

FIG. 1D is a block diagram that illustrates an example single particle motion relative to a scanning element, according to an embodiment. A single fluorescent particle 194 moves from position 194a to position 194b along path 195. In a single voxel system, the particle is only detected when inside the volume corresponding to voxel 152. In a scanning system, voxels in the vicinity of voxel 152 detect the particle 194 at earlier and later times. The series of voxels that make successive detections in a scanning system are used to construct a trajectory that approximates the path 195 to within the spatial resolution and accuracy of the voxel positions and light noise levels of the source and detectors of the system.

Figure 1E:
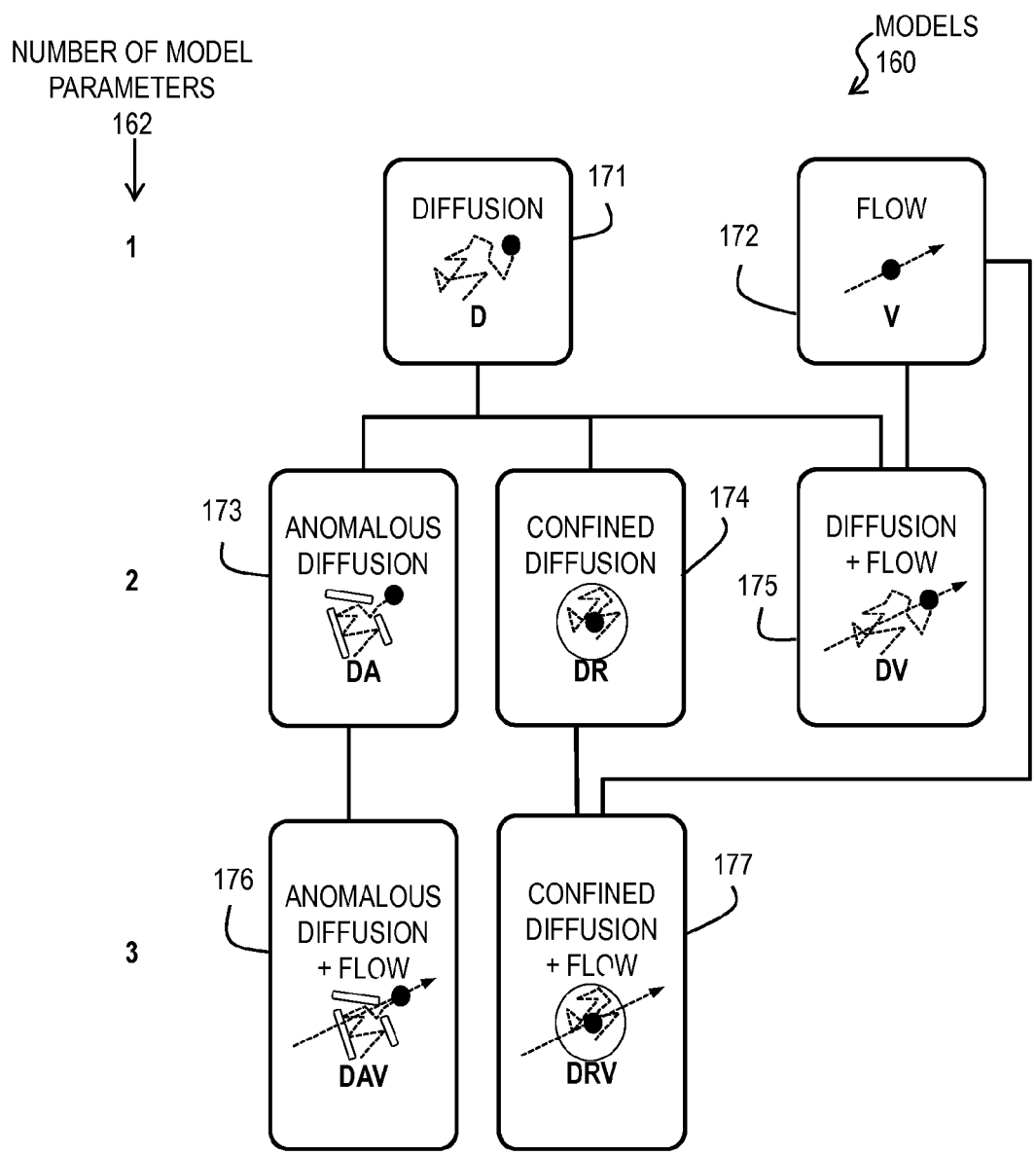
FIG. 1E is a block diagram that illustrates example candidate models for particle motion in living tissue and corresponding parameters, according to an embodiment.

FIG. 1E is a block diagram that illustrates example candidate models 160 for particle motion in living tissue and corresponding parameters, according to an embodiment. A parameter is a constituent of the model that is constant for a particular particle and environment, such as for a particular molecule in a particular cellular environment, but varies among different particles in different environments. To fit observations, a model is to be selected and parameter values for that model are to be determined.

Seven candidate models 171, 172, 173, 174, 175, 176 and 177 are indicated in FIG. 1E, arranged in rows by the number of parameters each includes. The number of model parameters 162 is indicated in each row of models. Two models, simple diffusion model 171 and simple flow model 172, each include one parameter. The diffusion model parameter is the diffusion coefficient D. The flow model parameter is the speed (also called velocity herein) v of flow. Three models, anomalous diffusion model 173, confined diffusion model 174 and simple diffusion with flow model 175, each include two parameters. The anomalous diffusion model 173 parameters are the diffusion coefficient D and the anomalous exponent a that accounts for the diffusion to be slowed by barriers, abbreviated DA. The confined diffusion model 174 parameters are the diffusion coefficient D and the radius of a reflective sphere $R_C$ within which the particle is confined, abbreviated DR. The diffusion with flow model 175 parameter are the diffusion coefficient D and the speed v of flow, abbreviated DV. Two models, anomalous diffusion with flow model 176 and confined diffusion with flow model 177, each include three parameters. The anomalous diffusion with flow model 176 parameters are the diffusion coefficient D, the anomalous exponent α and the speed v, abbreviated DAV. The confined diffusion with flow model 177 parameters are the diffusion coefficient D, the radius of a reflective sphere $R_C$ and the speed v, abbreviated DRV.

The models 160 show models relevant to single particle trajectories (SPT). In other embodiments other models are used. For example, in some embodiments, such as when analyzing FCS data, a two component diffusion model is included, which has two diffusion coefficient parameters $D_1$ and $D_2$ for two different particles labeled with the fluorophore. In some embodiments a three component diffusion model is used, with three diffusion coefficient parameters $D_1$, $D_2$ and $D_3$. In some embodiments a two component diffusion model with flow is used, with two diffusion coefficient parameters $D_1$ and $D_2$ and a speed parameter v. Thus, the set of models can include a range of model complexities (numbers of parameters) and non-trivial nesting relationships (shared parameters).

Given a set of models and data, Bayesian analysis provides a framework for determining relative probability of the models. For purposes of illustration, a broad discussion of Bayesian analysis is provided here. However the scope of the claims is not limited by the completeness or accuracy of this description.

The probability P of the kth model $M_k$ of a set of K different models given a vector of observed data y is designated $P(M_k|y)$ and is given by Bayes' theorem expressed as Equation 1a, $$P(M_k|y) = \frac{P(y|M_k)P(M_k)}{P(y)} \propto P(y|M_k) \quad (1a)$$

where y is a vector of one or more data values, P(y) is the prior probability of the data and $P(M_k)$ is the prior probability of the kth model $M_k$. The proportionality to $P(y|M_k)$ holds if the prior probabilities of all the models are equal for all k. The proportionality factor involves P(y). The normalized model probability $\underline{P}(M_k|y)$ is typically reported, given by Equation (1b)

$$\underline{P}(M_k|y) = P(M_k|y)/\{\Sigma_{j=1,K}P(M_j|y)\}, \quad (1b)$$

so that the prior probability of the data P(y) need not be evaluated.

The marginal probability $P(y|M_k)$ is given by an integral over parameter space $$P(y|M_k) = \int_\beta P(y|\beta,M_k)P(\beta|M_k)d\beta \quad (1c)$$

where β is a vector representing a particular set of values for the parameters of the kth model $M_k$ and the integral is over all such sets of parameter values.

Below are demonstrated useful techniques for evaluating and using the marginal probability $P(y|M_k)$ given data y sensitive to the motion of particles in a biological sample. For example, it is demonstrated below that using equal prior probabilities $P(M_k)$ of all the models leads to useful results for particle motion in living tissue. Thus, in practice, $P(y|M_k)$, called the marginal likelihood of the data y given the model $M_k$, (or simply "marginal likelihood" herein) is sufficient to make judgments about a preferred model. Also demonstrated below are approaches for evaluating the prior probabilities $P(y|\beta, M_k)$ and $P(\beta|M_k)$, which are found to be useful in determining $P(y|M_k)$ and thus analyzing data y responsive to motions of particles in a biological sample.

2. Method for Analyzing Particle Motion in a Biological Sample

Here is described a particular embodiment of a method for selecting one or more preferred models from a set of more than one candidate models and for determining one or more values for the set of one or more parameters corresponding to the selected model or models. For purposes of illustration, one or more steps will be described with respect to FCS data or MSD data. Those data types are described at a high level next.

Figures 2A, 2B:
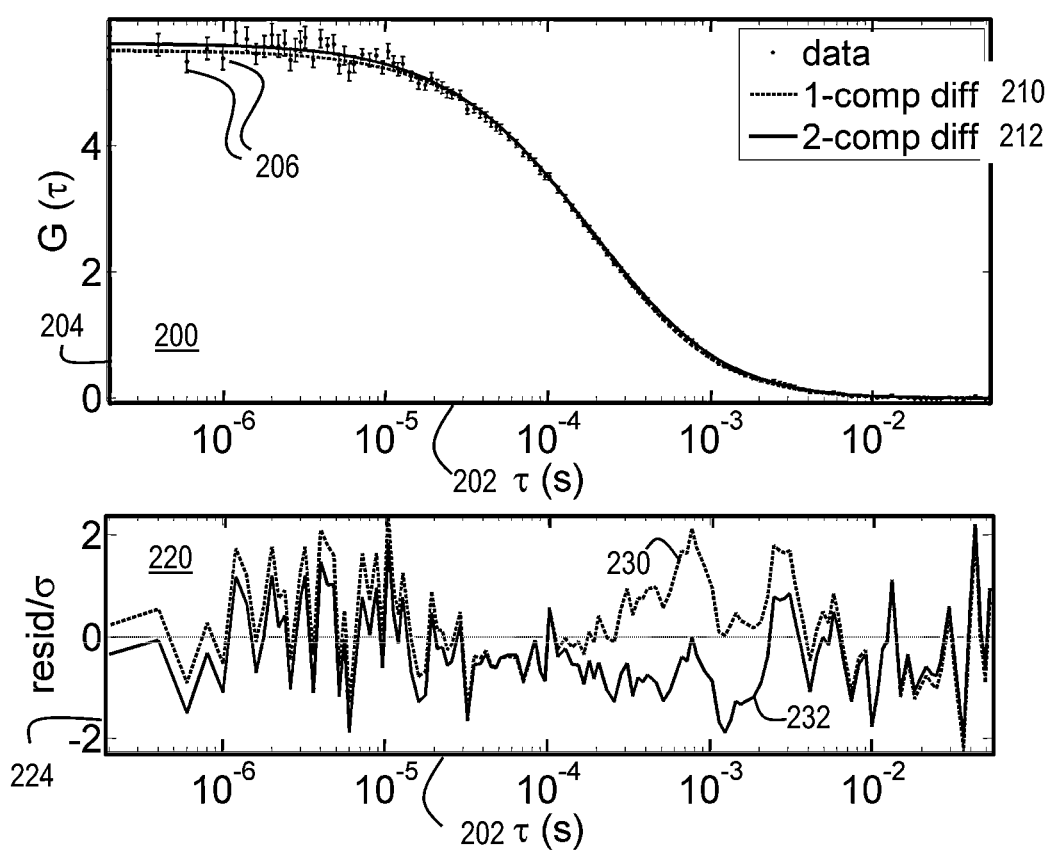
FIG. 2A through FIG. 2C are graphs that illustrate example simulated Fluorescence Correlation Spectroscopy (FCS) data, according to various embodiments.
Figure 2C:
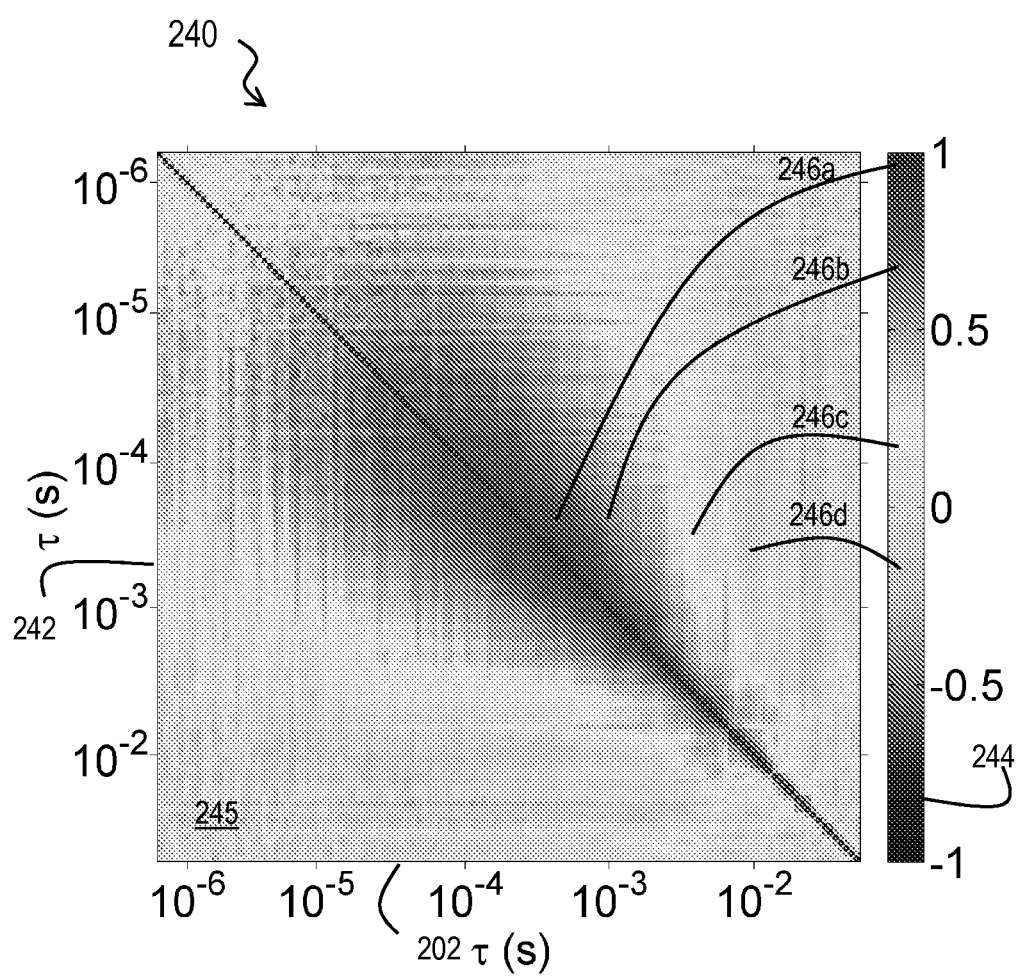

FIG. 2A through FIG. 2C are graphs that illustrate example simulated Fluorescence Correlation Spectroscopy (FCS) data, according to various embodiments. Details on the simulation of FCS data are given in a later section. FCS data are based on a temporal autocorrelation function (TACF) of each of one or more intensity time series. A TACF represents the degree to which intensity fluctuations are correlated over time and involves the product of two intensity measurements deviations separated by a time lag τ. The computation is repeated for several independent measurements of the same process separated by the same time lag and repeated at multiple lags to produce a TACF curve G(τ).

Specifically, the temporal autocorrelation function (TACF) of fluctuations in fluorescence intensity F(t) is calculated as G(τ) using, $$G(\tau) = \frac{\langle \delta F(t) \delta F(t+\tau) \rangle}{\langle F(t) \rangle^2} \quad (2)$$

Where $\delta F(t) = F(t) - \langle F(t) \rangle$, $\delta F(t) = F(t) - \langle F(t) \rangle$ is the fluctuation of the measured fluorescence intensity F(t), and $\langle \rangle$ denotes the ensemble average, which can be replaced by the time average by assuming ergodicity. All such TACFs in a data set characterizing a system, e.g., at one or more voxels in a homogeneous portion of a cell, are assembled to produce FCS data, and may be compared to FCS data in a different system. In practice, the TACF curve G(τ) is typically determined from the intensity data using a multi-tau correlator hardware circuit, well known in the art, which is generally faster than using software instructions for a general purpose computer described in the last section with reference to FIG. 18.

FIG. 2A is a graph 200 showing sample fits to the mean of 8 TACFs computed from simulated intensity traces for two distinct, point-like fluorescent species undergoing normal diffusion. The simulations use $D_1 = 63.1$ μm$^2$/second and $D_2=121.8$ μm²/second. Other aspects of generated simulated data are described in more detail in a later section. The logarithmic horizontal axis 202 indicates time lag τ in seconds, and the vertical, axis indicates the correlation value in arbitrary units. The average TACF points 206 are shown with vertical bars indicating the standard deviation σ of the eight TACF values at each lag. Time lags shorter than about 0.1 milliseconds (ms, 1 ms=$10^{-3}$ seconds) are associated with high correlation and higher noise than longer time lags. The traces 210 and 212 represent maximum likelihood fits of a one diffusion component model (like model 171) and a two diffusion component model, respectively. These fits are described in more detail in a later section. A preferred model is not indicated.

FIG. 2B is a graph 220 that depicts normalized residuals of the TACF values from each of the two model fits. The logarithmic horizontal axis 202 is the same as in FIG. 2A and indicates time lag in seconds, and the vertical axis is the residual value (G(t)−fit) divided by the standard deviation at each point. Trace 230 plots the normalized residuals from the one diffusion component model (model 171); and trace 232 plots the normalized residuals from the two diffusion component model. In the range of lags from about 0.1 ms ($10^{-4}$ seconds) to about 3 ms (about $3\times10^{-3}$ seconds) the residuals appear correlated. This suggests that noise in the data itself may be correlated, which has important consequences for selecting one or models, as described in more detail below.

FIG. 2C is a graph 240 that illustrates an example correlation matrix, according to an embodiment. The logarithmic horizontal axis 202 is the same as in FIG. 2A and indicates time lag in seconds. The logarithmic vertical axis 242 also indicates time lag in seconds using the same scale as the horizontal axis 202 but with time lag decreasing in the upward direction. The grayscale bar 244 indicates grayscale values for correlations from −1.0 to +1.0. Plotted are the correlations as products of simulated TACF values at all combinations of lags $(G(\tau_i)*G(\tau_j)$ for i,j=1, 128 ranging between time lags less than $10^{-6}$ seconds to time lags greater than $10^{-2}$ seconds) for each TACF curve averaged over 64 TACF curves. The simulations use $D_1=270$ μm²/second and $D_2=27$ μm²/second. The values are regularized using a shrinkage estimator. The procedures for deducing the correlation matrix values from data are described in more detail in a later section.

The matrix of correlated values is the correlation matrix 245 and is used as the noise correlation matrix, as described in more detail below. For uncorrelated noise, values are maximum along a diagonal from the upper left to the lower right and negligible off that diagonal. The correlation matrix 245 shows values near 1.0 indicated by 246a, values near 0.5 indicated by 246b, values near 0.0 indicated by 246c and small negative values indicated by 246d. Thus, the correlation matrix 245 shows substantial positive off-diagonal correlations in the areas indicated by 246a and 246b. Note that even though this correlation matrix 245 represents a different simulation than shown in FIG. 2B, the high off-diagonal values are concentrated between time lags of about $10^{-4}$ to about $10^{-3}$ where similar noise correlation was suggested in graph 220.

Figure 2D:
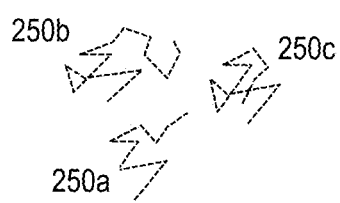
FIG. 2D through FIG. 2G are block diagrams that illustrates example Mean Square Displacement (MSD) data, according to an embodiment.
Figure 2E:
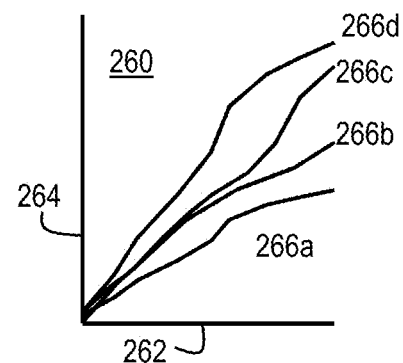

FIG. 2D through FIG. 2G are block diagrams that illustrates example Mean Square Displacement (MSD) data, according to an embodiment. FIG. 2D is a block diagram that illustrates an example set of three particle trajectories 250a, 250b and 250c, respectively (collectively referenced hereinafter as trajectories 250). FIG. 2E is a block diagram that illustrates example MSD curves. The horizontal axis 262 is time lag in arbitrary units; the vertical axis 264 is mean square displacement in arbitrary units. Four example MSD curves 266a, 266b, 266c, 266d, respectively (collectively referenced hereinafter as MSD curves 266), are drawn. Each MSD curve 266 is calculated from each trajectory 250 as follows. A single-particle trajectory consists of a sequence of N voxel positions given by Equation 3a.

$$\{r_i\}_{i=1}^N = \{x_i, y_i, z_i\}_{i=1}^N \qquad (3a)$$

where a particular particle is observed at specific times $\{t_i\}_{i=1}^N$ separated by a time step dt. The mean-square displacement (MSD) is then computed for time lags τ (in time units expressed as number of time steps dt) according to Equation 3b, $$MSD(\tau) \equiv \langle \Delta r(\tau)^2 \rangle = \frac{1}{N-\tau} \sum_{i=1}^{N-\tau} (r_{i+\tau} - r_i)^2 \qquad (3b)$$

Figure 2F:
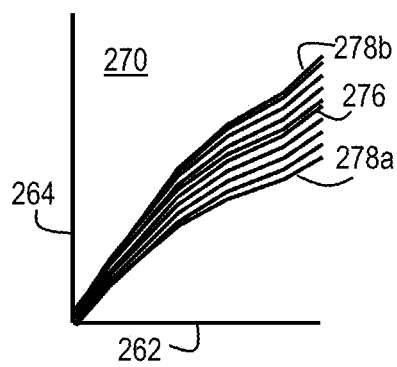
Figure 2G:
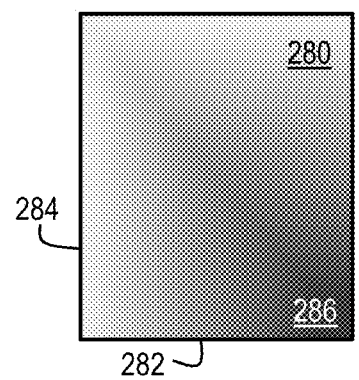

FIG. 2F is a block diagram that illustrates example mean and confidence levels curves. The horizontal axis 262 is time in arbitrary units; the vertical axis 264 is mean square displacement in arbitrary units, as in FIG. 2E. The mean MSD curve 276 is shown along with the standard deviation in the mean curve e.g., curve 278a and curve 278b, along with curves representing different confidence limits. The set of MSD curves from individual particle trajectories is used to calculate the mean MSD curve. FIG. 2G is a block/diagram that illustrates an example correlation matrix. The horizontal axis 282 and vertical axis 282 each indicates time lag in arbitrary units. The error covariance matrix 286 is determined from the MSD curves in FIG. 2E.

In some embodiments, the mean MSD curves 276 and error covariance matrix 286 serve as inputs to the Bayesian inference procedure described below with reference to FIG. 3, which outputs model probabilities and parameters. These model probabilities can then be interpreted in the context of the biological system, and, if necessary to improve resolution of complex models, additional trajectories can be collected or existing trajectories can be re-classified into less heterogeneous sub-groups, in various embodiments, as described below.

FIG. 3 is a flow diagram that illustrates an example method for determining relative probability of models for particle motion in a biological sample and corresponding values of model parameters, according to an embodiment. Although steps are depicted in FIG. 3, and in subsequent flowcharts FIG. 4A, FIG. 4B, FIG. 5 and FIG. 6A, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301, multiple candidate models are hypothesized to describe observed motions of particles in biological samples. Each model includes one or more adjustable parameters that are treated as a constant for a particular system of particles and a biological sample, and allowed to vary among different systems. For example the models of FIG. 1D are considered candidates for data based on single particle trajectories, like MSD data, along with multiple diffusion models, with or without flow, for data based on fluorescent intensities at a fixed volume.

In step 302, the effect of a model on a particular measurement type is determined as a function of model parameters. That is, the dependence of a particular type of measurement data, such as FCS or MSD type data, is determined as a function of model parameters for each hypothesized model. For example, the effect of single component diffusion model parameter $D_1$ is determined for TACF data or MSD data to be analyzed.

In some embodiments the dependence of the TACF on the simple flow (also called convection or advection) model 172 is given by Equation 4a for convection TACF $G_c(\tau)$.

$$G_C(\tau) = \langle N \rangle^{-1} \exp[-(\tau/\tau_C)^2] \qquad (4a)$$

where N is the average number of fluorescent particles in the detection volume corresponding to one voxel, and $\tau_C$ is the convective time scale, given by the width $w_0$ of the detection volume divided by the speed parameter v.

In some embodiments $N_D$ non-interacting fluorescent species undergo normal diffusion and the focal volume corresponding to one voxel is a 3 dimensional Gaussian ellipsoid with transverse width $w_0$ and height $z_0$. In such embodiments, the TACF has the closed form solution given by Equation 4b for diffusion TACF $G_D(\tau)$.

$$G_D(\tau) = \sum_{i=1}^{N_D} a_i \left(1 + \frac{\tau}{\tau_{D_i}}\right)^{-1} \left(1 + \frac{\tau}{s^2 \tau_{D_i}}\right)^{-\frac{1}{2}} \qquad (4b)$$

where $a_i = (B_i)^2 \langle N_i \rangle / (\Sigma_i B_i \langle N_i \rangle)^2$ and $\tau_{D_i} = w_0^2 / 4 D_i$ are the correlation amplitude and the diffusion time of component i, respectively. $s = z_0/w_0$ is the aspect ratio of the focal volume or molecule detection function (MDF), and $B_i$ is the brightness of component i and is given by $B_i = \sigma_{abs} q_f \kappa q_D$, where $\sigma_{abs}$ is the absorption cross-section of the fluorophore, $q_f$ is the quantum yield of fluorophores, $\kappa$ is the overall transmittance of the optics that accounts for total photon loss due to light transmission and collection of optical components, and $q_D$ is the quantum efficiency of the detection device.

In the case of high illumination intensity, the high fraction of molecules being excited to the non-fluorescent triplet state results in additional fluctuations in intensity on a short time scale, which can be described by Equation 4c, $$G(\tau) = \left(1 + \frac{F_{trip}}{1 - F_{trip}} \exp\left(-\frac{\tau}{\tau_{trip}}\right)\right) G_D(\tau), \qquad (4c)$$

where $F_{trip}$ is the fraction of molecules in the triplet state, and $\tau_{trip}$ is the triplet blinking time. $F_{trip}$ increases with the increase of the illumination intensity. When $F_{trip} \ll 1$, Eq. 4c can be approximated by $G_D(\tau)$ given in Equation 4b.

In some embodiments the effect of two dimensional diffusion and simple flow of model 175 on the measurement of TACFs is given by Equation 4d for diffusion and convection TACF $G_{DC}(\tau)$.

$$G_{DC}(\tau) = \frac{1}{\langle N \rangle} \left(1 + \frac{\tau}{\tau_D}\right)^{-1} \exp\left[-\left(\frac{\tau}{\tau_C}\right)^2 \left(1 + \frac{\tau}{\tau_D}\right)^{-1}\right] \qquad (4d)$$

where D is the diffusion coefficient in two dimensions for a single diffusing component and $\tau_C$ and $\tau_D$ are as defined above.

For MSD data, the following functional forms, at least, are available. The effect of simple diffusion model 171 on the measurement of MSD is given by Equation 5a for diffusion $MSD_D$.

$$MSD_D(\tau) = 6D\tau \qquad (5a)$$

The effect of anomalous diffusion model 173 on the measurement of MSD is given by Equation 5b for anomalous diffusion $MSD_{DA}$.

$$MSD_{DA}(\tau) = 6D\tau^\alpha \qquad (5b)$$

The effect of confined diffusion model 174 on the measurement of MSD is given by Equation 5c for confined diffusion $MSD_{DR}$.

$$MSD_{DR}(\tau) = R_C^2(1 - e^{-6D\tau/R_C^2}) \qquad (5c)$$

The effect of simple flow model 172 on the measurement of MSD is given by Equation 5d for flow $MSD_V$.

$$MSD_V(\tau) = v^2 \tau^2 \cdot MSD_{DR}(\tau) = R_C^2(1 - e^{-6D\tau/R_C^2}) \qquad (5d)$$

Combinations of these physical processes, for example diffusion with directed motion, yield more complex motion models. The dependence of MSD data on many of these complex models have been described; and, any equation known in the art may be used in various embodiments.

Note that the same model produces different equations for the effects on different data types. For example, compare the simple flow (convection) model for TACF in Equation 4a with the simple flow model for MSD in Equation 5d.

In step 305, data of the measurement type is obtained. Any method may be used to receive the data. For example, measurements can be made using the experimental setup 100, previously measured data can be retrieved from a data structure, including one or more databases, data can be simulated using one or more simulation routines on one or more computers. For example, the simulated TACF data used to derive points 206 shown in FIG. 2A or simulated SPTs used to derive MSD curves 266 in FIG. 2E are obtained.

In step 307 noise correlation is determined based on the data obtained. As described in more detail in later steps, the noise correlation is used to derive the marginal likelihood $P(y|M_k)$ in several useful embodiments. Several effective methods have been developed herein to determine the noise correlation useful for deriving the marginal likelihood from several measurement types.

FIG. 4A and FIG. 4B are flow diagrams for different data types that each illustrates an example method for performing step 307 in FIG. 3, which determines noise correlation, according to an embodiment. FIG. 4A is flow diagram that illustrates an example method 400 that is an embodiment of step 307 for TACF data. Two independent approaches to estimating the covariance matrix C for distinct types of FCS data are presented. First, when multiple independent TACF curves measured from the same physical process are available, C may be estimated by calculating the sample covariance matrix S of all TACF curves. Estimating noise from multiple TACF curves is only justified when all of the curves come from measurements of the same physical process and the variation across curves is purely from intrinsic statistical error in the correlation function estimator due to the finite sample size. However, in applications of FCS to in vivo biological data it may be preferable to evaluate model probabilities directly from the same, single sample. In this case, an alternative approach is to estimate the noise correlation in a single TACF by calculating the noise correlation from the underlying intensity time series, such as photon-count products based on a raw photon-count trace 188 or photon arrival time information 186 as depicted in FIG. 1C.

In step 401, it is determined whether multiple independent TACF curves measured from the same physical process are available. If so, then the multiple TACF curves are used in steps 403 through 407. Otherwise, noise correlation is derived based on an underlying time series in steps 411 through 419.

If multiple independent TACF curves measured from the same physical process are available, then, in step 403 a mean TACF curve is determined by averaging values of $G(\tau_l)$ from all TACF curves at each $\tau_l$. For J curves, the average is given by Equation 6a.

$$\overline{G}(\tau_l) = \Sigma_{j=1,J} G(\tau_l)/J \tag{6a}$$

In step 405, the sample covariance matrix S is determined with matrix elements $S_{kl}$ in row k and column l as given by Equation 6b.

$$S_{kl} = \frac{1}{J-1} \sum_{j=1}^{J} (G^{(j)}(\tau_k) - \overline{G}(\tau_k))(G^{(j)}(\tau_l) - \overline{G}(\tau_l)) \tag{6b}$$

where $G^{(j)}$ is the jth individual TACF curve, $\tau_k$ is time lag k*dt and $\tau_l$ is time lag l*dt. The covariance of the mean TACF curve is then given by Equation 6c.

$$S_m = 1/J \cdot S \tag{6c}$$

and this covariance matrix is taken as the noise correlation C in some TACF embodiments.

The sample covariance matrix is only well-conditioned when the number of observations (i.e., the number of available independent TACF curves) is larger than the dimension of C, which is generally not true for high dimensional data such as TACF curves (typically 128 values of time lag $\tau_l$). Therefore, in step 407, a shrinkage estimator for covariance matrices is used to ensure that the estimated matrix C is well-conditioned and has lower mean squared error (MSE) than the sample covariance matrix S. The shrinkage estimator is the linear combination of the sample covariance matrix and a low dimensional shrinkage target, given by Equation 7.

$$S^* = \lambda T + (1-\lambda)S \tag{7a}$$

where T is the shrinkage target, which is usually a diagonal matrix, and $\lambda$ is the optimal shrinkage weight associated with the specific shrinkage target. The shrinkage weight $\lambda$ depends on the uncertainty in S, which is determined by the number of samples from which S is calculated. The more samples are available, the smaller $\lambda$ is and the closer $S^*$ is to S.

To choose the optimal shrinkage target for covariance estimates of noise in TACFs, we explored different shrinkage targets that preserve the characteristic structure of the noise covariance in the TACF. For the target B and D, the shrinkage estimate of the covariance is given by Equation 7a. $t_{ij}\lambda$ The target B is a uniform diagonal matrix. Target D is the non-uniform diagonal matrix of the variance. The target D shrinks the covariance but preserves the variance. In contrast, the "two-way" target shrinks the variance and the correlation individually. The matrix element $s_{ij}^* s_{ij}^*$ of the shrinkage estimate with the "two-way" target is given by Equations 7b through 7f.

$$s_{ij}^* = r_{ij}^* \sqrt{(v_i^* v_j^*)} \tag{7b}$$

where:

$$r_{ij}^* = (1-\lambda_1) r_{ij} \tag{7c}$$

$$v_i^* = \lambda_2 v_{median} + (1-\lambda_2) v_i \tag{7d}$$

$$\lambda_1 = \min\{1, \Sigma_{i \neq j} \text{Var}(r_{ij})/(\Sigma_{i \neq j} r_{ij}^2)\} \tag{7e}$$

$$\lambda_2 = \min\{1, \Sigma_i \text{Var}(v_i)/(\Sigma_i (v_i - v_{median})^2)\} \tag{7f}$$

and $r_{ij} r_{ij}$ is a matrix element of a sample correlation matrix. The target B shrinkage estimate is defined in Equations 7g and 7h.

$$t_{ij} = \{v = E(s_{ii}) \text{ if } i=j \{0 \text{ if } i \neq j \tag{7g}$$

$$\lambda = \Sigma_{i,j} \text{Var}(s_{ij})/\{(\Sigma_{i \neq j} s_{ij}^2) + \Sigma_i (s_{ii} - v)^2)\} \tag{7h}$$

It was found that different shrinkage targets all reduce the mean square error (MSE) and yield well-conditioned estimates for the covariance structure of the noise in the TACF. An advantage of choosing the "two-way" target for TACF data is that it yields the smallest uncertainty in model probabilities. (See Opgen-Rhein, R., and K. Strimmer, "Accurate ranking of differentially expressed genes by a distribution-free shrinkage approach," *Stat. Appl. Genet. Mol. Biol.* v6, p 20, 2007.) For MSD data, the target B shrinkage estimate was preferred.

As stated above, the regularized sample covariance of the mean TACF curve is taken to be the noise correlation in this embodiment. The TACF correlation matrix depicted in FIG. 2C is such a shrinkage estimate of the noise correlation matrix for TACFs.

If it is determined, in step 401, that multiple independent TACF curves measured from the same physical process are not available, then noise correlation is derived based on an underlying time series in steps 411 through 419. For the multi-tau correlator hardware used to accelerate the computation of TACF curves, the TACF s calculated according to Equation 8a and 8b for a photon-count trace with acquisition time T and sampling time (channel width) $\Delta\tau_i$.

$$G(\tau_k) = G(k\Delta\tau_i) = \frac{\frac{1}{M}\sum_{m=1}^{M} \delta n_m \delta n_{m+k}}{\overline{n}_0 \cdot \overline{n}_k} \tag{8a}$$

with $$\overline{n}_j = \frac{1}{M}\sum_{m=1}^{M} n_{m+j} \tag{8b}$$

where $M = T/\Delta\tau_i - k$ is the number of possible counts separated in time by the lag $k\Delta\tau_i$, $n_m$ is the photon count at $m\Delta\tau_i$, $\delta n_m = n_m - \overline{n}_0$, $\delta n_{m+k} = n_{m+k} - \overline{n}_k$. As shown in Equation 8a, $G(\tau)$ is the mean of the underlying photon-count products. Therefore, the covariance of $G(\tau_k)$ and $G(\tau_l)$ may be calculated from the covariance of the underlying count products $\{\delta n_m \delta n_{m+k}, \delta n_m \delta n_{m+l}\}_{m=1}^{M}$. Thus, in step 411 the underlying intensity time series is obtained.

Note that calculating the variance or covariance in the photon-count products between time lags requires either independent samples of these products at each $\tau_k$ or knowledge of the correlations between the samples of these products at each $\tau_k$, otherwise the noise level will be underestimated. For FCS data, the photon-count products $\{\delta n_m \delta n_{m+k}\}_{m=1}^{M}$ at any $\tau_k$ are not independent and their correlations are given by a fourth-order correlation function.

Here is introduced a procedure to circumvent this problem by performing a block-transformation on the photon-count products to obtain independent samples. This approach is used extensively in the molecular simulation community to obtain independent estimates from highly correlated molecular trajectories (see, for example, Frenkel, D., and B. Smit., *Understanding molecular simulation: from algorithms to applications*, Academic Press, San Diego, 2002). The covariance matrix of the mean can then be calculated directly from these transformed, independent samples without the evaluation of the higher order correlation function. Thus, in some embodiments, in step 413, the block transformation of the intensity time series is performed, as described next.

The blocking method seeks the minimal averaging time (or block time) beyond which the transformed samples (or the block-averages) of the photon-count products are no longer correlated. We define $$p_m(k) = \frac{\delta n_k \delta n_{m+k}}{\bar{n}_0 \cdot \bar{n}_k},$$

and substitute into Equation 8a to produce Equation 8c.

$$G(k\Delta \tau_i) = \frac{1}{M} \sum_{m=1}^{M} p_m(k) \tag{8c}$$

The block-transformed sample $p_m'(k)$ with block time $t_b$ is given by the block-average of all $p_m(k)$ within $t_b$, as given by Equation 8d.

$$p_m'(k) = \frac{1}{\nu}[p_{(m-1)\nu+1}(k) + p_{(m-1)\nu+2}(k) + \ldots + p_{m\nu}(k)] \tag{8d}$$

where $V = t_b/\Delta \tau_i$ is the number of samples in the block. The covariance between $p_m'(k)$ at different m will decrease as $t_b$ increases because correlations between the underlying photon count decay over time. Note that Equation 8c still holds for the transformed samples $p_m'(k)$, so the covariance of $G(\tau_k)$ and $G(\tau_l)$ can be calculated from $p_m'(k)$ as well. When $t_b$ is beyond the minimal block time needed to obtain independent blocked samples, the matrix elements $S_{kl}$ in the sample covariance matrix S of $G(\tau)$ can be calculated directly from these independent transformed samples, as given in Equation 8e.

$$S_{kl} = \frac{1}{M'(M'-1)} \sum_{m=1}^{M'} (p_m'(k) - \bar{p}'(k))(p_m'(l) - \bar{p}'(l)) \tag{8e}$$

where M' is the number of transformed samples. In step 415 the mean transformed products (p'(k) overbar) are determined for each lag $k\Delta \tau_i$. In step 417, the transformed sample covariance matrix S is calculated using Equation 8e for each row and column element.

The minimal block time depends on the correlation time of the measured physical process and the functional form of its decay. In practice, the minimal block time can be determined by plotting $S_{kk}$ at $\tau_k$ as a function of the block time $t_b$, and finding the minimal time after which $S_{kk}$ becomes invariant to $t_b$. This is shown for an example embodiment below with reference to FIG. 8A.

In step 419, a shrinkage estimator for covariance matrices is used to ensure that the estimated matrix C is well-conditioned and has lower mean squared error (MSE) than the sample covariance matrix S, similar to step 407 described above.

FIG. 4B is flow diagram that illustrates an example method 450 that is an embodiment of step 307 for MSD data. Particle motion typically contains a stochastic diffusive component, and each step in a particle trajectory represents a single observation of that stochastic behavior. When a trajectory is used to calculate mean squared displacement values, the same set of displacements grouped into different sized windows is used to calculate the MSD value at each time lag $\tau$. In other words, the same observations are reused for each calculation. This process leads to strong correlations in the deviations of the calculated MSD values from their expected values at different time lags. The correlation strength depends on the difference between two time lags $\tau_1$ and $\tau_2$, and the magnitude of $\tau_1$ and $\tau_2$ compared to an individual displacement in the trajectory. Over-fitting in the presence of these correlated errors occurs because, for example, the confined diffusion model can fit pure diffusion MSD curves that trend down at large time lags, and the diffusion plus flow model can fit pure diffusion MSD curves that trend up at large time lags.

In step 451, it is determined whether the measurements are for a system with pure diffusion and negligible position error in the imaging system. If so, an analytical solution for noise correlation is available that depends on $\tau_1$ and $\tau_2$ and the total number N of points in the trajectory. Here $\tau_1$ and $\tau_2$ are in units of number of time steps dt along the trajectory. In step 453 the analytical expression is used for noise correlation, as given by Equations 9a for $\tau_1 + \tau_2 \leq N$ and 9b for $\tau_1 + \tau_2 > N$.

$$\sigma_{\tau_1,\tau_2}^2 = \frac{\tau_1}{6(N-\tau_1)(N-\tau_2)}[4\tau_1^2(N-\tau_1) + 2(N-\tau_1) - \tau_1^3 + \tau_1 + (\tau_2 - \tau_1)(6\tau_1(N - \tau_2 - 4\tau_1^2 - 2)](4Ddt)^2. \tag{9a}$$

$$\sigma_{\tau_1,\tau_2}^2 = \frac{1}{6(N-\tau_1)}[6\tau_1^2(N-\tau_1) - 4\tau_1(N-\tau_1)^2 + (N-\tau_1)^3 + 4\tau_1 - (N-\tau_1) + (\tau_2 - \tau_1)[(\tau_1 + \tau_2)(2(N-\tau_1) + N - \tau_2) + 2\tau_1(N - \tau_2) - 3(N - \tau_1)^2 + 1]](4Ddt)^2. \tag{9b}$$

If it is determined, in step 451, that the measurements are not for a system with pure diffusion or that position error in the imaging system is not negligible, then control passes to step 461. The error covariance matrix can be estimated from multiple observations of the MSD values as a function of time lag $\tau$, this estimate is called the sample covariance matrix. The multiple MSD curves used to calculate the sample covariance matrix are preferably independent of one another; e.g., they are ideally derived from independent, non-overlapping particle trajectories. These independent MSD curves can be obtained either from different particle trajectories or from splitting a single particle trajectory into multiple non-overlapping sub-trajectories. In the latter case, the full trajectory of N-1 steps (based on N position measurements) is divided into M non-overlapping sub-trajectories of |(N-1)/M| steps each. Note that this single-trajectory-based method requires that the largest $\tau$ appearing in the MSD curve not be greater than the number of steps in the sub-trajectories. There is therefore a tradeoff between the ability to accurately estimate the covariance matrix (which improves with the number of sub-trajectories M) and the time range spanned by the MSD curve.

In step 461, it is determined whether there are multiple independent MSD curves available. If not, then in step 463, the single trajectory for the single MSD curve is broken up into multiple independent sub-trajectories, that nonetheless, appear to belong to the same system of particle motion in living tissue conditions. In step 465, shorter MSD curves are derived for each sub-trajectory using Equation 3b, described above. Control then passes to step 471, described below.

If it is determined, in step 461, that there are multiple independent MSD curves available, then control passes directly to step 471. In step 471 a mean MSD curve is derived from the multiple MSD curves.

In step 473 a sample covariance matrix for deviations of individual MSD curves from the mean MSD curve is determined. For example, given M independent observations of MSD($\tau_i$) values at each $\tau_i$, indicated by MSD$_i^m$ for m=1, M with an average value of $\overline{MSDi}$, the residuals between each individual MSD curve and the mean MSD curve are used to estimate the variance and the covariance of the noise in the MSD estimates. For each MSD curve, the residual $\epsilon i^m$ of each curve m at each time lag $\tau_i$, is given by Equation 10a.

$$\epsilon_i^m = MSDi^m - \overline{MSDi} \qquad (10a)$$

and the entries to the sample mean covariance matrix S are given by Equation 10b.

$$S_{ij} = \langle \epsilon_i^m \epsilon_j^m \rangle / (M-1) \qquad (10b)$$

When the number of available MSD curves M is less than the number of points in the MSD curve, the estimated covariance matrix will be singular and must be regularized to obtain a non-singular covariance matrix C to use as the measure of noise correlation. Thus, in step 475, the sample covariance matrix is regularized using a shrinkage estimator, as described above for TACF data.

Returning to FIG. 3, after the noise correlation is determined from the data in one of the embodiments of step 307, control passes to step 310 to determine, based on the noise correlation, P(y|M$_k$), the marginal likelihood of the data given the model. In one embodiment, step 310 includes steps 311 and 313.

In step 311, the distribution of parameter values are determined for each model based on the noise correlation to produce probability density functions for sets of parameter values β, such as prior probabilities P(β|M$_k$) or posterior probabilities P(β|y, M$_k$), or both. For example, the maximum likelihood parameter values are determined using generalized least squares (GLS). In step 313, P(y|Mk), the marginal likelihood of the data given the model, is determined by evaluating the integral of Equation 1c using either the prior probabilities P(β|M$_k$), or statistics of the posterior probabilities P(β|y, M$_k$) and a Laplace approximation.

FIG. 5 is a flow diagram that illustrates an example method 500 for performing step 311 in FIG. 3, which determines distribution of values for one or more parameters of a model, according to an embodiment. Thus method 500 is a particular embodiment of step 311.

Given a known or estimated covariance matrix C for the errors $\epsilon i$ in the estimated values of $y_i$ (either $\overline{G}(\tau_i)$ or MSDi) the fitting equation for function $f$ representing model Mk is given by Equation 11a $$y_i = f(x_i, \beta) + \epsilon_i \qquad (11a)$$

which can be expressed in terms of the vector y of all the $y_i$, the vector x of all the $x_i$ and the vector $\epsilon$ of all the $\epsilon_i$, as in Equation 11b.

$$y = f(x, \beta) + \epsilon \qquad (11b)$$

This equation is transformed into a coordinate system in which the errors are uncorrelated by transforming both the function $f$ and the data $y_i$ by the matrix A, to give Equation 11c.

$$Ay = Af(x, \beta) + A\epsilon \qquad (11c)$$

by finding a transformation matrix A such that the transformed errors A$\epsilon$ have a covariance matrix A$\epsilon$ (A$\epsilon$)$^T$ whose expected value is equal to the identity matrix I. This condition is expressed in Equation 11d $$A\epsilon = E[A\epsilon(A\epsilon)^T] = AE[\epsilon\epsilon^T]A^T = ACA^T = I \qquad (11d)$$

where E[ ] indicates the expectation value of the quantity inside the square brackets. Equation 11c implies that C satisfy equation 11e.

$$C^{-1} = A^T A \qquad (11e)$$

An appropriate transformation matrix A is found by taking the Cholesky decomposition C=LL$^T$ and setting A=L$^{-1}$ (e.g., using the MATLAB function chol (in MATLAB™ from MathWorks, Inc.™ Natick, Mass.). Ordinary least squares can then be used to obtain the maximum likelihood estimate of the parameter values $\beta_{MLE}$ (called $\beta_{post}$ herein) and the covariance matrix of the MLE parameter estimates (called $\Sigma_\beta$ herein) for the transformed Equation 11b. Any least squares (LS) or maximum likelihood estimation (MLE) may be used. For example, least squares regression with Gaussian noise is performed on the model and data transformed by the matrix L using the MATLAB function nlinfit (in MATLAB™ from MathWorks, Inc.™ of Natick, Mass.) which employs the Levenberg-Marquardt algorithm to implement a nonlinear least squares regression assuming uniform, independent error terms.

$\beta_{best}$ is the maximum of the posterior distribution of parameter values P(β|y, M$_k$) and is also called the Bayesian point estimate; and $\Sigma_\beta$ is the covariance matrix of β estimated at $\beta_{post}$. The value of $\Sigma_\beta$ is used in a Laplace approximation, described below.

Therefore, in step 501 the noise covariance matrix C is decomposed into matrix L. In step 503, the model and data are transformed using the L matrix, as given by Equation 11c where A=L$^{-1}$, so that the noise A$\epsilon$ is uncorrelated. In step 505 the maximum likelihood estimation (MLE) of the transformed model A$f$(x, β) and data Ay is used to obtain the posterior most likely values for model parameter values $\beta_{post}$ and covariance matrix $\Sigma_\beta$ at $\beta_{post}$.

If noise correlation is minimal in some embodiments, the covariance matrix C approaches the identity matrix; and, standard maximum likelihood estimation is suitable for estimating the best values of the parameters $\beta_{post}$ and their covariance matrix $\Sigma_\beta$. In such embodiments, steps 501 and 503 are omitted and A=I.

In some embodiments, the prior probabilities P(β|M$_k$) for the values of the parameters for a model are utilized, as described in more detail below. For such embodiments, method 500 includes step 507 to estimate the P(β|M$_k$) based on the posterior probabilities.

In an illustrated embodiment, the prior probabilities P(β|M$_k$) are taken to be a constant normalized to an integrated value of 1.0 over a range centered on $\beta_{post}$ and large compared to a confidence interval or standard deviation $\sigma_\beta$ based on the covariance for that parameter in $\Sigma_\beta$. Preferably the range is more than about ten times the standard deviation $\sigma_\beta$ based on the covariance of the parameter values in $\Sigma_\beta$. In various experimental embodiments, probability P(β|M$_k$) is taken as a constant that is normalized to one within the parameter range $2\gamma_f$ times the parameter standard deviation $\sigma_\beta$ centered at $\beta_{post}$ in each model i, as given by Equation 12.

$$\beta = \cap_{i=1,k} \{\beta_{post}^{(i)} - \gamma_f \sigma_\beta^{(i)}, \beta_{post}^{(i)} + \gamma_f \sigma_\beta^{(i)}\} \qquad (12)$$

and parameter standard deviations $\sigma_\beta$ are estimated as the square root of the diagonal terms of $\Sigma_\beta$ and i is an index indicating the model. $\gamma_f$ is chosen to be 200, in various embodiments, so that the prior range is significantly larger than the likelihood. The effects of different choices of prior on model probabilities are described in a later section.

The choice of uniform prior parameter value range may affect the model probability computed. However, as is described in more detail below, it was determined that, if the uniform prior range is sufficiently large, the computed model probabilities are not sensitive to the uniform prior range.

In step 509, it is determined whether the distributions of parameter values are to be determined for another candidate model. If so, steps 503 through 507 are repeated for the next candidate model. Otherwise method 500 is complete and control passes to step 313 in FIG. 3.

In step 313, the marginal likelihood of the data for each model is determined based on distributions of values for the parameters of each model. As given in Equation 1c, the marginal likelihood $P(y|M_k)$ depends on integrating a product of $P(y|\beta, M_k)$ and the prior probability $P(\beta|M_k)$ over parameter value space. In the original coordinate system, $P(y|\beta, M_k)$ the likelihood of the data y with noise covariance matrix C given a set of parameter values $\beta$ for model $Mk=f(x, \beta)$ is given by Equation 13a.

$$P(y|\beta,M_k)=(2\pi)^{-n/2}|C|^{-1/2}\exp(-\frac{1}{2}(y-f(x,\beta))^T C^{-1}(y-f(x,\beta))) \tag{13a}$$

Which is equivalent to Equation 13b after the decomposition of C into $L L^T$.

$$P(y|\beta,M_k)=(2\pi)^{-n/2}|C|^{-1/2}\exp(-\frac{1}{2}(y-f(x,\beta))^T(L^{-1})^T L^{-1}(y-f(x,\beta))) \tag{13b}$$

The use of a Laplace approximation to determine the marginal likelihood $P(y|M_k)$ is justified when the posterior distribution of the parameters as given by $\beta_{post}$ and $\Sigma_\beta$, approaches a Gaussian. The Laplace approximation is given by Equation 13c.

$$P(y|M_k)=(2\pi)^{p/2}|\Sigma_\beta|^{1/2}P(y|\beta_{post},M_k)P(\beta_{post}|M_k), \tag{13c}$$

where p is a number of parameters in $\beta$. It has been determined in the current work that the posterior distribution of parameters approaches a Gaussian for typical TACF curves.

In step 313, at least one of these approaches is used to evaluate $P(y|M_k)$.

Figure 6:
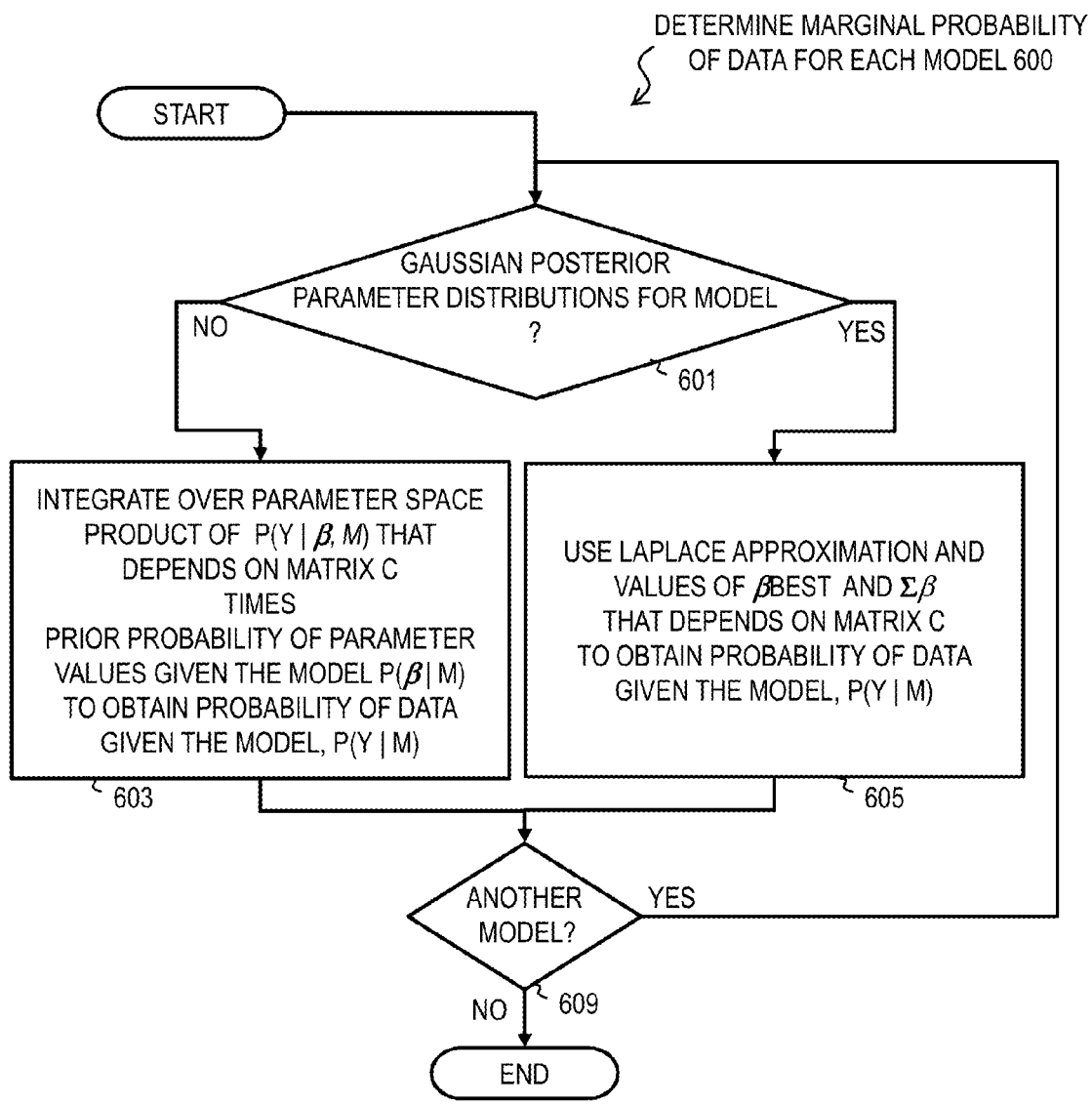
FIG. 6 is a flow diagram that illustrates an example method for performing a step in FIG. 3, which determines marginal likelihood of the observed data for each model, according to an embodiment.

FIG. 6 is a flow diagram that illustrates an example method 600 for performing step 313 in FIG. 3, which determines marginal likelihood of the observed data for each model, according to an embodiment.

In step 601 it is determined whether the posterior distribution of the parameters as given by $\beta_{post}$ and $\Sigma_\beta$, approaches a Gaussian. If so, then in step 605 the Laplace approximation given in Equation 13 is used to evaluate $P(y|M_k)$, the marginal likelihood. If not, then in step 603, a numerical integration, such as a Monte Carlo integration, is performed over parameter value space of the product of $P(y|\beta, M_k)$ given by Equation 12a or 12b and the prior probability $P(\beta|M_k)$ determined in step 507, described above.

To integrate marginal likelihood, a Monte Carlo method draws independent random samples $\beta^{(g)}$ from the prior distribution $P(\beta|M_k)$. This integration is then evaluated as $$P(y|M_k) = \frac{1}{N}\sum_{g=1}^{N} P(y|\beta^{(g)}, M_k). \tag{14}$$

Beyond the above simple Monte Carlo method, there are other variants of the Monte Carlo method for computing marginal likelihood, such as importance sampling, the harmonic mean estimate, and using Metropolis-Hasting output (see, for example, Chib, S., "Marginal likelihood from the Gibbs output," *J. Am. Stat. Assoc.*, v90, pp 1313-1321, 1995).

In step 609, it is determined whether the marginal likelihood $P(y|M_k)$ is to be determined for another candidate model. If so, step 601 and step 603 or 605 are repeated for the next candidate model. Otherwise method 600 is complete and control passes to step 315 in FIG. 3.

In step 315, the relative probability of each candidate model is determined, e.g., the normalized probability $P(M_k|y)$ is determined using Equation 1b (repeated below)

$$P(M_k|y)=P(M_k|y)/\{\Sigma_{j=1,K}P(M_j|y)\}, \tag{1b}$$

based on $P(y|M_k)$, the marginal likelihood of the data given the model determined in step 310, and the proportionality described in Equation 1a (repeated below).

$$P(M_k|y) = \frac{P(y|M_k)P(M_k)}{P(y)} \propto P(y|M_k) \tag{1a}$$

In step 317, it is determined whether heterogeneity in the data y is small enough to be acceptable for purposes of the analysis. If not, then in step 319 the data y is split into two or more subsets y* to be processed separately, and control passes back to step 307, described above, to process each subset. Examples of heterogeneity in simulated and experimental MSD data are described in more detail in a later section. In MSD data, heterogeneity in type of motion either along a single trajectory or between multiple observed trajectories (due, for example, to cell-to-cell variation or a biological process that varies over time or space within the same cell) requires classification of the trajectories into smaller, less heterogeneous subsets. Such classification can be important to understanding biological mechanism, for example when distinct modes of motion are resolved as a function of cell cycle stage or sub-cellular location. Splitting the observed dataset into smaller sets of particles, however, typically comes at the cost of increasing noise in the mean MSD curve because each sub-group has fewer trajectories to average across.

In step 321, it is determined whether the noise in a data set y or subset y* is small enough to be acceptable for purposes of the analysis. As shown in examples described in later sections, the more complete model is likely to be discovered by this analysis in data sets with the lowest possible noise. If the noise is not acceptable, then control passes back to step 305, described above, to obtain more data and reprocess the expanded data set. Reduction of experimental noise in MSD data can be achieved by increasing the sampling rate or collecting longer or more trajectories. [?Can we say this: In some embodiments, the amount of data obtained is increased by a certain amount, e.g., doubled, until a predetermined number of successive increases (e.g., two doublings) does not change the favored model, to determine a reasonably robust model of the system. In some embodiments, the system is perturbed slightly, e.g., by introducing a mutation or new non-fluorescent component; and, if the perturbation does not change the favored model, it is determined that a reasonably robust model of the system has been deduced.

In step 323, one or more models are selected based on the corresponding relative probabilities, such as the normalized probabilities $P(M_k|y)$ for each model. In some embodiments, a single most probable model is selected. In some embodiments, several models with probabilities above some threshold are selected.

In some embodiments, the extent to which data support one model $M_j$ over another model $M_k$ is measured by the ratio of the data marginal likelihood given by one model to another, namely the ratio of the posterior odds of $M_j$ over its prior odds, which is also called the Bayes factor (BF), as given by Equation 15.

$$BF_{jk}=P(y|M_j)/P(y|M_k)=\{P(M_j|y)/P(M_k|y)\}/\{P(M_j)/P(M_k)\} \tag{15}$$

When model priors are equal, the Bayes factor is equal to the posterior odds of $M_j$ against $M_k$. Thus $BF_{jk}>1$ indicates model j is preferred over model k; and $BF_{jk}<1$ indicates model k is preferred over model j. While calculation of the posterior model probabilities and Bayes Factors is purely objective in the Bayesian framework, model selection is subjective because the actual evidence for choosing one model over another depends on the degree of belief or uncertainty that one attributes to relative model probabilities. The following thresholds have been proposed for interpreting $BF_{jk}$. When $1 \leq BF_{jk} \leq 3$, there is evidence for $M_j$, but it is "not worth more than a bare mention," when $3 \leq BF_{jk} \leq 10$ the evidence is positive, when $10 \leq BF_{jk} \leq 100$ it is strong, and when $100 < BF_{jk}$ the evidence is decisive. (See Jeffreys, H. *Theory of Probability*, Oxford University Press, Oxford, England, 1961.)

The Bayesian information criterion (BIC) is a special case of the Laplace approximation assuming a normal prior with the mean at $\beta_{post}$ and covariance equal to the inverse of the expected Fisher information matrix of the parameter for one observation, namely the unit information prior (see Kass, R. E., and L. Wasserman, "A Reference Bayesian Test For Nested Hypotheses And Its Relationship To The Schwarz Criterion," *J. Am. Stat. Assoc.*, v90, pp 928-934, 1995). The BIC for the model $M_j$ is given by Equation 16a.

$$BIC_j = -2 \log P(y|M_j) + p \log n \quad (16a)$$

where p is the number of parameter in $M_j$ and n is the number of data points in y. When n is large, the log of the Bayes factor ($BF_{jk}$) of $M_j$ against $M_k$ can be approximated by Equation 16b.

$$\log BF_{jk} = -\tfrac{1}{2}(BIC_j - BIC_k) \quad (16b)$$

regardless the choice of the parameter prior, which is called the Schwarz criterion. The normalized model probabilities can then be computed from all $BF_{jk}$ subjected to the normalization constraint given by Equation 16c.

$$\Sigma_{k=1,d} P(M_k|y) = 1 \quad (16c)$$

In step 325, the values for one or more parameters are determined for the selected models. In some embodiments, a single most probable model is selected in step 323 and the values of the parameters are given by $\beta_{post}$ determined in step 505 for the selected model. In some embodiments, several models with probabilities above some threshold are selected, and the values for the one or more parameters is an average of those parameter values $\beta_{post}$ for each of the selected models weighted by the relative probability of that model, such as normalized probability $P(M_k|y)$. Once the motion model has been established using multiple hypothesis testing, the parameter values associated with the model may be interpreted. Evaluation of the parameter values as a function of model probability shows that when model probability is high the parameter values are well estimated, whereas their values become poorly estimated when the probability is low. Thus, the Bayesian hypothesis testing framework provides a pre-screening filter for the downstream interpretation of model parameter values, which are only reliable when the probability of the model to which they belong is also sufficiently favorable. In some embodiments, a parameter estimate is considered reliable when the model probability is greater than about 0.7 and preferably greater than about 0.9.

In some embodiments step 325 includes determining a biological interpretation of the selected model and parameter values, as described in more detail in later sections with reference to FIG. 14 through FIG. 17C. In order to eliminate heterogeneity from biological samples, classification into less-heterogeneous subgroups is commonly used. The criterion used for this classification must be appropriately chosen to reduce heterogeneity. In practice, an appropriate criterion will not be known a priori, and one or more biological coordinates along which to classify the data are hypothesized. We suggest (and illustrate in the below applications) that initially all particle trajectories should be analyzed together, then the trajectories should be split into two groups along a hypothesized coordinate; and re-analyzed to look for significant differences in preferred model or parameter values between the two groups. Such differences would suggest biologically relevant variation along the chosen coordinate, which can be further explored by repeatedly sub-dividing the trajectories into smaller sub-groups. However, it is important to keep in mind that while classification into appropriate subgroups will reduce heterogeneity in motion models and/or parameter values, allowing resolution of distinct types of physical motion present in the biological system, it will also typically reduce the number of individual-particle MSDs available per sub-group, effectively increasing the level of experimental noise in the mean MSD curve. Thus, while classification is very important to the investigation of biological mechanism underlying single particle motion, in practice additional data acquisition will likely be required to resolve more complex models as the level of classification increases.

In step 327, it is determined whether prior probabilities of values for one or more parameters of one or more model are to be updated based on the selected models or biological interpretations performed during step 325. If so, then determination of prior probabilities of parameter values in step 311 is modified to include the updated probabilities, e.g., step 507 is modified to retrieve stored distributions of parameter values. Otherwise the analysis for the data obtained in step 305 is complete.

3. Example FCS Embodiments

According to various embodiments, methods are demonstrated for analysis of FCS data sensitive to particle motion in living tissue, which shows the advantages of various options for implementation. In some embodiments, FCS TACF curves are simulated. In some embodiments, experimental TACF curves for living tissue are used.

3.1 Simulated FCS Data

To illustrate application of the techniques to FCS, TACF curves were simulated from a single physical model with uniform, independent, additive Gaussian noise, and various cases of non-uniform noise and correlated noise were considered. Uniform noise is typical of TACF curves computed in image correlation spectroscopy (ICS) where the sampling time is fixed over $\tau_i$. The simulated TACF is then given by, $G^{sim}(\tau_i) = G^{th}(\tau_i) + \epsilon_i$, where $G^{th}$ is the theoretical TACF specified, for example, by Equation 4b for pure diffusion, $\tau_i$ is the sampled lag time, and $\epsilon_i$ is the normally distributed noise term with zero mean and standard deviation $\sigma$, indicated by $\epsilon_i = N(0, \sigma^2)$. The lag time $\tau_i$ is spaced uniformly on a log-scale with minimum time interval of $10^{-6}$ seconds (s), spanning a total time period of $10^3$ s. Calculation of the values at each sampled time point is implemented in MATLAB; and $\epsilon_i$ is generated using the MATLAB function randn as $\epsilon_i = \sigma * \text{randn}$.

In one set of embodiments, simulated TACFs were generated from the two-component pure diffusion model with varying degrees of added noise. For fixed ratio of diffusion coefficients $D_2/D_1 = 5$ and equal value of a (relative brightness of two fluorescent components), the two-component model is preferred over the one-component model for low noise levels ($\sigma/G_0 < 1\%$). Thus, 1% relative noise is determined to be a good threshold in order to have confidence that a reasonably complete model has been determined for $D_2/D_1$ greater than or equal to about 5. In general, if relative noise is less than about 1%, the model is reasonably most justified. As the relative noise level increases beyond approximately 1%, however, the one-component model probability increases monotonically until it eventually become comparable to the two-component model probability near $\sigma/G_0 \approx 1\%$, and eventually dominates near $\sigma/G_0 \approx 10\%$, indicating preference for this simpler model (P>95%). Thus, the Bayesian approach naturally prefers the simpler model when the signal-to-noise ratio in the TACF is low, with this crossover depending on the number of data points in the sample. A larger number of data points allows for proper model discrimination despite higher noise. In other words, the Bayesian approach prefers the more complex model only when the quality and amount of data are sufficient to justify the added complexity. Importantly, probability of the three-component model remains near zero for all levels of noise, demonstrating that the procedure also does not over-fit the TACF data.

Parameter estimates from the one- and two-component models show that the diffusion coefficients obtained from the two-component model begin to diverge when the probability of this model decreases to zero, whereas the inferred amplitudes or mean particle numbers are more robust to the noise. Thus, model probability may be used as a measure of reliability of underlying parameter estimates obtained for a given model. Thus, a model probability of 90% is determined to be a good threshold in order to have confidence that a reasonable value for a model parameters has been determined. If model probability is greater than about 90%, then the model parameters are reasonably accurate.

For a fixed level of noise and equal the two-component model is preferred to the one-component model when the difference between $D_1$ and $D_2$ is large, because the two species may then be distinguished in the TACF. In contrast, in the intermediate regime when $D_1/D_2 \approx 1$, the techniques presented here prefer the simpler one-component model because the two components cannot be distinguished, and the range of this regime narrows with decreasing noise. Thus, the selection procedure of the presented approach again, naturally penalizes overly complex models when the resolution in the data does not allow for the underlying physical process to be distinguished.

For TACFs with varying values of $a_1/a_2$ but a fixed noise level and value for $D_1/D_2$, the presented approach exhibits a similar behavior to the case of varying $D_1/D_2$. The two-component model is preferred when the amplitudes of the two components are similar ($a_1/a_2 \approx 1$), while the one-component model is preferred when $a_1/a_2$ is considerably different from 1 and the contribution from one of the species is too small to be detected. The regime where the two-component model is preferred becomes narrower when $D_1$ and $D_2$ are less separated. Again, this demonstrates that the ability of the presented approach to distinguish the underlying physical process depends on the resolution of the data.

Similar model selection properties to those above are observed when fitting TACFs with non-uniform noise, which results when auto-correlations are computed using a multi-tau hardware correlator. Correlated noise can be handled by using the more general noise model Eq. 13a to calculated model probabilities. Ignoring the noise correlations over-fits the overly complex model when the correlation in the noise is strong, while over-fitting is not observed when the covariance matrix of the noise is incorporated into fitting. This important observation is addressed in detail when the TACF curves are computed from underlying fluorescence intensity traces.

To illustrate the extension of the presented approach to additional physical processes, models of convection and mixed diffusion-convection were include in the fitting process. As above, the presented approach correctly identifies the two-component diffusion model as the true physical process at low noise. However, as the relative noise level increases, the probability of the one-component diffusion model again increases to nearly one before the probability of the pure convection model increases to compete with the one-component diffusion model at high noise. In this high-noise regime, the presented approach finds distinguishing between the two simplest models is not justified by the data; and, therefore the presented approach does not prefer one over the other because they have equal complexity (i.e., two fitting parameters).

Differences in the range of the prior probabilities $P(\beta|M_k)$ of the parameters given the model affects the model probabilities slightly but it does not alter the relative ranking of the models. Again, the presented approach does not over-fit the TACF, as determined by the fact that the probabilities of models of greater complexity remain near zero for all levels of noise. The foregoing well-established feature of the presented approach that allows for the simultaneous evaluation of non-nested competing hypotheses is an important distinction from conventional frequentist hypothesis tests.

Switching the "true" underlying physical process (i.e., the model used to generate the $G^{th}(\tau)$ TACF curve) from two-component diffusion to one-component diffusion with convection results in a similar pattern of model selection as a function of noise. When diffusion is dominant (Peclet number, Pe=0.1, where Pe=$w_0 v/D$, and relates the relative importance of convection to diffusion), The presented approach correctly distinguishes the diffusion-convection model at low noise, until first the simpler one-component pure diffusion model competes with the true model at intermediate levels of noise, and then the one-component pure diffusion and pure convection models compete at high noise because of their identical model complexity. The same trend is observed when convection is dominant (Pe=10): The pure convection model is preferred at intermediate noise levels until one-component pure diffusion becomes indistinguishable from pure convection at high noise.

Exploring a broad range of Peclet numbers results in similar model selection behavior as that observed in the preceding pure two-component diffusion model analyses. Namely, for the well distinguished physical regimes of Pe>1 and Pe<1, the presented approach clearly prefers the simpler pure one-component diffusion and convection, respectively, whereas in the intermediate regime Pe≈1, the presented approach selects the more complex, true physical process of diffusion-convection, where the width of this intermediate regime broadens with decreasing noise level. As before, over-fitting is naturally avoided, as demonstrated by a negligible probability for a model with two diffusion components plus convection.

The performance of the presented approach was also tested when the "true" physical process is not amongst the possible set of models considered in the data fitting and model inference process. Of course, this is the most common scenario in reality because all models are "wrong" in the sense that each is a mere approximations to reality. However, despite the fact that all models are "wrong," some models are useful; and, the aim of the presented approach is precisely to determine which of a set of competing models is best justified according to the Principle of Parsimony to describe the observed data given the relative model complexities. To investigate this scenario, the two-component diffusion model is again used to simulate the TACF but this model is excluded from the fitting process. For low noise, the presented approach prefers the more complex, three-component model to the simpler, one-component model; whereas, for high noise, model preferences are reversed. This reversal occurs at increasingly higher noise levels as the ratio of $D_2/D_1$ is increased. Interestingly, this cross-over occurs at a lower noise level than in the one diffusion component model, presumably because the over-fitting (three-component) model is penalized more than the "true" model due to the three component model having relatively higher complexity.

In further simulations, fluorescent particle diffusion is simulated using Brownian Dynamics. The photo-physics of fluorescence excitation, emission, and light collection from a confocal volume is implemented according to Wohland, T., R. Rigler, and H. Vogel, "The standard deviation in fluorescence correlation spectroscopy," *Biophysical Journal* v80, pp 2987-2999, 2001. Briefly, diffusion of a fixed number of particles N=69, corresponding to approximately 1 nanoMole (nM, 1 nM=10-12 Moles) concentration is simulated using a random walk in a sphere of 3 micron radius. A new particle is randomly placed on the surface of the sphere when a particle moves out of the sphere. The step size of the random walk in each Cartesian coordinate direction (indicated by index i, i=1, 2, 3) is given by Equation 17a.

$$\Delta x_i = [\sqrt{(2D\Delta t)}] * \xi \qquad (17a)$$

where D is the particle diffusion coefficient, $\xi$ is a normally distributed random number with unit variance and zero mean, and $\Delta t$ is the size of the time-step. For the illustrated embodiments $\Delta t=0.2$ microseconds ($\mu s$, 1 $\mu s=10^{-6}$ seconds). Fluorescence excitation by a microscope objective of 63× magnification and 1.2 numerical aperture (NA) is simulated assuming a Gaussian Laser Beam (GLB) profile (see Siegman, A. E., *Lasers*, University Science Books, Mill Valley, Calif., 1986), with laser power P=100 microWatts ($\mu W$, 1 $\mu W=10^{-6}$ Watts) and wavelength $\lambda=514.5$ nanometers (nm, 1 nm=$10^{-9}$ meters), and characteristic beam width=261 microns. Fluorescence emission is simulated accounting for the actual position of the particle in the focal volume, its absorption cross-section $\sigma_{abs}=2.2\times10^{-20}$ m$^2$, and fluorescence quantum yield $q_f=0.98$. The emission photon count $N_e$ for a particle at a spatial coordinate (r,z) from the center of the sphere is thus given by Equation 17b.

$$Ne = I(r,z)/e_{phot} * \sigma_{abs} * \Delta t * q_f, \qquad (17b)$$

where I(r,z) is the GLB profile in cylindrical coordinates and $e_{phot}$ is the energy of one photon at the emission wavelength $\lambda$. Effects of photobleaching, saturation, and the triplet state of the fluorophore are ignored in the current simulation.

The mean number of collected photons from a particle depends on the Collection Efficiency Function (CEF) of the pinhole of the confocal microscope system as expressed in Equation 17c.

$$\langle N_D \rangle = \kappa * N_e * CEF(r,z) * q_D + N_{bg} \qquad (17c)$$

where $N_{bg}$ is a constant representing the ambient light, $q_D$ is the quantum yield of the detector and $\kappa$ is optical transmittance. CEF(r,z) for a pinhole with diameter of 50 microns is calculated by numerical integration according to Rigler, R., U. Mets, J. Widengren, and P. Kask, "Fluorescence Correlation Spectroscopy with high count rate and low background: analysis of translational diffusion," *European Biophysics Journal with Biophysics Letters*, v22, pp 169-175, 1993. For all TACF simulations presented below, $\kappa=0.01$, q=0.25 and $N_{bg}=0$, unless otherwise specified. The confocal volume, given by focal plane diameter $w_0$ and focal depth $z_0$, or MDF, are obtained by fitting a 3 dimensional Gaussian function to the resulting MDF, which is given by Equation 17d.

$$MDF(r,z) = CEF(r,z) * I(r,z) \qquad (17d)$$

The simulation is implemented in MATLAB using the Poisson random number generator Poisson( ) to simulate photon emission with specified mean $\langle N_D \rangle$. TACF curves are computed using the multi-tau algorithm, which has 128 channels recording fluorescence intensities with a quasi-logarithmic scale time increment. For example, the time increment is doubled after the first 16 channels and then doubled every 8 channels. The counts in two adjacent channels are summed before being passed to the next channel with double time increment.

The presented approach was applied to TACF curves computed from simulated fluorescence intensity traces of two species undergoing normal diffusion, in order to test the ability of the approach to detect the two species for varying conditions of acquisition and physical processes typically encountered experimentally. Averages of such simulated TACF data were depicted as data points 206 in FIG. 2A, described above, for 3.3 seconds of simulated data of 34 particles with diffusion coefficient $D_1=63.1$ $\mu m^2/s$ and 35 particles with diffusion coefficient $D_2=121.8$ $\mu m^2/s$. The fits to the average TACF data using single component diffusion model and a two component diffusion model are shown in FIG. 2A; and the normalized residuals are shown in FIG. 2B.

The noise correlation calculated from multiple TACF curves (e.g., as depicted in FIG. 2C, described above, for a similar simulation differing only in $D_1=270$ $\mu m^2/s$ and $D_2=27$ $\mu m^2/s$) has a structure consistent with the expected noise correlation structure for a TACF curve calculated from a multi-tau correlator. At small $\tau$ the noise is dominated by uncorrelated photon counting noise due to the short sampling time $\Delta\tau$ there. As $\Delta\tau$ increases with increasing $\tau$, the photon count increases and the noise becomes dominated by intensity fluctuations from particle motions, which are highly correlated (see region 246a in FIG. 2C) on the time-scale of diffusion in the focal volume. When $\Delta\tau$ is much larger than the diffusion correlation time $\tau_D$, the noise in this regime becomes uncorrelated again because intensity fluctuations are uncorrelated on this time-scale. This corresponds well with correlated errors indicated in FIG. 2B for the middle range of $\tau$.

To investigate systematically the effect of variable experimental noise, which can result from low count rate of the particles or insufficient acquisition time, on the ability of the Bayesian approach to identify the number of components present, the optical transmittance $\kappa$ or the acquisition time T of the photon-count trace was varied and model probabilities were calculated from the resulting TACF curves. The noise levels and correlations in TACFs are estimated using multiple curves as described above in steps 403 through 407 of FIG. 4A.

Figure 7A:
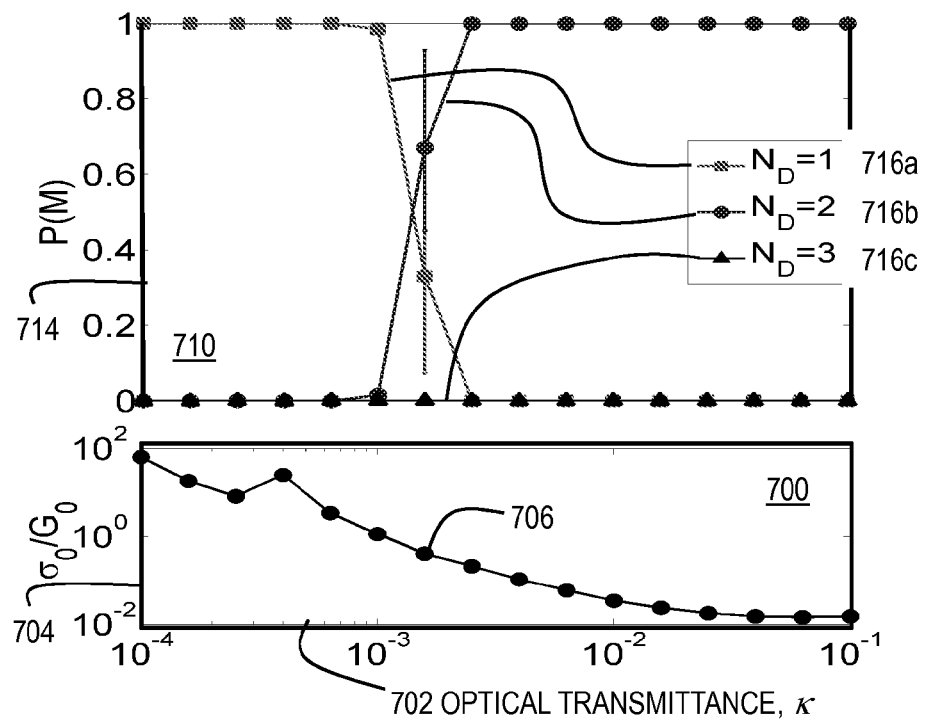
FIG. 7A through FIG. 7E are graphs the illustrate example sensitivity of model selection, according to various embodiments.
Figure 7B:
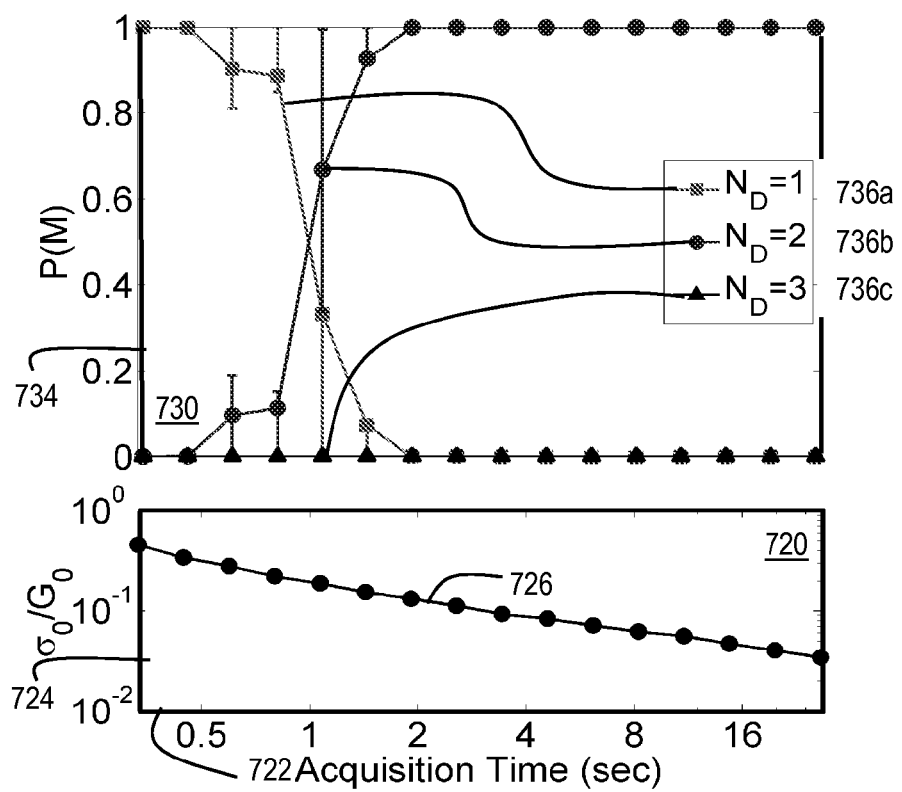

FIG. 7A through FIG. 7E are graphs the illustrate example sensitivity of model selection, according to various embodiments. FIG. 7A includes a pair of graphs 700 and 710 that illustrate example relative noise and model selection as a function of optical transmittance $\kappa$, according to an embodiment The horizontal axis 702 for both graphs indicates optical transmittance, $\kappa$, which is dimensionless. The vertical axis 704 of graph 700 indicates relative noise at zero time lag ($\sigma_0/G_0$), which is also dimensionless. The vertical axis 714 of graph 710 indicates the $P(M_k|y)$, abbreviated P(M), which is the probability of a model $M_k$ given the data y from an embodiment of the presented approach and is dimensionless. The trace 706 indicates the relative noise. The trace 716a indicates the probability of the single component diffusion model ($N_D=1$). The trace 716b indicates the probability of the "true" two component diffusion model ($N_D=2$). The trace 716c indicates the probability of an overly complex three component diffusion model ($N_D$=3). FIG. 7B includes a pair of graphs 720 and 730 that illustrate example relative noise and model selection as a function of acquisition time, according to an embodiment. The horizontal axis 722 for both graphs indicates acquisition time in seconds. The vertical axis 724 of graph 720 indicates relative noise at zero time lag ($\sigma_0/G_0$), which is dimensionless. The vertical axis 734 of graph 730 indicates P(M) from an embodiment of the presented approach and is dimensionless. The trace 726 indicates the relative noise. Trace 736a, trace 736b and trace 736c indicate the probability of the simplified one component diffusion model ($N_D$=1), the "true" two component diffusion model ($N_D$=2) and the overly complex three component diffusion model ($N_D$=3); respectively.

As observed in earlier simulations, the presented approach resolves the "true" two-component model at low noise levels ($<10^{-1}$=10%), corresponding to larger values of optical transmittance or acquisition time, but prefers the less complex one component model when the noise level increases ($>10^{-1}$=10%) because the additional complexity of the two-component model is not justified there given the uncertainty in the TACF data. Importantly, the overly complex three component model is never preferred, demonstrating that the presented approach does not over-fit the data. While the maximum relative noise level that can be tolerated for the presented approach to resolve the two-component model in this simulation is found here to be ~10%, the resolution of the procedure can be improved by increasing the signal-to-noise ratio via longer measurement times, brighter fluorophores, or averaging additional TACFs. Thus, in some embodiments, it is determined to make one or more such adjustments if it is determined that the relative noise≧about 10%.

Figure 7C:
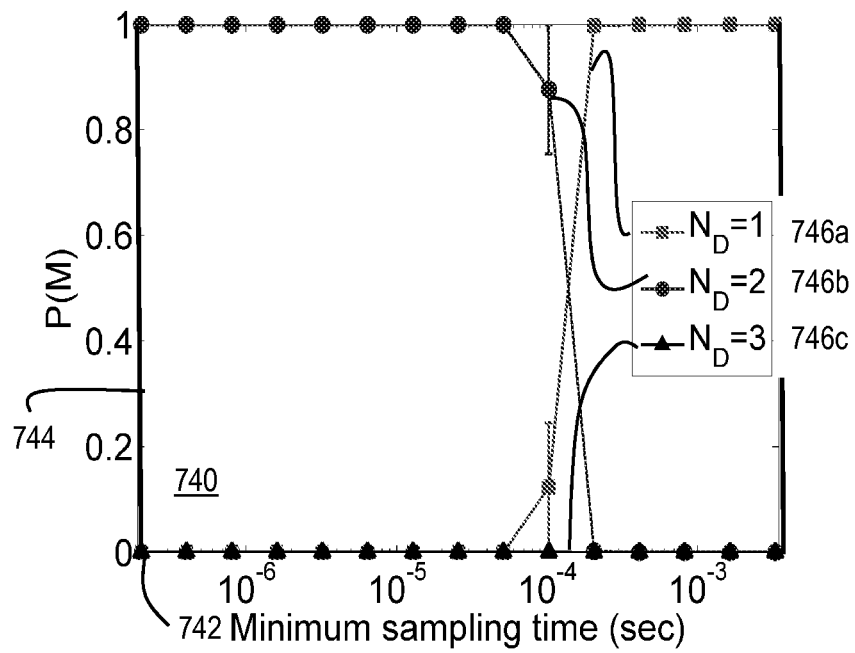

Minimum sampling time is also expected to affect the ability of the presented approach to resolve the two species. When the minimum sampling time exceeds the diffusion time of the fast diffusing component (e.g., 55 µs), then the fast component is no longer apparent in the TACF curve and the presented approach correspondingly prefers the one-component model. FIG. 7C is a graph 740 that illustrates an example dependence of model selection on minimum sampling time, according to an embodiment. The horizontal axis 742 indicates minimum sampling time in seconds; and, the vertical axis 744 indicates P(M) from an embodiment of the presented approach and is dimensionless. Trace 746a, trace 746b and trace 746c indicate the probability of the simplified one component diffusion model ($N_D$=1), the "true" two component diffusion model ($N_D$=2) and the overly complex three component diffusion model ($N_D$=3), respectively. While the sampling time is not generally a concern for single point FCS measurements using APDs or PMTs, limitations in minimum sampling time are of major concern in image-based FCS methods where sampling time is on the scale of milliseconds or longer. Again, the overly complex model is never selected.

Figure 7D:
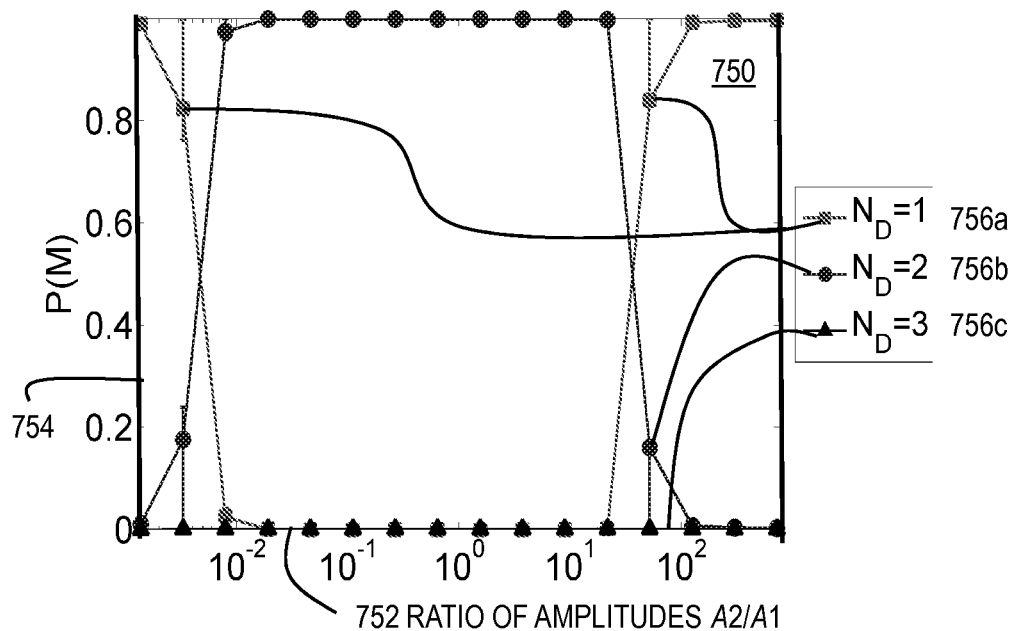

The effect of varying the underlying physical process was examined by varying the relative brightness $B_i$ of the two species, which alters their relative amplitudes $a_2/a_1$. Experimentally, a may vary due to differences either in the brightness or the concentration of the particles examined. FIG. 7D is a graph 750 that illustrates an example dependence of model selection on relative amplitudes of two diffusing species, according to an embodiment. The horizontal axis 752 indicates relative amplitudes $a_2/a_1$, which is dimensionless; and, the vertical axis 754 indicates P(M) from an embodiment of the presented approach and also is dimensionless. Trace 756a, trace 756b and trace 756c indicate the probability of the simplified one component diffusion model ($N_D$=1), the "true" two component diffusion model ($N_D$=2) and the overly complex three component diffusion model ($N_D$=3), respectively. When the amplitudes of the two components are similar ($a_2/a_1$ between about 0.05 and about 20), the presented approach is able to resolve the two species. In contrast, when the relative amplitude of the two components becomes considerably different from unity ($a_2/a_1$ less than about 0.02 or greater than about 50), the contribution to the TACF from one of the species is too small to be detected above the noise so that the presented procedure prefers the simpler, one-component model. Again, the overly complex model is never selected.

Figure 7E:
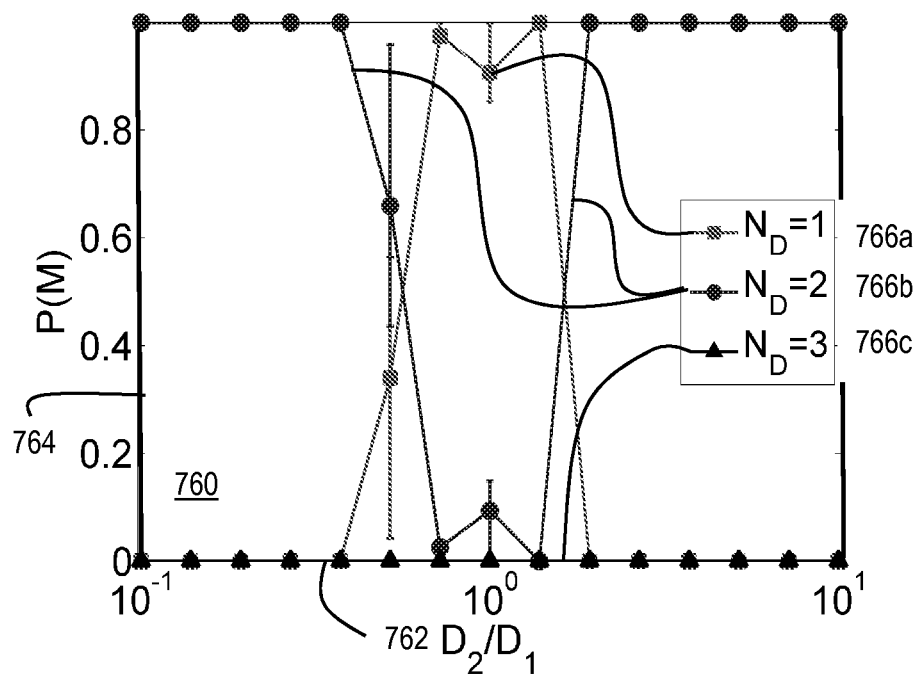

Similar to the effect of varying $a_2/a_1$, the ability of the presented approach to resolve the two species depends on the ratio of their diffusion coefficients $D_2/D_1$. FIG. 7E is a graph 760 that illustrates an example dependence of model selection on relative diffusion coefficients of two diffusing species, according to an embodiment. The horizontal axis 762 indicates relative diffusion coefficients $D_2/D_1$, which is dimensionless; and, the vertical axis 764 indicates P(M) from an embodiment of the presented approach and also is dimensionless. Trace 766a, trace 766b and trace 766c indicate the probability of the simplified one component diffusion model ($N_D$=1), the "true" two component diffusion model ($N_D$=2) and the overly complex three component diffusion model ($N_D$=3), respectively. When $D_2$ and $D_1$ are approximately equal ($D_2/D_1$ between about 0.9 and about 1.1), the simpler one-component model is preferred because the two components cannot be sufficiently resolved due to their similar diffusion time-scales, as indicated for the earlier simulations described above. Outside of this regime (e.g., for $D_2/D_1$ less than about 0.5 or greater than about 2.0), the two-component model is preferred because the diffusion time-scales of the two components are well separated and can be distinguished at the given noise level. Again, the over-parameterized three-component model is never preferred. Note that that the transition in model probabilities at $D_2/D_1>1$ is shaper than the transition at $D_2/D_1<1$. This is expected to be because the value of $D_1$ is smaller in the latter case, and slower diffusion of particles increases the variability in observed TACF curves given a fixed observation time, increasing noise and reducing the ability to resolve complex models.

Figure 7F:
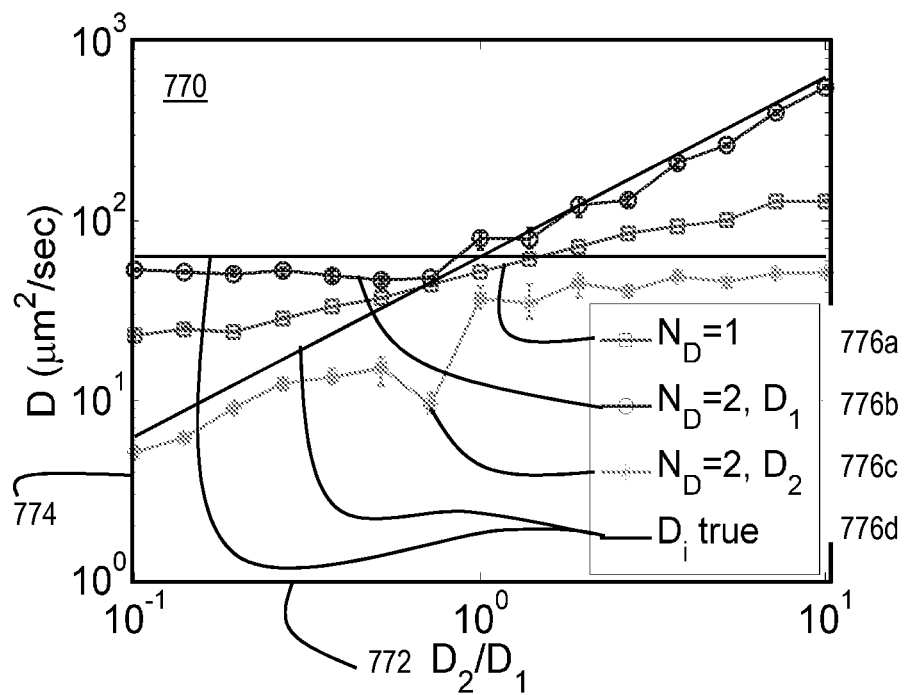
FIG. 7F and FIG. 7G are graphs that illustrate example estimates of model parameter values, according to an embodiment.
Figure 7G:
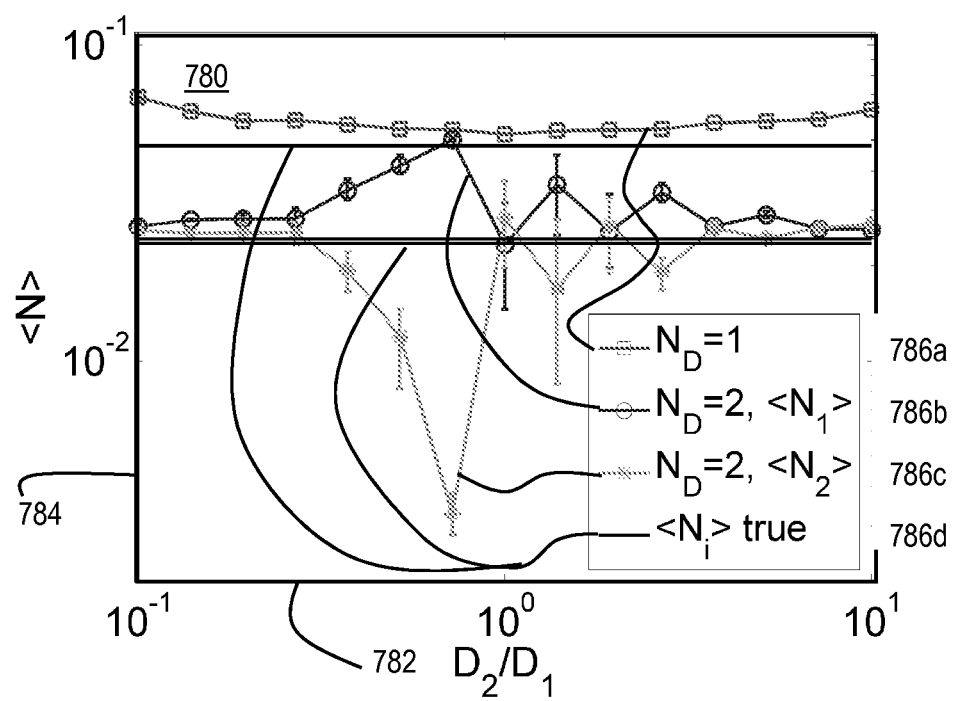

The parameter estimates from the two-component model are reliable when the probability of this model is high, and become less reliable when the model probability is low, with greater uncertainty. FIG. 7F and FIG. 7G are graphs that illustrate example estimates of model parameter values, according to an embodiment. FIG. 7F is a graph 770 that illustrates an example dependence of model parameter diffusion coefficient values on ratio $D_2/D_1$ of diffusions constants, according to an embodiment. The horizontal axis 772 indicates ratio $D_2/D_1$ of diffusions constants, which is dimensionless; and, the vertical axis 774 indicates a value of diffusion coefficient in µm²/s. Trace 776a indicates the estimated value of the diffusion coefficient for the one component diffusion model. Trace 776b, and trace 776c indicate the estimated values for the two diffusion coefficients $D_1$ and $D_2$,a respectively, for the two component diffusion model, in which the larger diffusion coefficient is always associated with component 1 and, thus, is labeled $D_1$. The two traces labeled 776d indicate the "true" values for the two diffusion coefficients $D_1$ and $D_2$, respectively. One stays constant, while the other varies from less than that value to greater than that value. Where the model probability is high at ratios less than 0.5 or greater than about 2, for the two component model, the values of $D_1$ and $D_2$ approach the two true values ($D_1$ always referring to the larger value), and the value of the low probability one component model takes on an intermediate value. Where the model probability is low, at ratios between about 0.9 and 1.1, for the two component model, the value of $D_2$ diverges from the two true values, and the value of the high probability one component model takes on value close to the "true" value.

FIG. 7G is a graph 780 that illustrates an example dependence of model parameter indicating the number diffusing particles on the ratio $D_2/D_1$ of diffusions constants, according to an embodiment. The horizontal axis 782 indicates ratio $D_2/D_1$ of diffusions constants, which is dimensionless; and, the vertical axis 784 indicates a value of $\langle N \rangle$, the mean number of diffusing particles. Trace 786a indicates the estimated value of $\langle N \rangle$ for the one component diffusion model. Trace 786b and trace 786c indicate the estimated values for the two constants $\langle N \rangle_1$ and $\langle N \rangle_2$, respectively, for the two component diffusion model. The two traces labeled 786d indicate the "true" values for the two constants $\langle N \rangle_1$ and $\langle N \rangle_2$, respectively. Where the model probability is high at ratios less than 0.5 or greater than about 2, for the two component model, the values of $\langle N \rangle_1$ and $\langle N \rangle_2$ approach the two true values, and the value of the low probability one component model takes on a value near a sum of the two separate values. Where the model probability is low, at ratios between about 0.9 and 1.1, for the two component model, the value of $\langle N \rangle_2$ diverges from the two true values, and the value of the high probability one component model takes on value close to the "true" $\langle N \rangle_1$ value.

The estimated values of the diffusion coefficients are better predicted than the mean particle numbers when the two-component model probability is low because the system becomes effectively one-component when $D_2/D_1=1$. In this regime, $D_1$ and $D_2$ in the model need to be close to the overall effective diffusion coefficient, whereas the amplitudes $a_1$ and $a_2$, that depend on $\langle N \rangle_1$ and $\langle N \rangle_2$, respectively, need only to satisfy the constraint $a_1+a_2=a_T$, where $a_T$ is the overall amplitude. As a general rule, these results suggest that parameter estimates from a complex model should only be interpreted when this model is preferred decisively by the model selection portion of the presented approach.

TACFs were calculated from individual simulated intensity traces with varying simulation parameters and analyzed using the block-transformation to estimate the noise levels and correlations described above with reference to step 411 to step 419 in FIG. 4A. TACFs are simulated with optical transmittance $\kappa=0.01$, and background noise $N_{bg}=0.001$. The sensitivity of model selection and parameter determination are compared to those found previously using multiple TACFs to estimate noise correlation. For fair comparison, each individual intensity trace used to calculate the TACFs here has the same simulation time as each intensity trace used to calculate the mean TACFs for FIG. 7A through FIG. 7G.

Figure 8A:
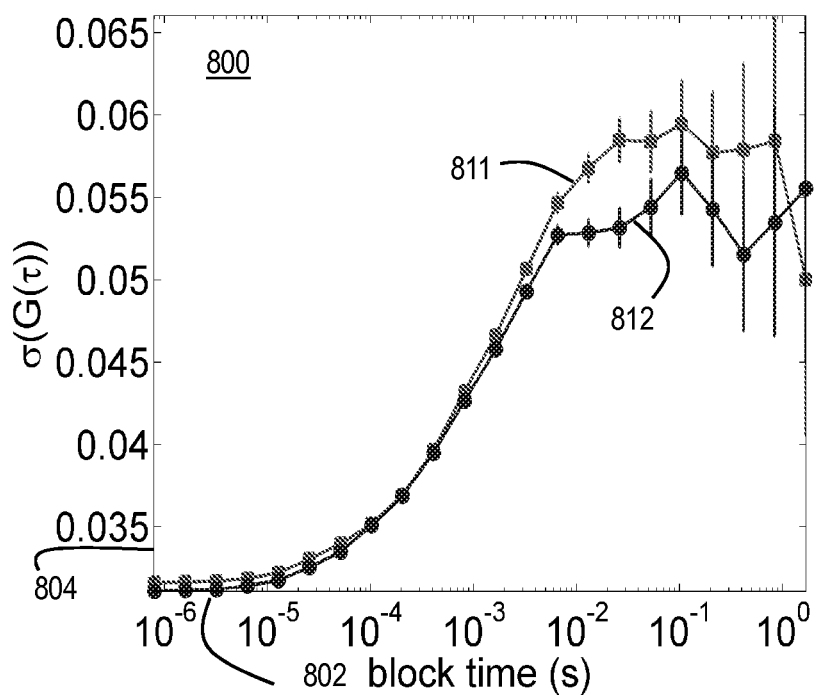
FIG. 8A through FIG. 8B are graphs that illustrate an example method based on blocking intensity observations to estimate noise correlation, according to an embodiment; (FCS II FIG. 4A-4B)
Figure 8B:
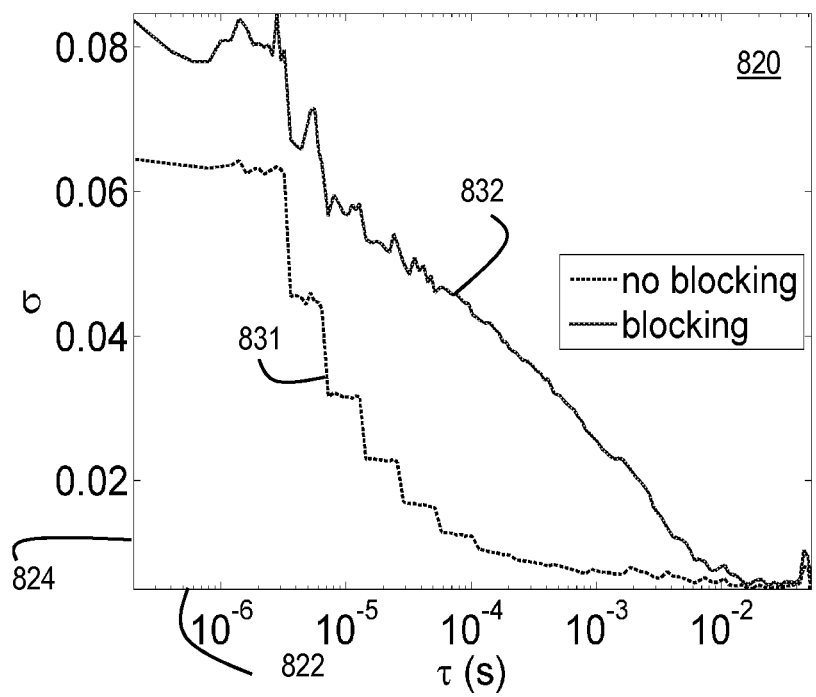

In practice, the optimal block-time can be determined by seeking the first point (fixed point) at which the noise estimate is invariant (within statistical error) to the increase of $t_b$. FIG. 8A through FIG. 8B are graphs that illustrate an example method based on blocking intensity observations to estimate noise correlation, according to an embodiment. FIG. 8A is a graph 800 that illustrates example noise level variation with selection of a block time $t_b$, according to an embodiment. The horizontal axis 802 is block time in seconds; and the vertical axis is noise level in the $G(\tau)$ at a single time lag $\tau$, which is dimensionless. Trace 811 indicates the noise level at time lag $\tau=10^{-5}$ seconds for one TACF; and, trace 812 indicates the noise level at the same time lag for a different TACF. The fixed point is reached after a block time greater than about 20 ms for both traces, which indicates that a block time of this amount or greater is sufficient to obtain independent estimates of noise. The effect of the block time is demonstrated in FIG. 8B. FIG. 8B is a graph 820 that illustrates example effect of blocking on estimates of noise level. The horizontal axis 822 indicates time lag r in seconds; the vertical axis 824 indicates the estimated noise level in $G(\tau)$, which is dimensionless. Trace 831 indicates the noise level estimates as a function of time lag $\tau$ without blocking; Trace 832 indicates the noise level estimates as a function of time lag $\tau$ with blocking using a blocking time $t_b$ of 26.4 milliseconds (ms, 1 ms=$10^{-3}$ seconds). The noise level is uniformly higher with blocking, indicating that the absences of blocking systematically underestimates the noise level.

The use of multiple TACFs to estimate noise correlation (step 403 to step 407) and the use of individual TACFs with blocking to estimate noise correlation (step 411 to step 419) exhibit similar behaviors in terms of model probabilities and parameter estimates when data with equal simulation times are analyzed. Because the number of photon-count products available for estimating the covariance matrix C depends on the length of the photon-count trace, large uncertainty of model probabilities can occur as a result of worse estimates of C as the acquisition time decreases.

It was also determined whether the choice of uniform prior box probability range in step 507, described above with respect to FIG. 5, may affect the model probability computed. As used here, box probability is a uniform probability normalized to 1 over the range in one two or three dimensions. It was found that, if the uniform prior range is sufficiently large, the computed model probabilities are not sensitive to the uniform prior range. FIG. 9A through FIG. 9F are graphs that illustrate an example dependence on the form of the prior probabilities, according to various embodiments.

Figure 9A:
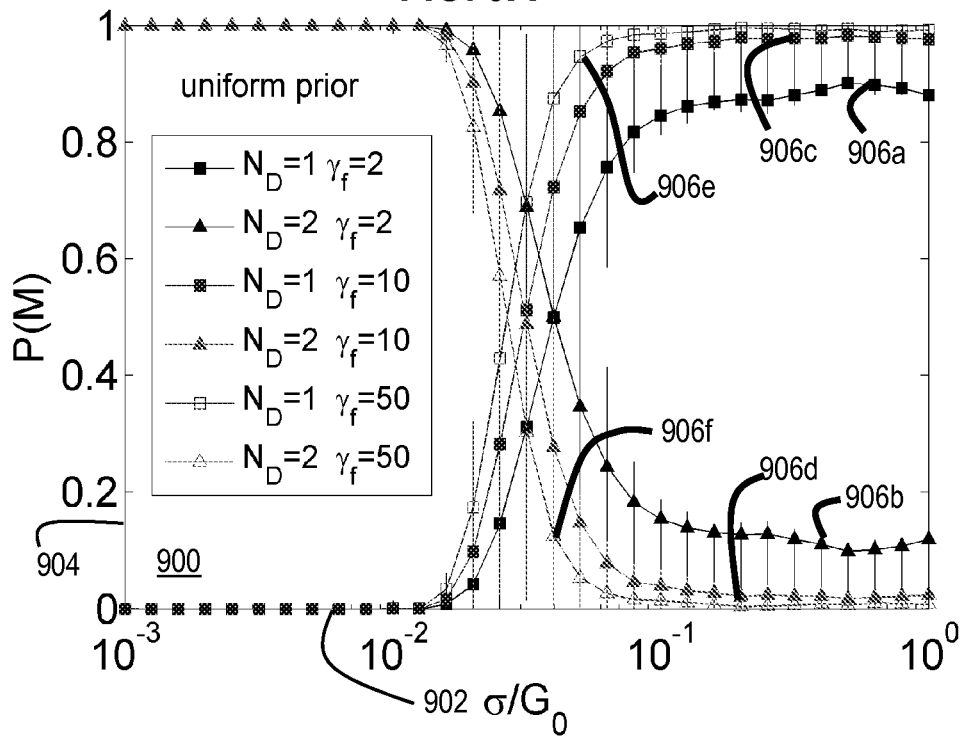
FIG. 9A through FIG. 9F are graphs that illustrate an example dependence on the form of the prior probabilities, according to various embodiments.

FIG. 9A is a graph 900 that illustrates example effect of range of box probability on relative model probabilities, abbreviated P(M), according to an embodiment. The horizontal axis 902 is relative noise; and the vertical axis 904 is P(M). The simulated data is for two-component diffusion with $D_2/D_1=5$ and $a_2/a_1=1$ and uniform noise with relative error ($\sigma_0/G_0$) varied, but computed with different prior box probability ranges. In these embodiments, the uniform prior box size in each dimension is $2\gamma_f\sigma_\beta$. The different box ranges are labeled by the range factor $\gamma_f$. Traces 906a, 906c and 906e indicates the P(M) for a one component diffusion model with range factor 2, 10 and 50, respectively. Trace 906b, 906d and 906f indicates the P(M) for a two component diffusion model with range factor 2, and 50, respectively.

Figure 9B:
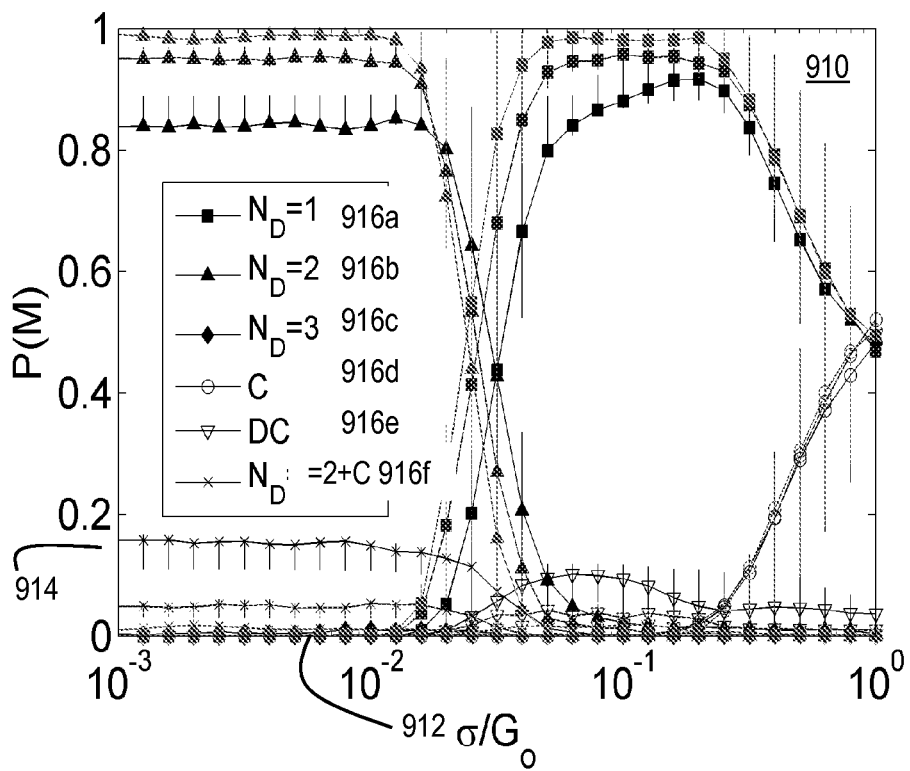

FIG. 9B is a graph 910 that illustrates example effect of range of box probability on relative model probabilities, abbreviated P(M), according to an embodiment. The horizontal axis 912 is relative noise; and the vertical axis 914 is P(M). The simulated data is the same as for FIG. 9A, but computed with different prior box probability ranges (range factor $\gamma_f$ of 10, 40 and 200) and including more complex models. Traces 916a (solid squares) indicate the P(M) for a one component diffusion model is favored near a 10% relative error, with range factors 10, 40 and 200, respectively, providing successively larger probabilities there. Traces 916b (solid triangles) indicate the P(M) for a two component diffusion model is favored at a 1% relative error and below, with range factors 10, 40 and 200, respectively, providing successively larger probabilities there. Traces 916c (solid diamonds) indicate the P(M) for a three component diffusion model is never favored and never even achieves a noticeable probability, with little change for range factors 10, 40 and 200. Traces 916d (open circles) indicate the P(M) for a simple convection model is never favored and never even achieves a noticeable probability, with little change for range factors 10, 40 and 200. Traces 916e (open downward triangles) indicate the P(M) for a one component diffusion with convection model is never favored and achieves a noticeable probability only near a 10% relative error, with range factors 10, 40 and 200, respectively, providing successively smaller probabilities there. Traces 916f (crosses) indicate the P(M) for a two component diffusion with convection model is never favored and achieves a noticeable probability only below a 1% relative error, with range factors 10, 40 and 200, respectively, providing successively smaller probabilities there.

The penalty for the more complex models at higher noise level is not as strong for smaller range factors. As for larger range factor $\gamma_f$=10 and 50, complex models have much lower probabilities at high noise level, but the difference between them is very small.

Figure 9C:
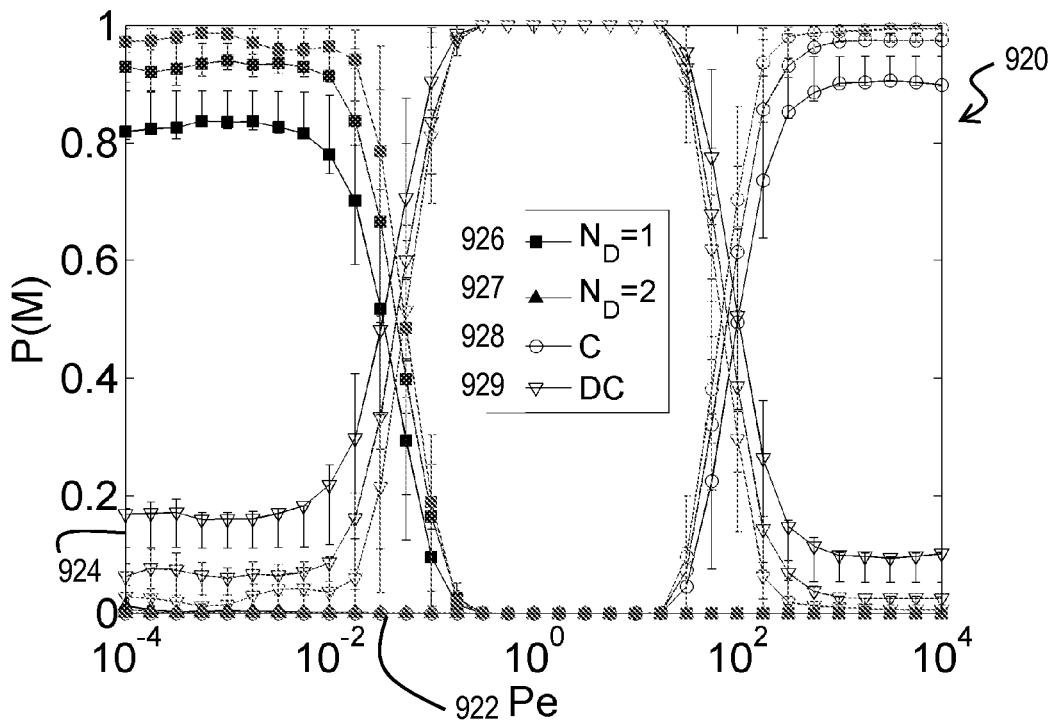

FIG. 9C is a graph 920 that illustrates example effect of range of box probability on relative model probabilities, abbreviated P(M), according to another embodiment. The horizontal axis 922 is dimensionless Peclet number Pe that increases in value with increased importance of convection; and the vertical axis 924 is P(M). The simulated data is for one component diffusion and varying convention speeds v to provide the Pe range from $10^{-4}$ to $10^4$, and uniform noise with relative error ($\sigma_0/G_0$) at 1%, but computed with different prior box probability ranges. Traces 926 (solid squares) indicate the P(M) for a one component diffusion model is favored at Pe values below about $10^{-2}$, where diffusion is dominant with range factors 10, 40 and 200, respectively, providing successively larger probabilities there. Traces 927 (solid triangles) indicate the P(M) for a two component diffusion model is never favored and never even achieves a noticeable probability, with range factors 10, 40 and 200, respectively, providing no noticeable effect. Traces 928 (open circles) indicate the P(M) for a pure convection model is favored above Pe values of about 100, with range factors 10, 40 and 200, respectively, providing successively larger probabilities there. Traces 929 (open downward triangles) indicate the P(M) for a mixed one component diffusion with convection model is favored in a middle range of Pe values from about 0.1 to about 10, with range factors 10, 40 and 200, respectively, providing successively larger probabilities there. in spite of this wide range of range factors, the uniform prior probabilities for parameter values given a model appear to be useful to properly rank candidate models, especially for range factors of about 20 or more.

Note that in all the embodiments illustrated, model ranking is never changed by the uniform prior range.

Figure 9D:
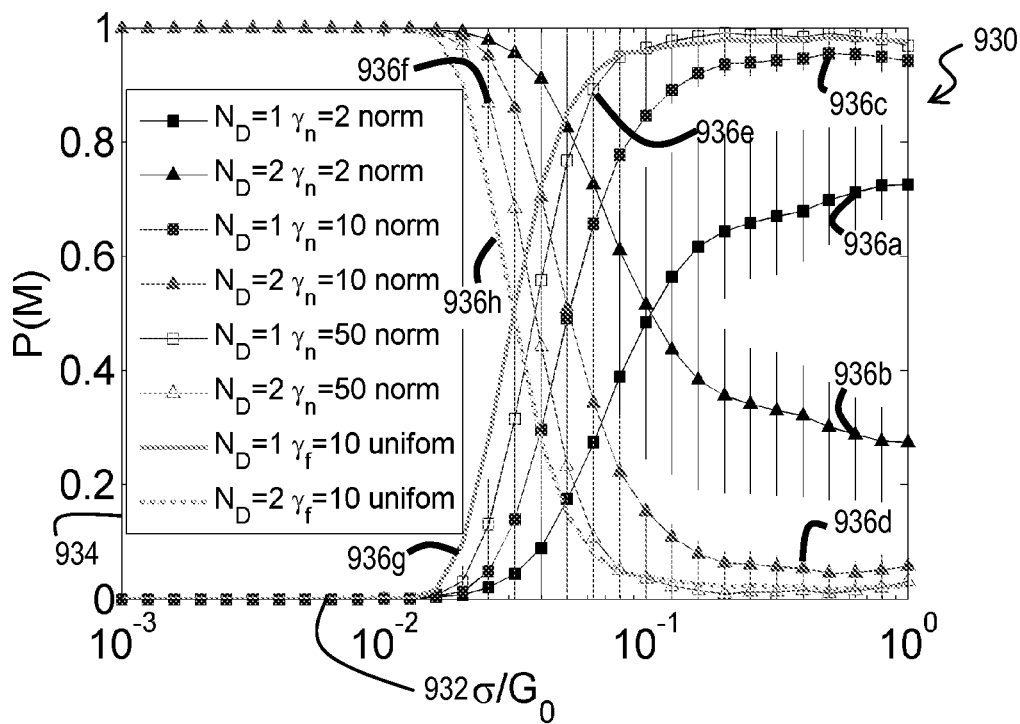

Non-uniform prior may also give different model probability. Here as an example, multivariate normal prior centered at ML estimate is used, as given in Equation 18a.

$$P(\beta) = \frac{1}{(2\pi)^{p/2}\sqrt{\det(\Sigma_{prior})}} \exp\left(-\frac{(\beta-\hat{\beta}_{MLE})^T \Sigma_{prior}^{-1} (\beta-\hat{\beta}_{MLE})}{2}\right) \quad (18a)$$

where $\Sigma_{prior}$ is given by chosen by Equation 18b $$\Sigma_{prior} = \gamma_n^2 \Sigma_\beta \quad (18b)$$

and $\gamma_n$ is the normal range factor. FIG. 9D is a graph 930 that illustrates example effect of normally distributed prior probabilities of parameter values on model probabilities, according to an embodiment. The horizontal axis 932 indicates relative noise; and the verticla axis 934 indicated model probability. The simulated data is for two-component diffusion with $D_2/D_1$=5 and $a_2$=$a_1$=0.5 and uniform noise with relative error ($\sigma_0/G_0$) varied, but computed with different prior normal probability ranges. Trace 936a, trace 936c, trace 936e indicate a one component diffusion model with normal range factors of 2, 10 and 50, respectively. For comparison, trace 936g indicates the same model with a uniform range factor of 10. Trace 936b, trace 936d, trace 936f indicate a two component diffusion model with normal range factors of 2, 10 and 50, respectively. For comparison, trace 936h indicates the same model with a uniform range factor of 10. As $\gamma_n$ becomes sufficiently large, e.g., 10 or greater, model probabilities are also not sensitive to the broadness of the normal prior, and the results are very close to broad range uniform prior plotted for comparison. At low noise the true two component diffusion model is most probable. Again, model ranking is not changed by $\gamma_n$.

Figure 9E:
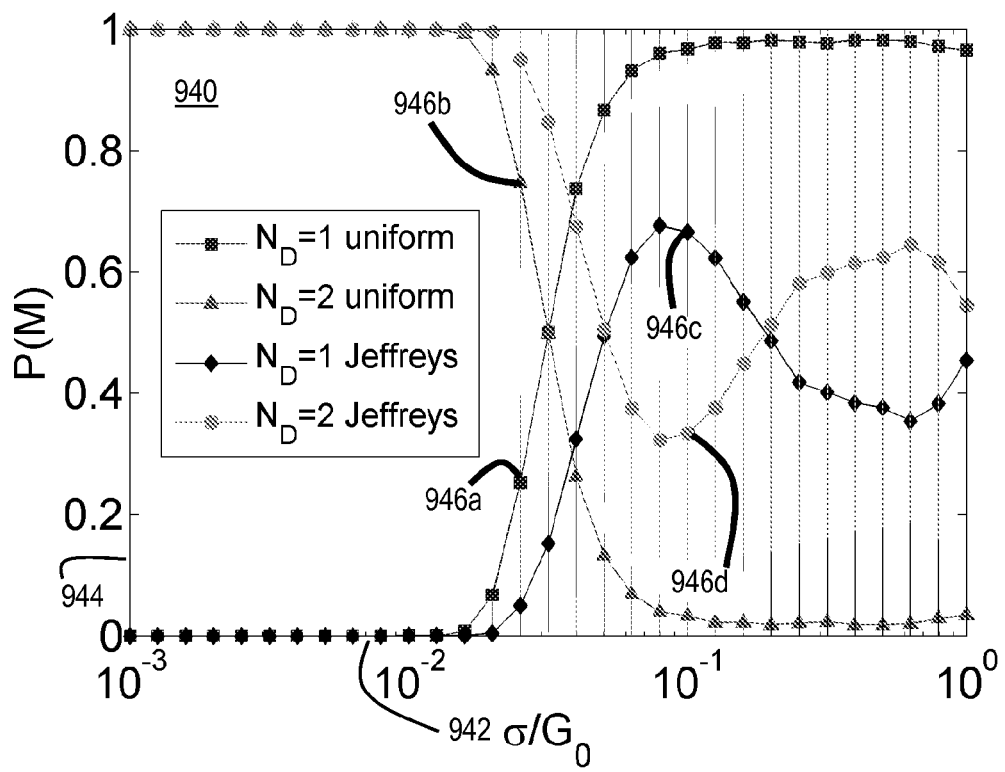

Jeffreys prior probabilities for parameter values given a model were also tested for the effect on model ranking. Jeffreys priors represent equal probability per decade (scale invariance) for broad prior ranges that represents great uncertainty in a given parameter. FIG. 9E is a graph 940 that illustrates example effect of Jeffreys priors on model probabilities, according to an embodiment. The horizontal axis 942 is relative noise; and, the vertical axis 944 is P(M). The simulated TACF data is based on $D_2/D_1$=5 and large n but without modeling optics in detail. Model probabilities were evaluated using the Laplace approximation. Trace 946a indicates a one component diffusion model with a uniform range factor of 10 for comparison with trace 946c that indicates a one component diffusion model using Jeffreys prior probabilities for parameter values given a model. Trace 946b indicates a true two component diffusion model with a uniform range factor of 10 for comparison with trace 946d that indicates a two component diffusion model using Jeffreys prior probabilities for parameter values given a model. At low noise the difference in priors has no effect. Above 1% relative error, however, the model probabilities of the two models are much closer with the Jeffreys priors than with the uniform priors; and, model ranking is even affected, e.g., at noise levels above about 30%.

Figure 9F:
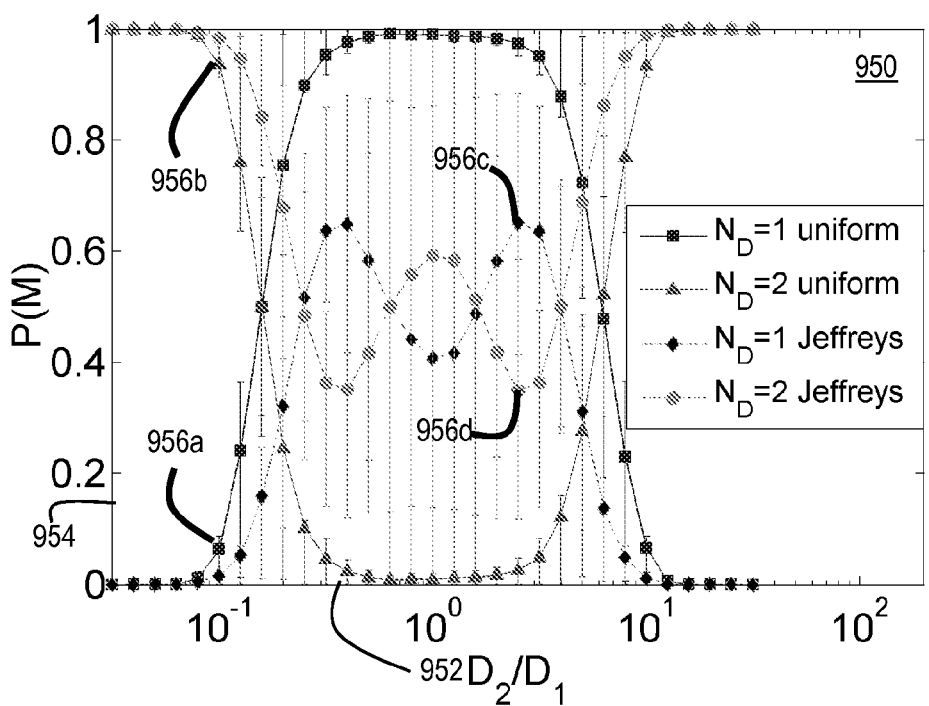

FIG. 9F is a graph 950 that illustrates example effect of Jeffreys priors on model probabilities, according to another embodiment. The horizontal axis 952 is ratio of two diffusion coefficients $D_2/D_1$; and, the vertical axis 954 is P(M). The simulated TACF data is based on two component diffusion and a constant relative noise of 4% with varying $D_2/D_1$ as in FIG. 7E and FIG. 7F. Model probabilities were evaluated using the Laplace approximation. Trace 956a indicates a one component diffusion model with a uniform range factor of 10 for comparison with trace 956c that indicates a one component diffusion model using Jeffreys prior probabilities for parameter values given a model. Trace 956b indicates a true two component diffusion model with a uniform range factor of 10 for comparison with trace 956d that indicates a two component diffusion model using Jeffreys prior probabilities for parameter values given a model. When $D_2$ is more than ten times $D_1$, or less than a tenth of $D_1$, the "true" two component diffusion model is favored for both Jeffreys and uniform priors. In the $D_2/D_1$ range from about 0.1 to about 10, however, the model probabilities of the two models are much closer with the Jeffreys priors than with the uniform priors; and, model ranking is even affected, e.g., at ratios near 1.0.

Model probabilities computed using Laplace method (e.g., in step 605 of FIG. 6) are compared with those computed using a Monte Carlo method (e.g., in step 603 of FIG. 6). FIG. 10A and FIG. 10B are graphs that illustrate an example dependence on the method of integration for the marginal probability, according to various embodiments. FIG. 10A is a graph 1000 that illustrates example effect of integration method as a function of relative noise, according to an embodiment. The simulated data is the same as used in FIG. 9A, described above. Trace 1006a indicates a one component diffusion model used with the Laplace approximation for comparison with trace 1006c that indicates a one component diffusion model used with a more precise Monte Carlo method described above. Trace 1006b indicates a two component diffusion model used with the Laplace approximation for comparison with trace 1006d that indicates a two component diffusion model used with a Monte Carlo method. At low noise, relative error less than a few percent, both integration methods agree closely. At high noise levels, e.g., relative errors over 10%, the Laplace approximation favors the simpler model slightly more.

FIG. 10B is a graph 1010 that illustrates example effect of integration method as a function of relative diffusion, according to an embodiment. The simulated data is the same as used in FIG. 9A, described above with uniform relative noise fixed at 4% and The diffusion coefficient of one component varied to provide a range of $D_2/D_1$ from less than 0.1 to more than 10. Trace 1016a indicates a one component diffusion model used with the Laplace approximation for comparison with trace 1016c that indicates a one component diffusion model used with a Monte Carlo method. Trace 1016b indicates a two component diffusion model used with the Laplace approximation for comparison with trace 1016d that indicates a two component diffusion model used with a Monte Carlo method. At all plotted values of the ratio $D_2/D_1$, both integration methods agree closely.

Results of two methods are almost identical for low noise, and for the whole range of $D_2/D_1$ (at relative noise of 4%). This justifies the approximation of posterior to normal distribution. Deviation of the two methods from each other in the high noise range (relative error>10%) could be due to the ineffective sampling of MC method when the posterior becomes really broad. It is anticipated that the model probability for high noise should plateau, where Laplace gives a better asymptotic behavior. In practice, high noise data should be avoided in the experiments to yield better inference.

3.2 Experimental FCS Data

FCS was performed using a customized Olympus FV 300 confocal microscope (Olympus, Tokyo, Japan). Excitation was provided by the 488-nm laser line of an Argon ion laser that is focused into samples by a water-immersion objective (60×, NA 1.2; Olympus, Tokyo, Japan). The laser power, measured before the objective, was 30 μW. The emitted light, which passed an internal 3× magnification stage in the confocal microscope, passed through a 150-μm pinhole and was detected by an avalanche photodiode (SPCM-AQR-14-FC; Pacer, Berkshire, UK). The autocorrelation curves were computed online using a hardware correlator (Flex02-01D; Correlator.com, Bridgewater, N.J., USA).

Figure 11A:
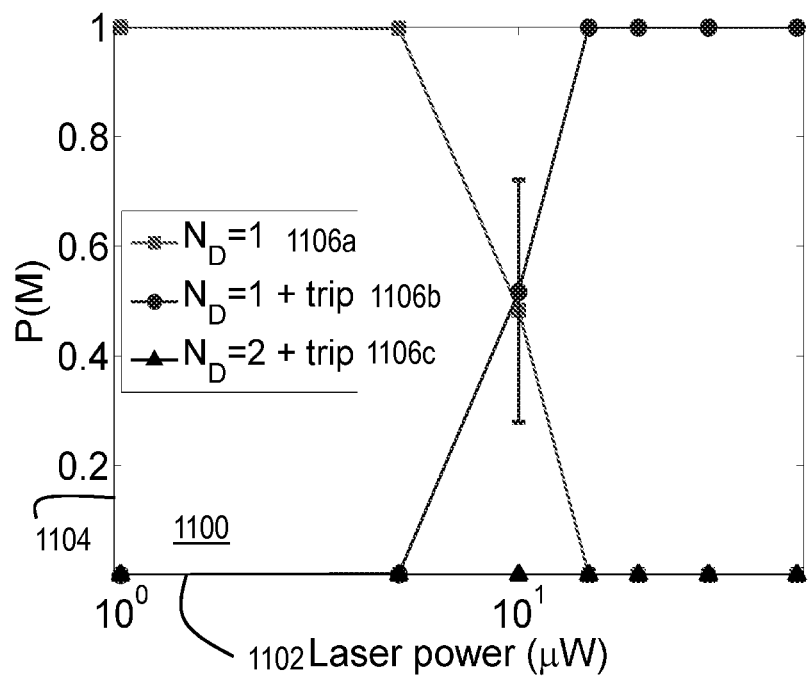
FIG. 11A and FIG. 11B are graphs that illustrate an example method on experimental FCS data, according to an embodiment.
Figure 11B:
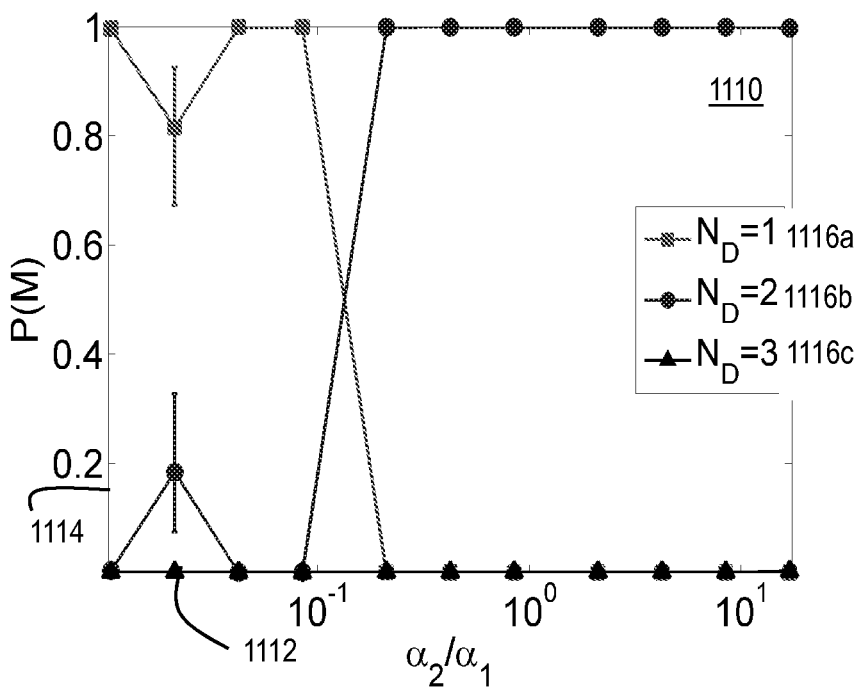

To test the applicability of the proposed Bayesian approaches to experimental FCS measurements with varying physical process, we analyzed one-component fluorescein solutions with varying excitation laser powers using multiple TACF curves to estimate noise correlation. FIG. 11A and FIG. 11B are graphs that illustrate an example method on experimental FCS data, according to an embodiment. FIG. 11A is a graph 1100 that illustrates the effect of laser power on model selection, according to an embodiment. The horizontal axis 1102 is laser power in microwatts (μW); and, the vertical axis 1104 is probability of the model given the data. The FCS data comprises 5 mean TACF curves used to estimate noise correlation. Each mean curve is the average of 2 individual curves calculated by the correlator with acquisition time>20 seconds. Trace 1106a indicates the probability of a one diffusion element model. Trace 1106b indicates the probability of a one diffusion element model with triplet state excitation affecting fluorescence. Trace 1106c indicates the probability of a two diffusion element model with triplet state excitation affecting fluorescence.

When the excitation laser power is low, the presented approach prefers one-component model because the fraction of fluorescein in the triplet state is low. As the laser power increases, the one-component with triplet state model comes to be preferred because the brightness of the dye increases as well as the fraction of dye molecules in the triplet state and the triplet state can be resolved. Again, the over-parameterized two-component with triplet state model is never preferred.

The ability of the procedure to detect multiple diffusing species at distinct concentration ratios was tested using mixtures of Atto565 and Atto565-labeled Streptavidin. FIG. 11B is a graph 1110 that illustrates the effect of relative amplitude on model selection, according to an embodiment. The horizontal axis 1112 is relative amplitude $a_2/a_1$; and, the vertical axis 1114 is probability of the model given the data. Here $a_2$ represents the amplitude of Atto565-labeled Streptavidin and $a_1$ represents the amplitude of Atto565 alone. FCS data was collected for mixtures of Atto565 and Atto565-labeled Streptavidin. 5 mean TACF curves are analyzed and each mean curve is the average of 2 individual curves. Trace 1116a indicates the probability of a one diffusion element model with one triplet state. Trace 1116b indicates the probability of a two diffusion element model with one triplet state. Trace 1116c indicates the probability of a three diffusion element mode with one triplet state. For all models, the triplet blinking time was fixed at 1.5 us, which is the triplet blinking time of Atto565 measured under the same experimental condition.

As the concentration of Streptavidin increases, the model probability transitions from the one-component to the two-component model consistent with simulations. Unlike the simulated data, the experimental alpha ratios never reach high enough levels for the models to transition back to the one component model. This is due to the presence of free Atto565 even in the pure Streptavidin sample, which has the alpha ratio ~0.61. Thus, the two-component model is still preferred even when the nominal ratio of Atto565-labeled Streptavidin to Atto565 is high. The presence of free Atto565 in the pure Streptavidin sample is confirmed by the analysis of the measurement of the pure Streptavidin solution. Analysis of the photon arrival times data for the same systems using a single TACF curve to estimate noise correlation gave similar results.

Typical FCS data contain highly correlated measurements that result in noise variations along the TACF that considerably underestimates the true uncertainty in the measured TACF data. Two approaches are presented above to deal with this issue and properly estimate the noise and its correlation using either multiple TACF curves or a single photon-count trace. Estimating noise and its correlation from a single photon-count trace proves useful for applications of the presented approach to biological datasets in which multiple measurements from the same process may not be feasible.

It is demonstrated that proper estimation of noise correlations allows the presented approach to infer multiple component diffusion models from TACFs under a variety of noise levels and sampling conditions. Complex models are only preferred over simple models when the data resolution (e.g., noise level) justifies the use of additional complexity, whereas simpler models are preferred when noise is high. Importantly, ignoring noise correlations leads to over-fitting data and artificially increases the probability of overly complex models, leading to over-interpretation of measured data. Thus, noise correlations should be considered generally for the proper analysis of FCS data whenever possible. We also illustrate the capability of the presented approaches to identify the correct number of diffusing components in experimental FCS data by analyzing experimental datasets for a two-component system with different component fractions. Incorporating additional models and/or physical processes into the current Bayesian framework is straightforward. Thus, the proposed procedure provides a convenient framework in which to interpret FCS data generally in an objective manner, in particular when testing competing hypotheses of biophysical mechanism in complex biological systems in which underlying physical processes are generally unknown.

It is anticipated that other embodiments will include the effects of sample heterogenetiy, non-stationarity of the physical process, and photobleaching on the analysis of FCS data. Further, non-uniform model and parameter priors may be used, as evidence is accumulated in specific biological systems for the preference of specific models and their parameters in various contexts. Automation of the blocking-procedure presented here will enable the broad application of Bayesian-based model selection to image correlation spectroscopy (ICS), in which a large number of correlation functions are derived from sub-images of high spatial and temporal resolution image data. In this context, application of traditional statistics approaches that rely on pair-wise statistical tests are impractical due to their complexity, do not allow for the direct comparison of non-nested competing models, and do not generate model probabilities directly because they do not condition hypothesis-testing on the models themselves.

4. Example MSD Embodiments

Particle trajectories contain important information about the transport dynamics and local environments of biological molecules, providing insights into protein trafficking, directed transport along cytoskeletal structures, local confinement, chromosome segregation, and endocytosis, among others. The effectiveness of the presented approach for a Bayesian-based procedure is demonstrated by application to simulated mean square displacement (MSD) data as well as to the analysis and classification of chromosome (Mori, M., N. Monnier, et al. "Intracellular transport by an anchored homogeneously contracting F-actin meshwork." *Curr Biol* v21(7), pp 606-611, 2011) and kinetochore (Kitajima, T. S., M. Ohsugi, et al., "Complete kinetochore tracking reveals error-prone homologous chromosome biorientation in mammalian oocytes." *Cell* v146(4), pp 568-581, 2011) motions as well as CD36 receptor dynamics in macrophage cells (Jaqaman, K., H. Kuwata, et al., "Cytoskeletal control of CD36 diffusion promotes its receptor and signaling function." *Cell* v146(4), pp 593-606, 2011).

4.1 Simulated MSD Data

To explore the role of increasing noise in the MSD on model selection properties that may result from limited SPT length or number of available trajectories, simulated trajectories were examined for which the true motion model is known and the noise properties can be varied systematically. Diffusive single-particle trajectories were simulated in 3D by drawing random step lengths in each of the three Cartesian directions from a Gaussian distribution with zero mean and standard deviation equal to $\{\sqrt{(2Ddt)}\}$, where D is the diffusion coefficient and dt is the time interval for each step. Confinement of a diffusing particle was modeled as a reflecting spherical boundary of radius $R_C$ centered at the initial particle position. Directed flow was modeled by adding a fixed displacement of length vdt to the diffusive motion at each time step, where v is the velocity vector.

As a low noise condition, parameters were used that are optimistic for experimental SPT datasets in living cells; namely, 50 trajectories of length 600 steps for each simulated dataset. Trajectories were simulated for particles undergoing diffusion plus convection with DD=0.005 $\mu m^2/s$, dt=1 s, and a systematically varying v. All 50 trajectories with the same v were used to compute the mean MSD curve; thus there was no heterogeneity between the motions of the individual particles in the datasets for this simulation. For a particle trajectory undergoing diffusion plus flow, with MSD equation given by Equation 19, $$MSD_{DV}(\tau)=6D\tau+v^2\tau^2 \quad (19)$$

(from Eqs. 5a and 5d), the magnitudes of the diffusive and directed motion terms are equal for $\tau=6D/v^2$. As v increases and this timescale becomes smaller than the sampling interval dt of the particle trajectory, which sets the minimum value of $\tau$ in the MSD curve, the MSD curve should become dominated by directed motion and model selection should prefer the simpler model pure flow (V) over the more complex true model diffusion plus flow (DV). Similarly, as v decreases and this timescale becomes larger than the maximum value of $\tau$ in the MSD curve, the curve should become dominated by diffusive motion and model selection should prefer the simpler model pure diffusion (D) over diffusion plus flow (DV).

Figure 12C:
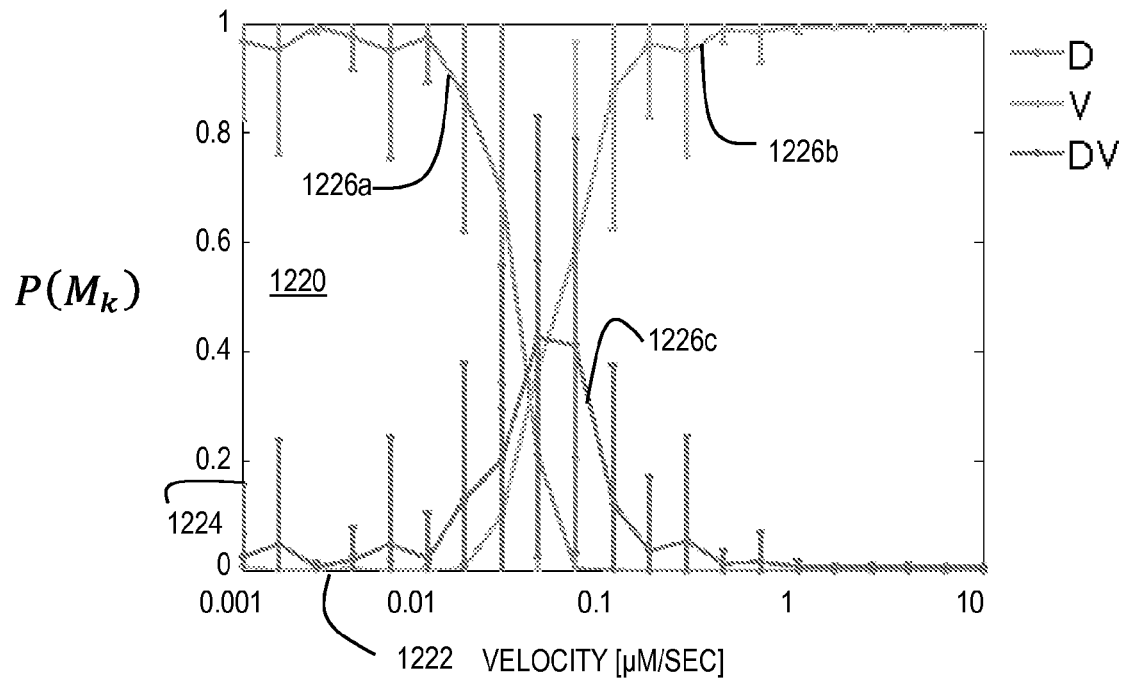

FIG. 12A through FIG. 12D are graphs that illustrate an example effect of noise on analysis of simulated MSD data, according to an embodiment. FIG. 12A is a graph 1200 that illustrates example effects of velocity in a mixed diffusion flow model on probability of a model given the data, abbreviated here as $P(M_k)$, under low noise conditions, according to an embodiment. The horizontal axis 1202 is velocity in $\mu m/s$; and the vertical axis 1204 is $P(M_k)$, which is dimensionless. Trace 1206a depicts the probability and standard deviation for a simple diffusion model D. Trace 1206b depicts the probability and standard deviation for a simple convection (flow) model V. Trace 1206c depicts the probability and standard deviation for a combined diffusion and convection (flow) model DV.

It is found that the presented approach for model selection behaves as expected in the low noise condition. The combined model is most probable in a middle range where neither diffusion nor flow dominates. Importantly, the range of values of v over which the true DV model can be resolved shrinks with increasing experimental noise, which was varied by reducing the number of averaged MSD curves and the length of the trajectories used to calculate each MSD curve. FIG. 12B is a graph 1210 that illustrates example effects of velocity in a mixed diffusion flow model on $P(M_k)$ under intermediate noise conditions, according to an embodiment. The horizontal axis 1212 is velocity in $\mu m/s$; and the vertical axis 1214 is $P(M_k)$. Trace 1216a, trace 1216b and trace 1216c depict the probability and standard deviation for a simple diffusion model D, simple flow model V and combined diffusion and flow model DV, respectively. The combined model is most probable in a more limited range of velocities. FIG. 12C is a graph 1220 that illustrates example effects of velocity in a mixed diffusion flow model on $P(M_k)$ under high noise conditions, according to an embodiment. The horizontal axis 1222 is velocity in $\mu m/s$; and the vertical axis 1224 is $P(M_k)$. Trace 1226a, trace 1226b and trace 1226c depict the probability and standard deviation for a simple diffusion model D, simple flow model V and combined diffusion and flow model DV, respectively. The combined model is almost never most probable.

Similar effects can be seen for simulated particle trajectories undergoing confined diffusion (Equation 5c), for which the confinement begins to dominate the MSD curve at a timescale $\tau=R_c^2/6D$, and for confined diffusion plus flow, for which the confinement is apparent in the MSD curve only when $v R_c/6D \leq 1$.

Figure 12D:
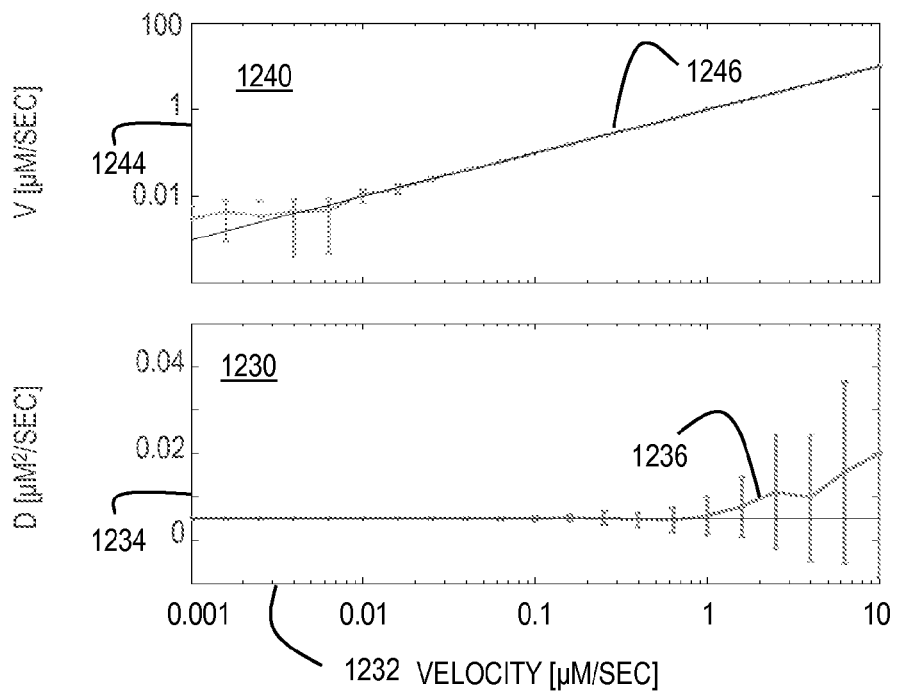

Once the motion model has been established using multiple hypothesis testing, the parameter values associated with the model may be interpreted. Evaluation of the parameter values as a function of model probability shows that when model probability is high the parameter values are well estimated, whereas their values become poorly estimated when the probability is low. FIG. 12D is a pair of graphs 1230 and 1240 that illustrated parameter value estimation dependence on model probability. The horizontal axis 1232 is velocity in μm/s. The vertical axis 1234 is diffusion parameter value in $\mu m^2/s$. The vertical axis 1244 is velocity in μm/s. Trace 1236 shows the estimated value of the diffusion coefficient with error bars. At high velocity where the diffusion and mixed DV models have low probability, the uncertainty in the diffusion parameter is high. Trace 1246 shows the estimated value of the velocity with error bars. At low velocity where the flow and mixed DV models have low probability, the uncertainty in the velocity is high. Thus, the presented techniques provide a pre-screening filter for the downstream interpretation of model parameter values, which are only reliable when the probability of the model to which they belong is also sufficiently favorable.

To explore the role of heterogeneity between the motions of individual particles in a dataset on the presented techniques, trajectories were simulated as above but with varied distribution of a selected parameter (v, D or $R_C$) within each group of trajectories. This type of heterogeneity means that even if the MSD curve for each individual particle trajectory in the dataset were perfectly measured, there would still be variation between the different MSD curves in the sample that would increase the standard error in the mean MSD curve. FIG. 13A through FIG. 13D are graphs that illustrate an example effect of heterogeneity on analysis of simulated MSD data, according to an embodiment.

Figure 13A:
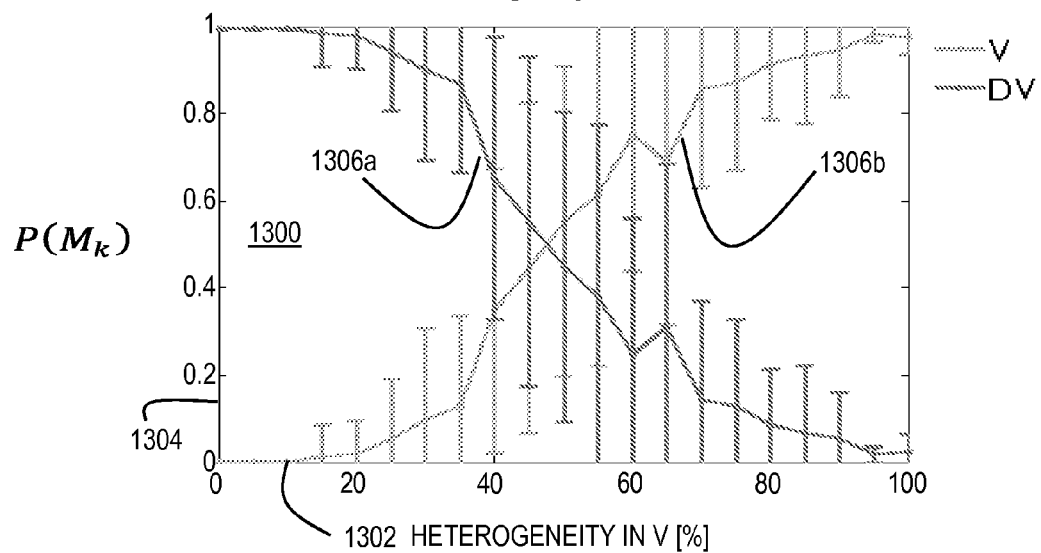
FIG. 13A through FIG. 13D are graphs that illustrate an example effect of heterogeneity on analysis of simulated SPT data, according to an embodiment.
Figure 13B:
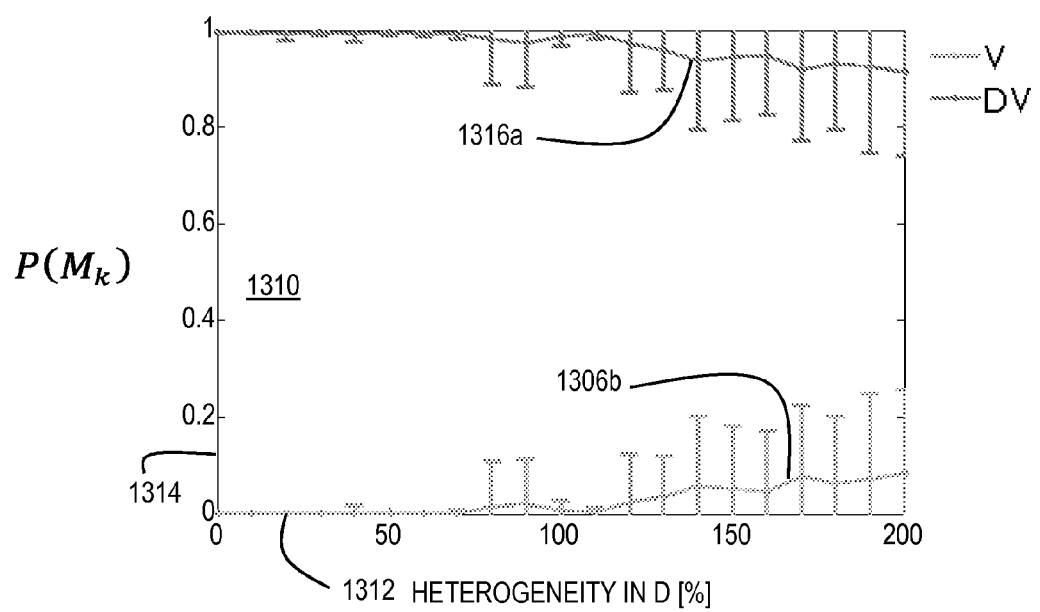

FIG. 13A is a graph that illustrates example effect of heterogeneity in velocity on model probability, according to an embodiment. The horizontal axis 1302 is heterogeneity in velocity, defined as the standard deviation in the particle velocities, expressed as a percent change of the mean particle velocity. The vertical axis 1304 is model probability. Trace 1306a indicates the mean and error in probability of the true combined diffusion and flow model DV. The probability of this model decreases with increasing heterogeneity. Trace 1306b indicates the mean and error in probability of a simple flow model V. FIG. 13B is a graph that illustrates example effect of heterogeneity in diffusion coefficient on model probability, according to an embodiment. The horizontal axis 1312 is heterogeneity in diffusion coefficient, defined as the standard deviation in the coefficient, expressed as a percent change of the mean diffusion coefficient. The vertical axis 1314 is model probability. Trace 1316a indicates the mean and error in probability of the true combined diffusion and flow model DV. The probability of this model decreases very little with increasing heterogeneity. Trace 1316b indicates the mean and error in probability of a simple flow model V.

Figure 13C:
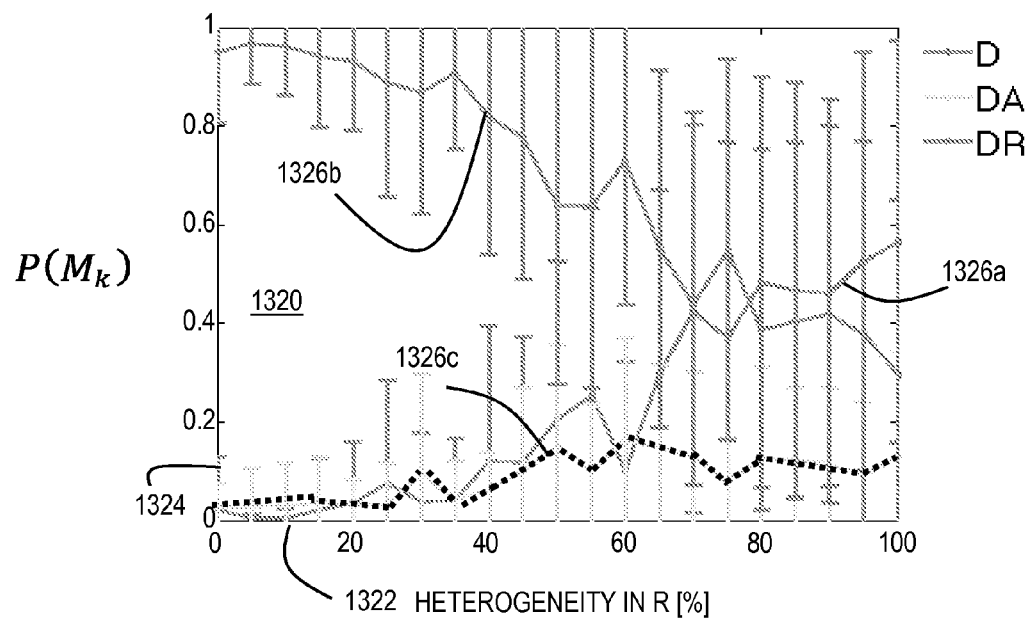
Figure 13D:
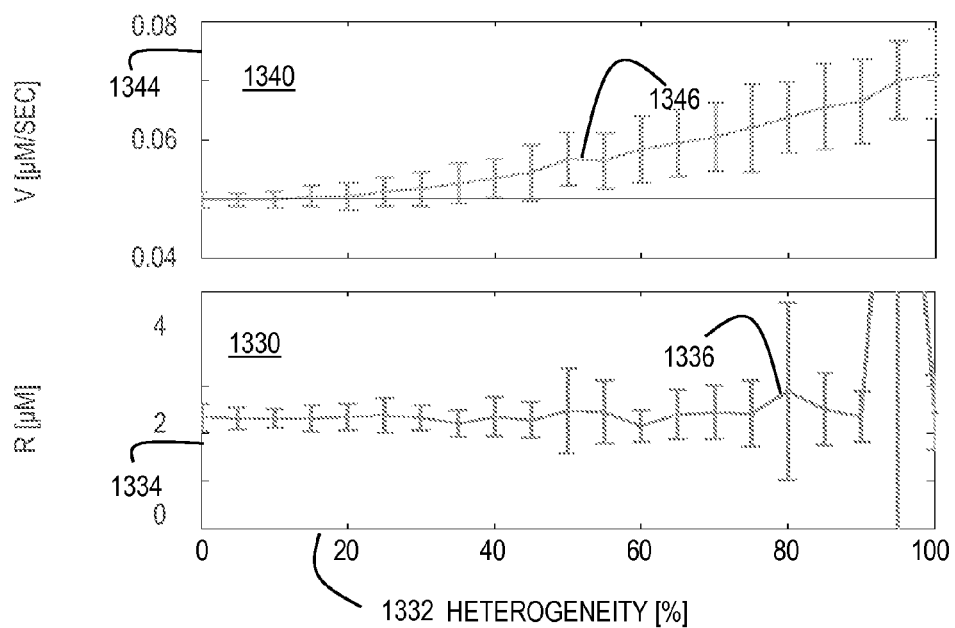

FIG. 13C is a graph that illustrates example effect of heterogeneity in radius of confinement $R_c$ on model probability, according to an embodiment. The horizontal axis 1322 is heterogeneity in $R_c$ defined as the standard deviation in the radius, expressed as a percent change of the mean radius. The vertical axis 1324 is model probability. Trace 1326a indicates the mean and error in probability of a simple diffusion model D. Trace 1326b indicates the mean and error in probability of the true confined diffusion model DR. The probability of this model decreases with increasing heterogeneity. Trace 1326c indicates the mean and error in probability of an anomalous diffusion model DA. FIG. 13D is a pair of graphs that illustrate example parameter value estimation in the presence of heterogeneity, according to an embodiment. The horizontal axis 1332 is heterogeneity. The vertical axis 1334 is estimate of the value of $R_c$ in μm. Trace 1336 indicates the estimated value and uncertainty in the estimate for $R_c$. The vertical axis 1344 is estimate of the value of v in μm/s. Trace 1346 indicates the estimated value and uncertainty in the estimate for v.

As anticipated, as heterogeneity between particles increased, the ability to resolve the true motion model diminished, similar to the effect of increasing experimental noise in the mean MSD. In the case of simulated diffusion plus flow trajectories, the Bayesian model selection procedure prefers the pure flow model at high heterogeneity in v (FIG. 13A) because heterogeneity in v shifts the effective v measured from the MSD curve to a higher value than the true mean value of v in the particle population (FIG. 13D, upper graph). Heterogeneity in D, on the other hand, gives an effective D measured from the mean MSD curve that is equal to the true mean value of D in the particle population. Finally, heterogeneity in confinement radius for simulations of confined diffusion has a dramatic effect because it changes the form of the mean MSD curve such that the standard confined diffusion model function is no longer a good fit. At low heterogeneity in $R_c$, the confined diffusion model still fits better than the other tested models, but as heterogeneity increases, the simpler pure diffusion model is preferred. Thus, heterogeneity in particle motions within a dataset can mask the ability to resolve their true motion, even if they are undergoing the same type of physical motion.

In order to eliminate heterogeneity from biological samples, classification into less-heterogeneous subgroups is commonly used. The criterion used for this classification must be appropriately chosen to reduce heterogeneity. In practice, an appropriate criterion will not be known a priori, and a biological coordinate along which to classify the data must be hypothesized. We suggest (and illustrate in the below applications) that initially all particle trajectories should be analyzed together, then the trajectories should be split into two groups along a hypothesized coordinate and re-analyzed to look for significant differences in preferred model or parameter values between the two groups. Such differences would suggest biologically relevant variation along the chosen coordinate, which can be further explored by repeatedly sub-dividing the trajectories into smaller sub-groups. However, it is important to keep in mind that while classification into appropriate subgroups will reduce heterogeneity in motion models and/or parameter values, allowing resolution of distinct types of physical motion present in the biological system, it will also typically reduce the number of individual-particle MSD curves available per subgroup, effectively increasing the level of experimental noise in the mean MSD curve. Thus, while classification is very important to the investigation of biological mechanism underlying single particle motion, in practice, additional data acquisition will likely be required to resolve more complex models as the level of classification increases.

4.2 Experimental MSD Data

The relevance of the presented approach for analysis of experimental biological datasets was also tested.

4.2.1 Chromosome MSD Data

Figure 14A:
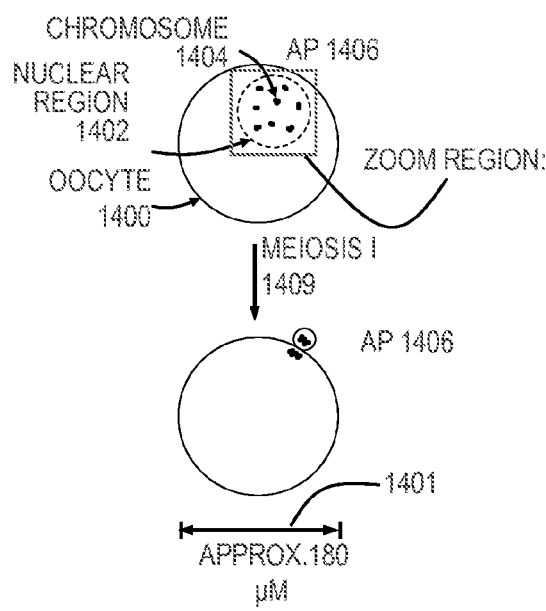
FIG. 14A and FIG. 14B are diagrams that illustrate example chromosome trajectory data, according to an embodiment.
Figure 14B:
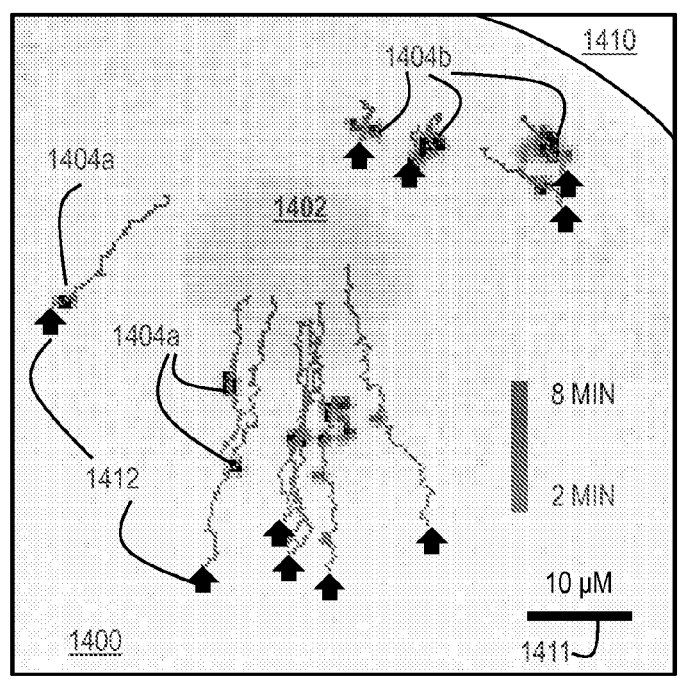

The presented approach was applied to the motion of chromosomes during meiosis I in starfish oocytes. This dataset illustrates many of the principles that were found above for simulated trajectories. FIG. 14A and FIG. 14B are diagrams that illustrate example chromosome trajectory data, according to an embodiment. FIG. 14A is a block diagram that illustrates example motion of chromosomes 1404 toward an animal pole (AP) 1406 near a nuclear region 1402 of a starfish oocyte 1400. The distance of 180 microns is indicated by scale bar 1401. During meiosis I in these cells, chromosomes are transported towards the spindle at the animal pole 1406 of the oocyte 1400 by contraction of a large actin meshwork that forms in the nuclear region 1402 after nuclear envelope breakdown (NEBD). Chromosomes from 4 oocytes were imaged and tracked at 2.6-second time resolution (a more than 5-fold improvement in resolution over previous studies) during the roughly 6-minute actin-dependent transport phase extending from 2 minutes to 8 minutes post NEBD. FIG. 14B is a diagram 1410 that superposes on a micrograph of the oocyte 1400 trajectories of several chromosomes 1404 in the period from 2 minutes to 8 minutes. The distance of 10 microns is indicated by scale bar 1411. The location of the nuclear region 1402 is indicated. The positions of the chromosomes at 2 minutes are indicated by the arrows 1412. The chromosomes 1404a and 1404b (collectively referenced herein as chromosomes 1404) are imaged in the micrograph at roughly halfway between the 2 minute and 8 minute marks.

FIG. 14C through FIG. 14G are graphs that illustrate an example effect of heterogeneity on analysis of chromosome MSD data, according to an embodiment. FIG. 14C is a graph 1420 that illustrates example MSD curves for the starfish oocyte chromosome trajectories. The horizontal axis 1422 indicates time lag in seconds. The vertical axis 1424 indicates mean square displacement in square microns ($\mu m^2$). Single particle MSD curves are indicated by traces 1426a, 1426b, 1426c and 1426d. The mean MSD curve is indicated by trace 1426f along with error bars indicating the standard error in the mean value. The standard deviation of the individual MSD curves about the mean curve is indicated by dot-dash traces 1426e.

The mean MSD curve over all of the chromosome trajectories was analyzed using the presented approach to test the set of 7 possible motion models shown in FIG. 1D. It was found that the diffusion plus flow model (DV) is strongly preferred over the other models, consistent with the previously proposed hypothesis that chromosomes diffuse within the actin meshwork as they are transported in a directed manner towards the spindle.

Visual comparison of the chromosome trajectories (FIG. 14B) suggested significant heterogeneity between the motion of chromosomes 1404b near to the AP and the chromosomes 1404a far from the AP, consistent with the previous finding that chromosome velocities are correlated with initial distance from the AP. To test this hypothesized heterogeneity using the approaches presented here, the chromosome trajectories were split into two groups based on their initial distance from the AP; and, the motions were reanalyzed. Of the 30 trajectories available, the 15 closest to the AP were put in one group (1-15) and the remaining in a second group (16-30). FIG. 14D is a graph that shows the model probabilities associated with each group. The horizontal axis 1432a indicates the members of the two groups. The vertical axis 1434 indicates the probability of all the models for the group. The areas 1436a indicate the combined diffusion and flow model DV. The areas 1436b indicate the simple flow model V. For the first group closest to the AP, the combined model DV is strongly preferred. In group 16-30 farther from the AP, the simple flow model V is the most probable, with the combined DV model also showing some noticeable probability. The sum of the probabilities adds to 1.0. Thus, the DV model was preferred for the chromosomes near the pole, but the simpler V model was preferred for chromosomes far from the pole. This shift to the simpler V model indicates that the velocity of the chromosomes far from the pole is high enough relative to their diffusion coefficient that the more complex DV model cannot be resolved at this level of noise.

Further sub-classification of the trajectories revealed a trend towards a preference for simpler models (D and V), as explained by the increasingly limited number of trajectories available within each sub-group, as well as a trend towards higher probability of the D model close to the AP and higher probability of the V model far from the AP. FIG. 14E is a graph that shows the model probabilities associated with each further divided group with overlap. The horizontal axis 1432b indicates the members of the four groups. The vertical axis 1434 indicates the probability of all the models for the group. The areas 1436a indicate the combined diffusion and flow model DV. The areas 1436b indicate the simple flow model V; and, the area 1436c indicates the simple diffusion model D. For the smaller first group (1-12) closest to the AP, the simple diffusion model and the combined model DV are about equally preferred. Further subdividing led to non-overlapping groups with good separation of models, as shown in FIG. 14F. The horizontal axis 1432c indicates the members of five non-overlapping groups. The vertical axis 1434 indicates the probability of all the models for the group. For example, simple diffusion is strongly preferred for trajectories in the closest group holding trajectories 1-6. The combined model and pure flow model are almost equally preferred in the group 7-12. The pure flow model is strongly preferred for the remaining three groups.

Figure 14G:
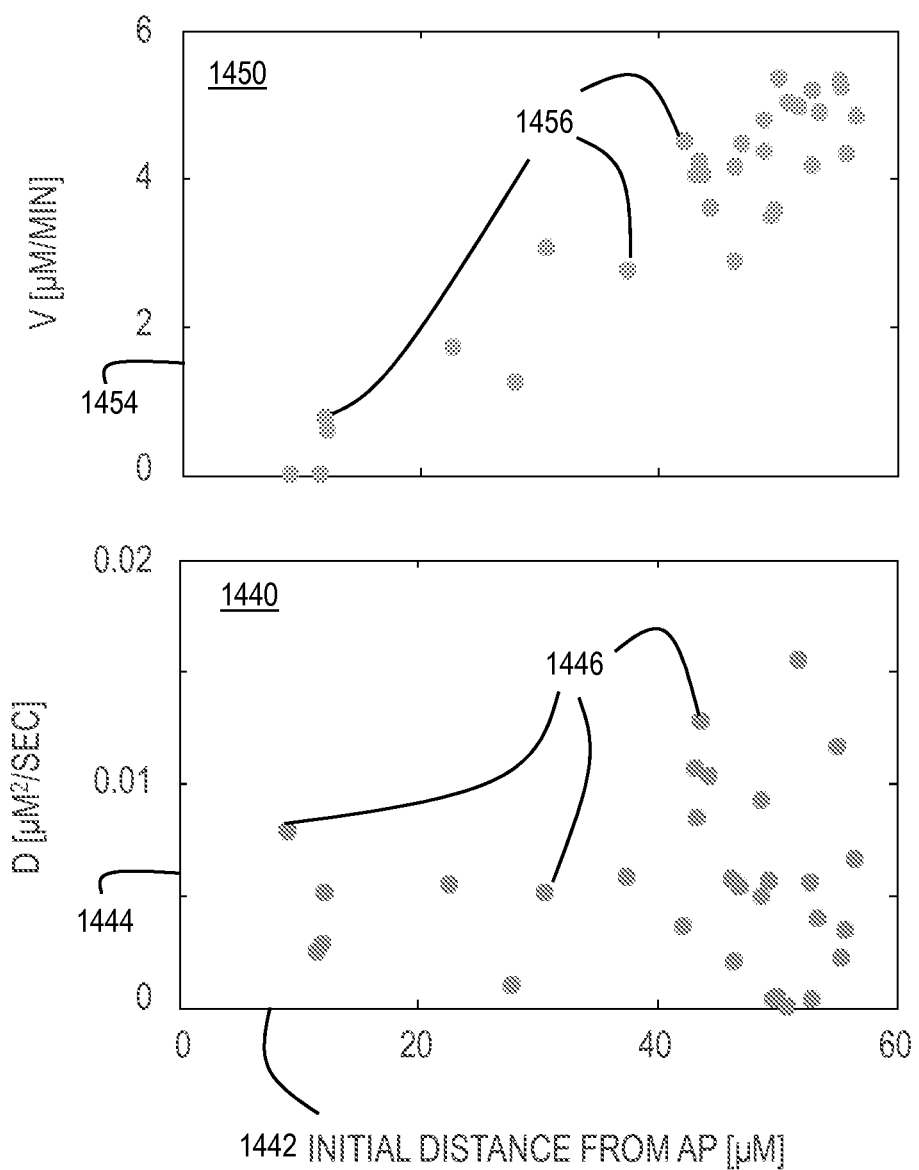

FIG. 14G is a pair of graphs 1440 and 1450 that illustrate the heterogeneity of model parameter values during meiosis, according to an embodiment. The horizontal axis 1442 indicates initial distance from animal pole (AP) in microns. The vertical axis 1444 indicates values for the diffusion coefficient D. Each point 1446 indicates the diffusion coefficient for an individual chromosome trajectory. The vertical axis 1454 indicates values for the velocity v. Each point 1456 indicates the velocity for each trajectory. Plotting the velocity and diffusion coefficients obtained for each individual chromosome revealed a linear dependence of velocity on initial distance from the AP, confirming the previous results obtained with lower-resolution trajectories. These results illustrate both the power of the presented approach to discover heterogeneity within a biological process and the corresponding trade-off between reducing heterogeneity and increasing noise due to limited data.

4.2.2 Bead MSD Data

High resolution imaging of filamentous actin in the nuclear space revealed a porous meshwork structure that was hypothesized to physically capture chromosomes via confinement within network pores. Experimental limitations in the maximum sampling rate feasible for chromosomes and limitations in the presence of the directed motion term in chromosome motion during transport; and limitations in the heterogeneity in chromosome velocities limited the ability to resolve confinement in the chromosome trajectories. However, an alternative means of probing the confinement structure of the actin meshwork is to examine the diffusion of inert beads through the meshwork. Bead trajectories can be analyzed for anomalous behavior or confinement to characterize the density of obstacles and sizes of pores in the meshwork. However, anomalous or confined behavior can be difficult to distinguish from correlated noise in MSD curves.

The usefulness of the presented approach was explored in the context of meshwork structure analysis by injecting PEG-coated 0.2-μm beads into the starfish oocyte nucleus just prior to NEBD while simultaneously over-expressing utrophin-EGFP to stabilize the actin bundles of the meshwork and prevent contraction. It was found that bead trajectories in the stabilized actin meshwork exhibited a wide range of behaviors.

Figure 15A:
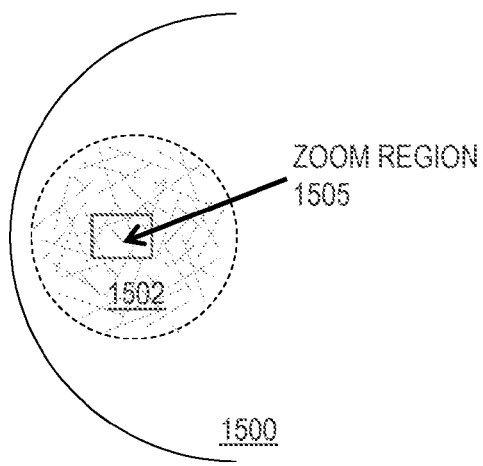
FIG. 15A and FIG. 15B are diagrams that illustrate example bead trajectory data, according to an embodiment.
Figure 15B:
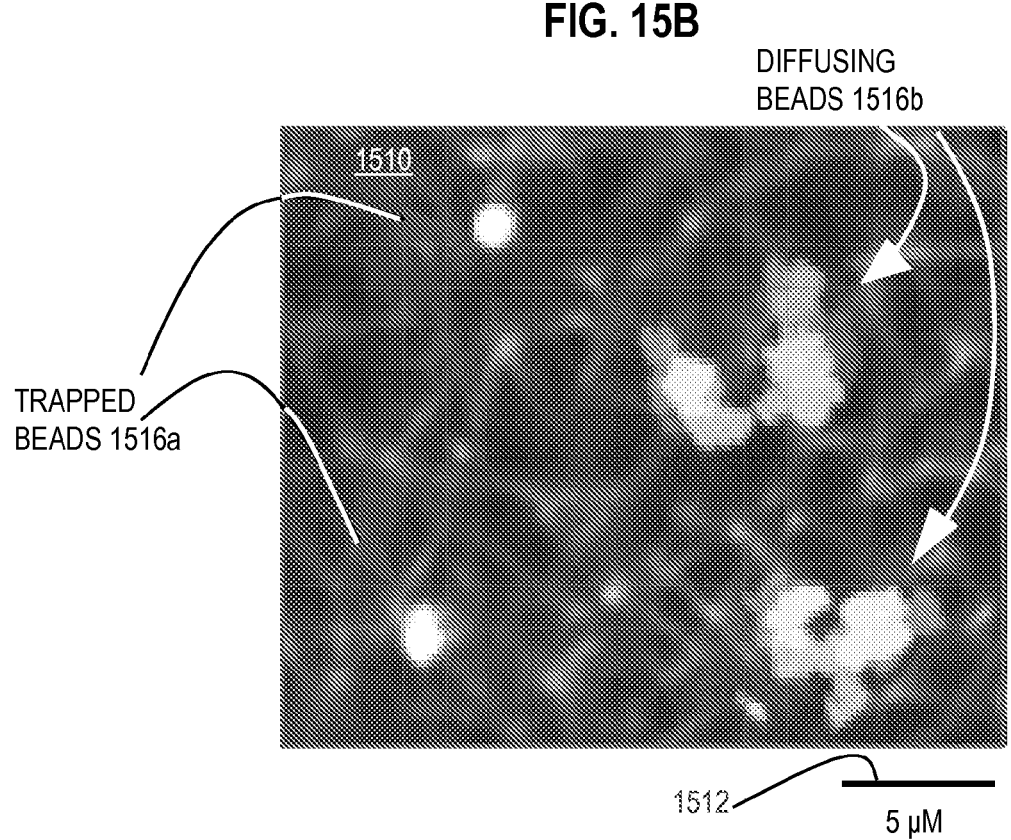

FIG. 15A and FIG. 15B are diagrams that illustrate example bead trajectory data, according to an embodiment. FIG. 15A is a diagram that illustrates an example cell 1500 with an actin mesh 1502. A zoom region 1505 is indicted in the actin mesh area 1502. FIG. 15B is a diagram 1510 that illustrates an example distribution of beads on a micrograph of the actin mesh in the zoom region of FIG. 15A, according to an embodiment. The distance of 5 microns is indicated by scale bar 1512. Trapped beads 1516a are indicated as are diffusing beads 1516b.

Figure 15C:
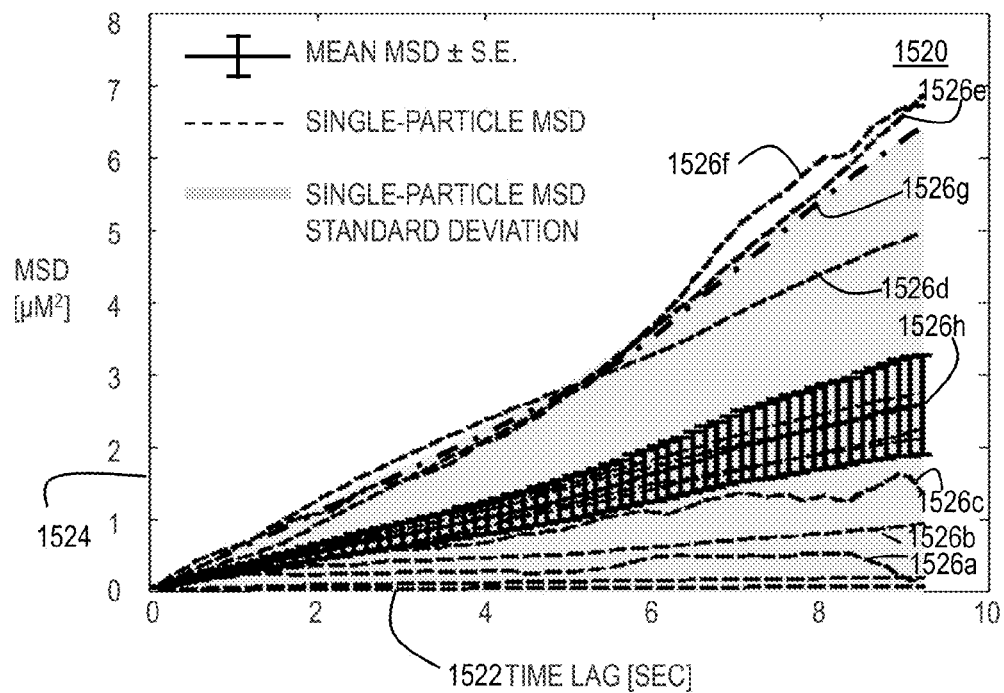
FIG. 15C through FIG. 15E are graphs that illustrate an example effect of heterogeneity on analysis of bead MSD data, according to an embodiment.
Figure 15D:
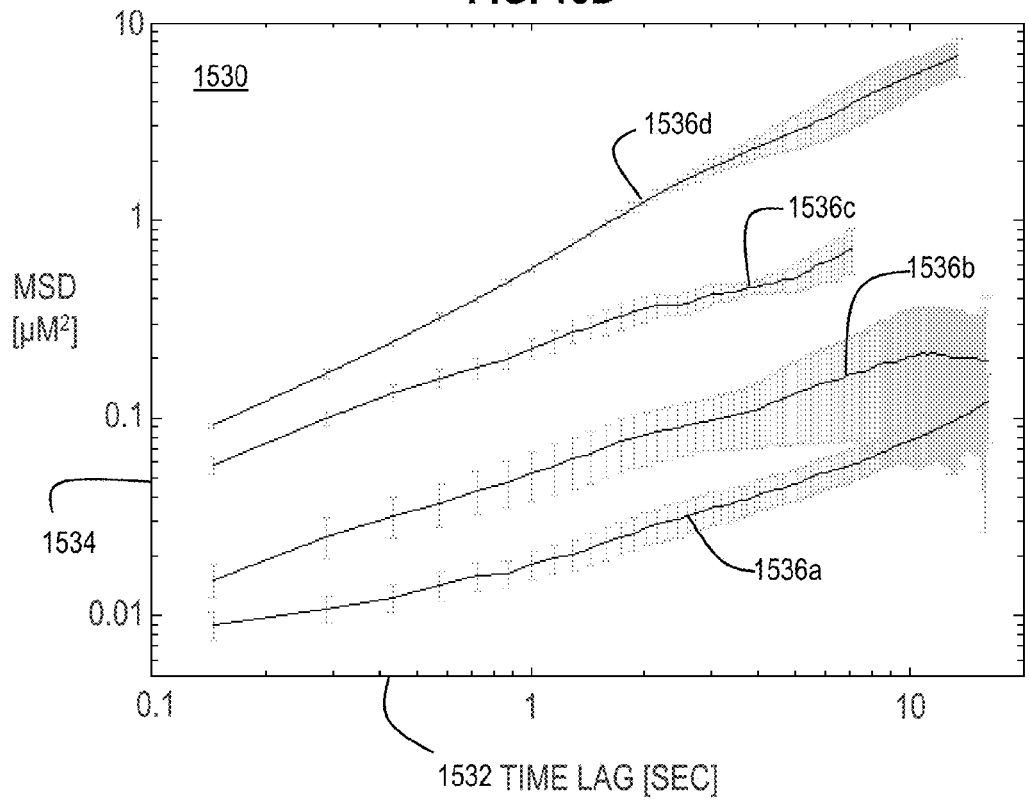
Figure 15E:
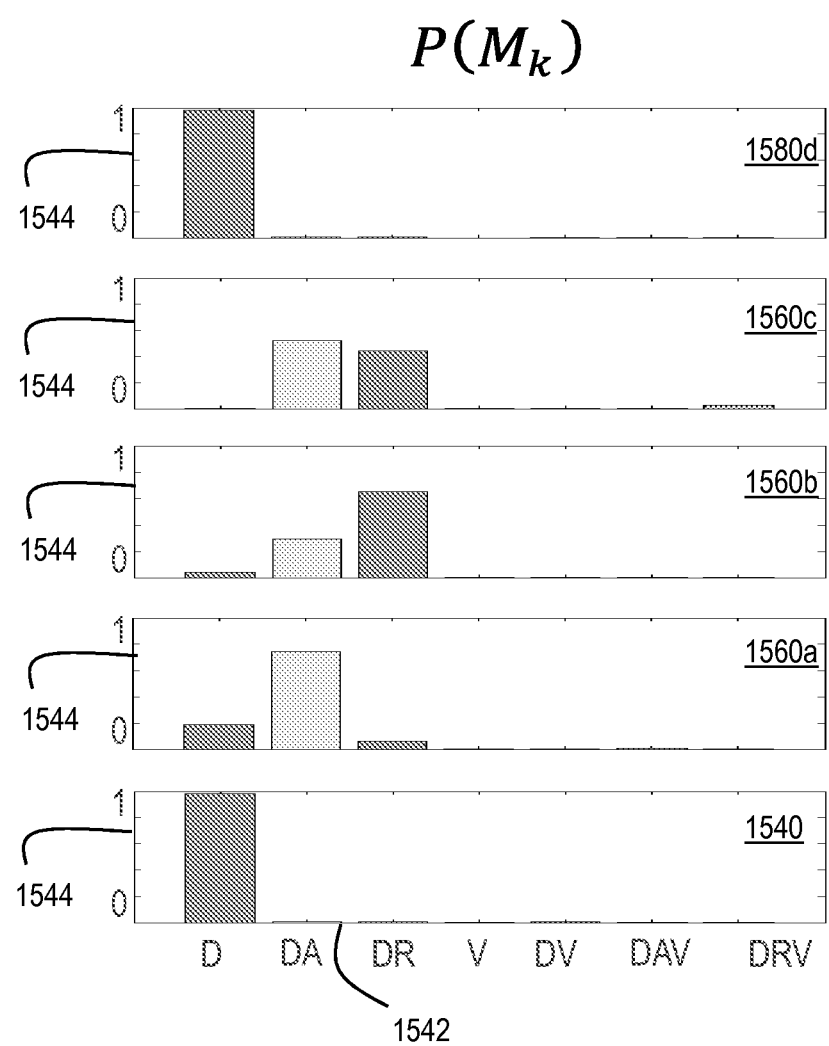

FIG. 15C through FIG. 15E are graphs that illustrate an example effect of heterogeneity on analysis of bead MSD data, according to an embodiment. FIG. 15C is a graph that illustrates example MSD curves for beads in actin, according to an embodiment. The horizontal axis 1502 indicates time lag, τ, in seconds. The vertical axis 1504 indicates mean square displacement in microns squared. Single particle MSD curves are indicated by traces 1526a, 1526b, 1526c, 1526d, 1526e and 1426f. The mean MSD curve is indicated by trace 1526f along with error bars indicating the standard error in the mean value. The standard deviation of the individual MSD curves about the mean curve is indicated by dot-dash traces 1426g.

Although model selection based on the mean MSD curve over all of the bead trajectories preferred the pure diffusion model, the individual bead trajectories were best explained by a variety of diffusive models, including the higher-complexity models of anomalous diffusion and confined diffusion. FIG. 15D is a graph 1530 that illustrates an example set of different MSD curves due to heterogeneity, according to an embodiment. The logarithmic horizontal axis 1532 indicates time lag in seconds. The logarithmic vertical axis 1534 indicates MSD in microns squared. Four sets of mean MSD curves with expected errors are plotted as trace 1536a, trace 1536b, trace 1536c and trace 1536d. Each trace may serve as different data to be used with the presented approach to determent the probability of a model in each of these four domains.

FIG. 15E is a stack of graphs 1540, 1560a, 1560b, 1560c and 1560d that illustrate example model probabilities for all MSD curves, and for the individual MSD curves of trace 1536a, 1536b, 1536c and 1536d, respectively, according of an embodiment. The horizontal axis 1542 indicates a model of the seven models D, DA, DR, V, DV, DAV, DRV. The vertical axis 1544 for each graph indicates $P(M_k)$ given the data. As can be seen, combining all MSD curves is shown in graph 1540 to favor the simple diffusion model. The MSD curve of trace 1536a is shown in graph 1560a to somewhat favor anomalous diffusion. The MSD curve of trace 1536b is shown in graph 1560b to somewhat favor confined diffusion. The MSD curve of trace 1536c is shown in graph 1560c to somewhat equally favor anomalous diffusion and confined diffusion. The MSD curve of trace 1536d is shown in graph 1560d to strongly favor simple diffusion.

In this case, therefore, the heterogeneity between the different particle motions is high enough that moving from a mean MSD curve over all particles to individual-particle MSD curves improves the ability to resolve complex models. This heterogeneity in bead dynamics may reflect heterogeneity in the underlying actin meshwork structure; for example, some beads may diffuse relatively freely through regions of the meshwork with lower density of actin bundles and larger pores between bundles, while other beads may become trapped within occasional small pores that are present in regions of the meshwork with higher actin density. The presented approach based on Bayesian analysis allows rigorous analysis of this heterogeneity by determining on a single-bead level whether each particle trajectory can be explained by simple diffusion or whether it provides convincing evidence of a more complex model of motion, such as anomalous or confined diffusion. Future perturbations of key actin regulating proteins such as Arp2/3 and formins have the potential to reveal the molecular origin of the structural heterogeneity observed in this system.

4.2.3 Kinetochore MSD Data

A Kinetochores in mouse oocytes have been found to undergo a variety of different motions over time during the process of meiosis. Here we sought to discover these phases using the presented approach and to characterize the motions using the set of motion models described in FIG. 1D.

Figure 16A:
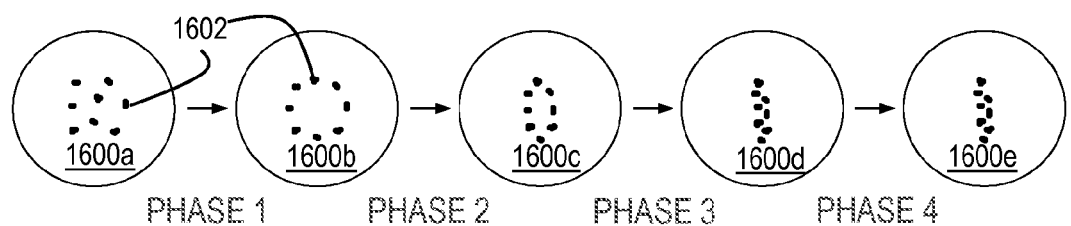
FIG. 16A and FIG. 16B are diagrams that illustrate example kinetochore trajectory data, according to an embodiment.
Figure 16B:
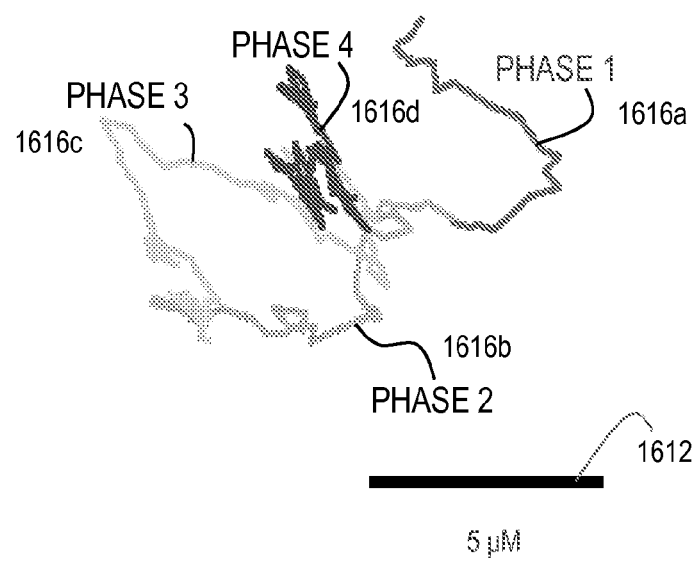

FIG. 16A and FIG. 16B are diagrams that illustrate example kinetochore trajectory data, according to an embodiment. FIG. 16A is a diagram that illustrates kinetochore trajectories during mouse oocyte meiosis I, according to an embodiment. In oocyte 1600a kinetochores 1602 are randomly distributed. During a phase 1 transition, the kinetochores 1602 form a ring in oocyte 1600b. During a phase 2 transition, the kinetochores 1602 form an elongated ring in oocyte 1600c. During a phase 3 transition, the kinetochores 1602 form a linear configuration in oocyte 1600d. During a phase 3 transition, the kinetochores 1602 form a linear configuration in oocyte 1600d. During a phase 4 transition, the kinetochores 1602 maintain a linear configuration in oocyte 1600d. FIG. 16B is a diagram that illustrates an example trajectory of a single kinetochore, according to an embodiment. The distance of 5 microns is given by scale bar 1612. Portion 1616a of the trajectory is associated with phase 1 transition. Similarly, portions 1616b, 1616c and 1616d are associated with transitions at phase 2, phase 3 and phase 4, respectively.

Figure 16C:
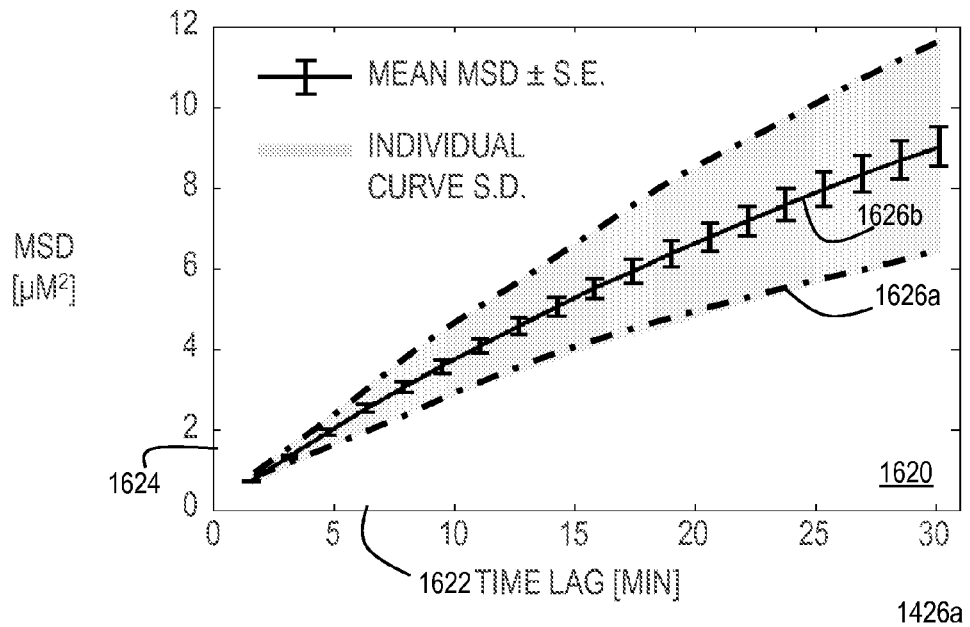
FIG. 16C and FIG. 16D are graphs that illustrate an example effect of heterogeneity on analysis of kinetochore MSD data, according to an embodiment.
Figure 16D:
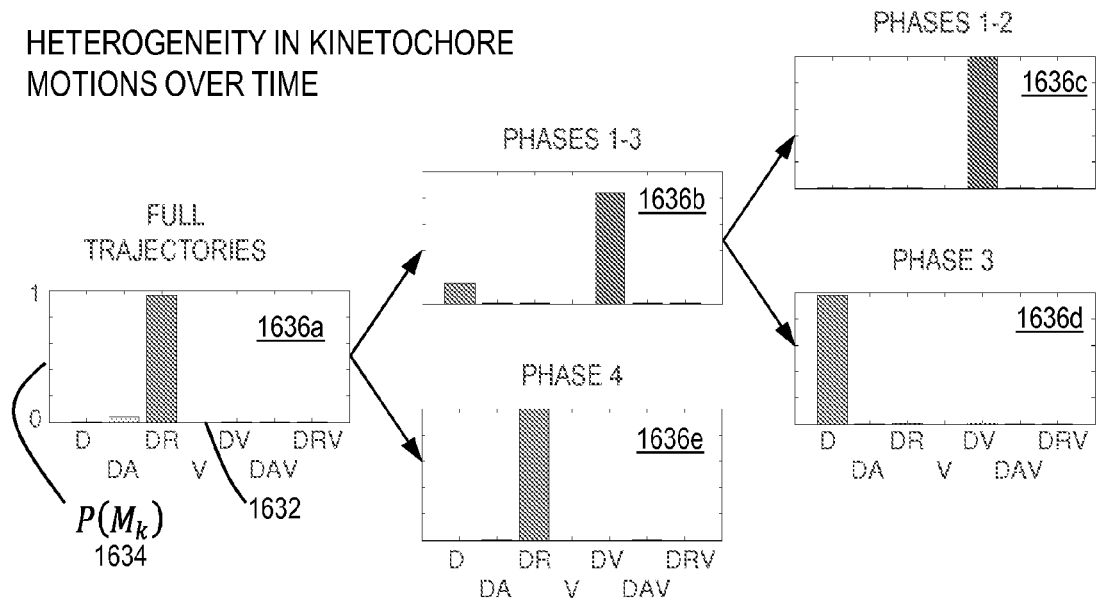

As with the starfish chromosome trajectories, the mean MSD curve calculated over all of the kinetochore trajectories and over the whole period of meiosis was analyzed. FIG. 16C and FIG. 16D are graphs that illustrate an example effect of heterogeneity on analysis of kinetochore MSD data, according to an embodiment. FIG. 16C is a graph 1620 that illustrates example MSD cures for kinetochores, according to an embodiment. The horizontal axis 1622 indicates the time lag in minutes (1 minute=60 seconds); and vertical axis 1624 indicates the MSD in microns squared. Trace 1626a indicates the standard deviation of all the individual MSD curves, and trace 1626b indicates the mean MSD curve and its standard error.

FIG. 16D is a graph that illustrates an example stack of graphs 1636a, 1636b, 1636c, 1636d and 1636e that illustrate example model probabilities for all MSD curves, and for subsets of the MSD. The horizontal axis 1632 indicates a model of the seven models D, DA, DR, V, DV, DAV, DRV. The vertical axis 1634 for each graph indicates $P(M_k)$ given the data. As can be seen, combining all MSD curves is shown in graph 1636a to favor the confined diffusion model DR. Separating phase 4 from the other three phases is shown in graph 1636e to also favor the confined diffusion model DR. The phase 1 through phase 3 MSD curves are shown in graph 1636b to favor the combined diffusion and flow model DV with some noticeable probability of the simple diffusion model. Separating phase 3 from the remaining two phases is shown in graph 1636d to favor the simple diffusion model D. The phase 1 through phase 2 MSD curves are shown in graph 1636c to favor the combined diffusion and flow model DV.

Thus, it was found that the mean behavior of the kinetochores was best explained by a confined diffusion (DR) model, likely due to limitations on their motion due to attachment to microtubules. When the kinetochore trajectories were split along the time axis into two sub-groups, it was found that the confinement behavior could be localized to a single late time phase, corresponding to phase 4, while the diffusion plus flow model was preferred for the earlier portion of the trajectories. This earlier portion of the trajectories was split again, finding that directed motion could be resolved in a portion of the trajectories corresponding to phases 1 and 2, but that phase 3 of the trajectories was best explained by pure diffusion. The magnitude of v for the diffusion plus flow model was 50% larger during phase 1 than phase 2 (0.096 vs. 0.066 μm/min).

Thus, the presented approach justifies the classification into the phases defined in the art. Our results indicate that the kinetochores undergo directed transport during phases 1 and 2, as the chromosomes move from their original positions to form first a spherical shell and then an equatorial prometaphase belt, but that their reorganization into a metaphase plate during phase 3 is dominated by diffusion. These results of the presented approach are consistent with the previous observations and provide additional information about the nature of the directed motions observed during the different phases of meiosis.

4.2.4 CD36 MSD Data

CD36 receptor trajectories in the membranes of macrophages exhibit a range of behaviors including linear motion, confined diffusion, and unconfined diffusion. Accordingly, we sought to test the full range of motion models for the individual receptor trajectories using the presented approach.

Figure 17A:
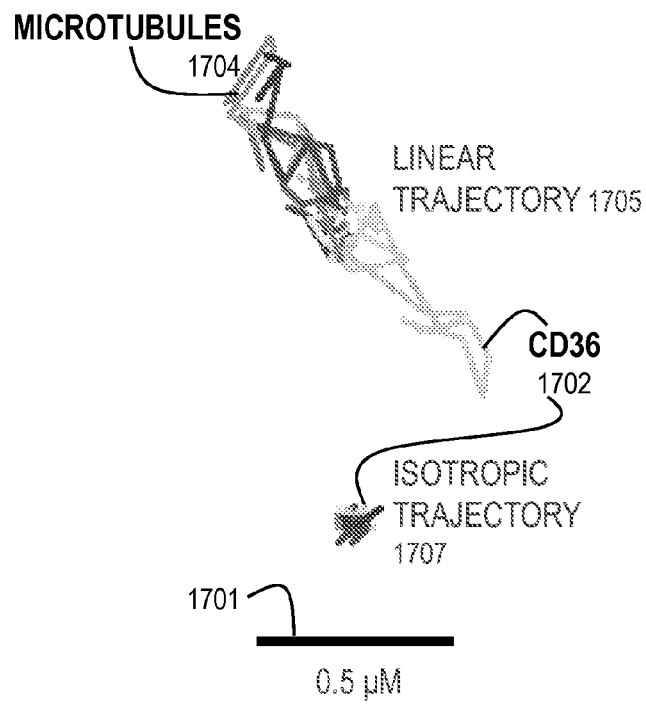
FIG. 17A is a diagram that illustrates example CD36 trajectory data in macrophages, according to an embodiment.
Figure 17B:
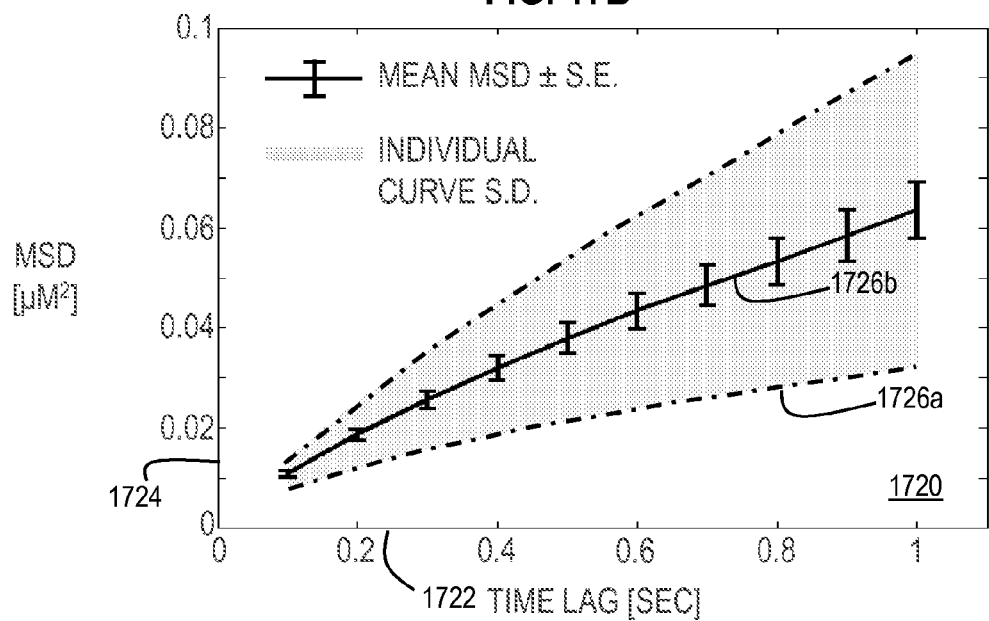
FIG. 17B and FIG. 17C are graphs that illustrate an example effect of heterogeneity on analysis of CD36 MSD data in macrophages, according to an embodiment.
Figure 17C:
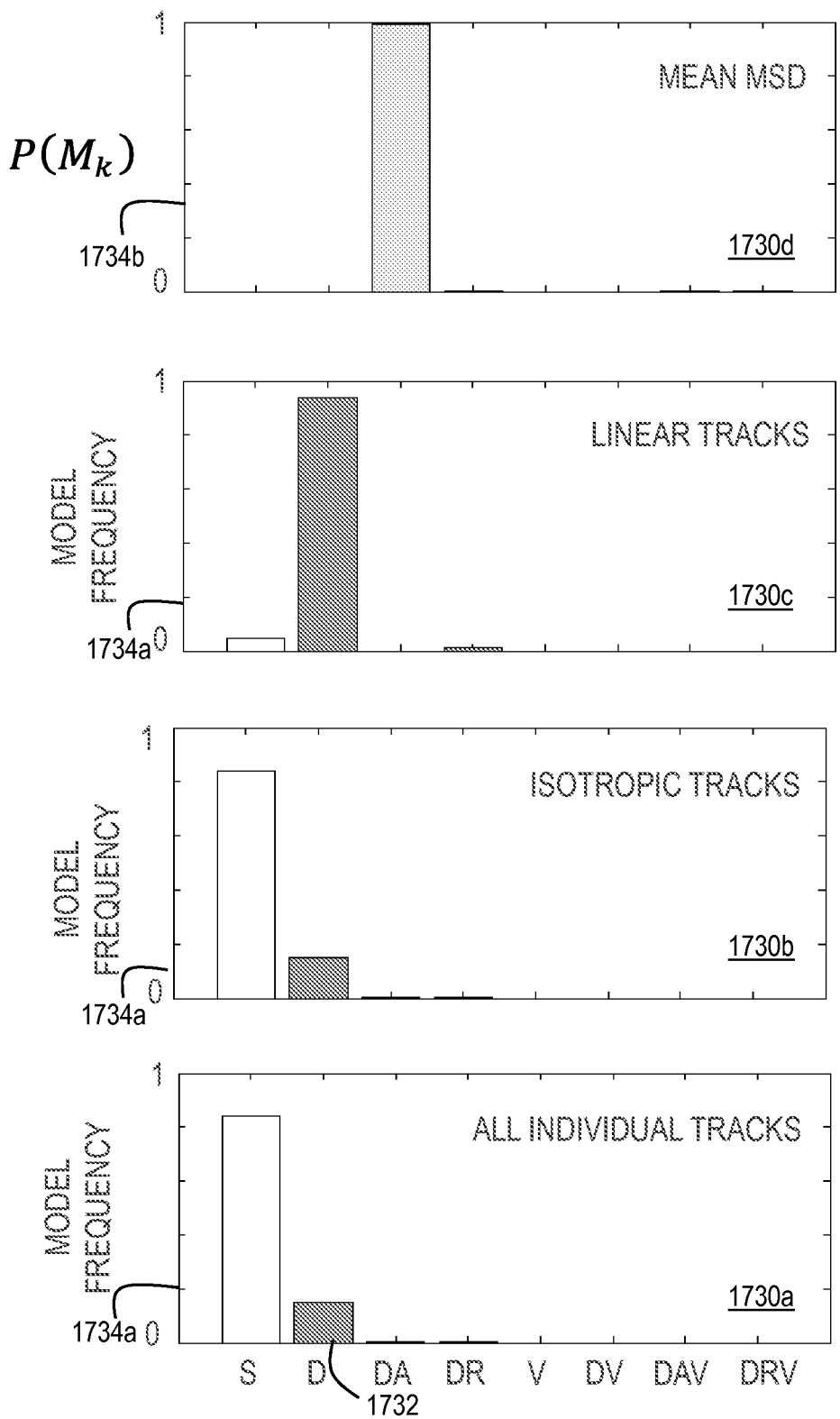

FIG. 17A is a diagram that illustrates example CD36 trajectory data in macrophages, according to an embodiment. The distance of 0.5 microns is indicated by scale bar 1701. Both a linear trajectory 1705 and an isotropic trajectory 1707 includes CD36 1702. microtubules 1704 are included in the linear trajectory, at least. FIG. 17B and FIG. 17C are graphs that illustrate an example effect of heterogeneity on analysis of CD36 MSD data in macrophages, according to an embodiment.

FIG. 17B is a graph 1720 that illustrates example MSD curves for CD36 trajectories, according to an embodiment. The horizontal axis 1722 indicates time lag in seconds; and, the vertical axis 1724 indicates MSD in microns squared. Trace 1726a indicates the standard deviation of all the individual MSD curves around the mean value indicated by trace 1726b with error bars indicating the standard error of the mean value.

FIG. 17C is a stack of graphs 1730a, 1730b, 1730c and 1730d that illustrate example model probabilities based on the MSD curves for CD36, according to an embodiment. The horizontal axis 1732 indicates each of the seven candidate models of FIG. 1D along with a model S for stationary particles. The vertical axis 1734a indicates model frequency for models determined separately from MSD for individual trajectories; and vertical axis 1734b indicates P($M_k$), model probability given the data. Graph 1730d indicates the model probability when grouping all the MSD curves, and strongly favors anomalous diffusion model DA. Graph 1730c indicates the frequency with which each model is favored when using just the linear trajectories individually; and shows the linear trajectories strongly favor simple diffusion model D. Graph 1730b indicates the frequency with which each model is favored when using just the isotropic trajectories individually; and, strongly favors a stationary model with noticeable occurrences of a simple diffusion model D. Graph 1730a indicates the frequency with which each model is favored when all tracks are considered individually, and strongly favors a stationary model with a noticeably number of occurrences of the simple diffusion model.

It was found that while the mean MSD curve was fit best by a model of anomalous diffusion, the individual trajectories were best explained by either a pure diffusion model or a constant (stationary) model. The latter model represents stationary particles that are either fixed in place or confined within a confinement zone smaller than the localization error in the particle position measurements during tracking, and is given by $MSD_S(\tau)=4\sigma^2$ in the case of two-dimensional trajectories, where σ is the localization error of the particle. This model should therefore be included when localization error is expected to make a significant contribution to the MSD values. The trajectories were also split into linear vs. isotropic motion types as previously described by others; and the motion models preferred for each type of trajectory were examined. The pure diffusion model was preferred for nearly all of the linear trajectories confirming that these motions are linear due to 1D diffusion (for example, diffusion along 1D tracks or within linear-shaped confinement zones) rather than to directed motion. The stationary model was preferred for most of the isotropic trajectories, indicating that these receptors are tightly confined. Only a small fraction of receptors exhibited isotropic unconfined diffusion. These results are consistent with those in the art; and demonstrate the applicability of the presented approach to the analysis of trajectories from a very different system, in this case, 2D motion in cell membranes.

Single-particle tracking is a powerful approach to quantitative analysis of biological systems. Mechanistic interpretation of the origin of single-particle trajectories that are governed by complex biological processes, including secondary interactions with membranes, cytoskeletal structures, and other proteins, requires a method for systematic and unbiased analysis of SPTs. Bayesian inference provides a convenient framework for the systematic evaluation of competing hypotheses for particle motion in the presence of data limitations including sampling rate and trajectory length, as well as sample heterogeneity. Advantages of the approach as presented here are that it is generally applicable to any model of motion for which an analytical form for the MSD curve is known and that it builds on the MSD approach that is already widespread in particle trajectory analysis. Application of this approach to several disparate biological datasets demonstrates the range of applicability of the proposed procedure, including determination of the origin of sample heterogeneity via classification and repeated hypothesis testing. In all cases, the presented procedure successfully prefers simpler models when high noise and variability preclude the resolution of more complex and detailed models of motion that are not justified by the data. We anticipate that incorporation of the present procedure into automated cell analysis programs such as Cell Profiler will bring systematic evaluation of SPTs to high-content screens for the analysis of live-cell data under wild type and perturbed conditions. The procedure will also be available as an online resource, which will aid in the collection and analysis of experimental particle trajectory datasets from a variety of biological sources. Although this section focused on MSD curves, variations on this presented approach are applicable to other metrics derived from single particle trajectories, including other moments or single step analyses.

5. Hardware Overview

Figure 18:
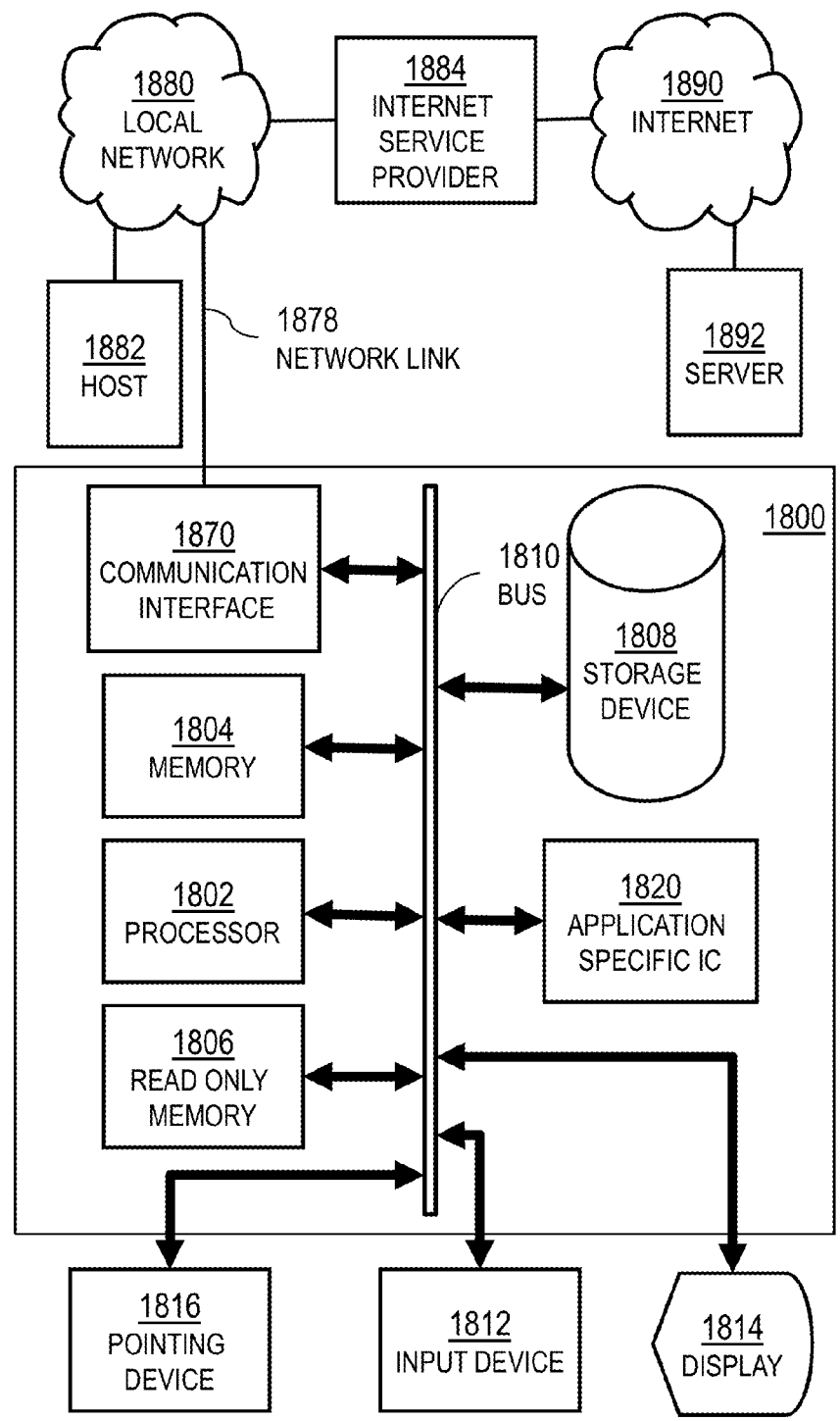
FIG. 18 is a block diagram that illustrates a computer system upon which an embodiment of the invention may be implemented.

FIG. 18 is a block diagram that illustrates a computer system 1800 upon which an embodiment of the invention may be implemented. Computer system 1800 includes a communication mechanism such as a bus 1810 for passing information between other internal and external components of the computer system 1800. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit)). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1800, or a portion thereof, constitutes a means for performing one or more steps of one or more methods described herein.

A sequence of binary digits constitutes digital data that is used to represent a number or code for a character. A bus 1810 includes many parallel conductors of information so that information is transferred quickly among devices coupled to the bus 1810. One or more processors 1802 for processing information are coupled with the bus 1810. A processor 1802 performs a set of operations on information. The set of operations include bringing information in from the bus 1810 and placing information on the bus 1810. The set of operations also typically include comparing two or more units of information, shifting positions of units of information, and combining two or more units of information, such as by addition or multiplication. A sequence of operations to be executed by the processor 1802 constitute computer instructions.

Computer system 1800 also includes a memory 1804 coupled to bus 1810. The memory 1804, such as a random access memory (RAM) or other dynamic storage device, stores information including computer instructions. Dynamic memory allows information stored therein to be changed by the computer system 1800. RAM allows a unit of information stored at a location called a memory address to be stored and retrieved independently of information at neighboring addresses. The memory 1804 is also used by the processor 1802 to store temporary values during execution of computer instructions. The computer system 1800 also includes a read only memory (ROM) 1806 or other static storage device coupled to the bus 1810 for storing static information, including instructions, that is not changed by the computer system 1800. Also coupled to bus 1810 is a non-volatile (persistent) storage device 1808, such as a magnetic disk or optical disk, for storing information, including instructions, that persists even when the computer system 1800 is turned off or otherwise loses power.

Information, including instructions, is provided to the bus 1810 for use by the processor from an external input device 1812, such as a keyboard containing alphanumeric keys operated by a human user, or a sensor. A sensor detects conditions in its vicinity and transforms those detections into signals compatible with the signals used to represent information in computer system 1800. Other external devices coupled to bus 1810, used primarily for interacting with humans, include a display device 1814, such as a cathode ray tube (CRT) or a liquid crystal display (LCD), for presenting images, and a pointing device 1816, such as a mouse or a trackball or cursor direction keys, for controlling a position of a small cursor image presented on the display 1814 and issuing commands associated with graphical elements presented on the display 1814.

In the illustrated embodiment, special purpose hardware, such as an application specific integrated circuit (IC) 1820, is coupled to bus 1810. The special purpose hardware is configured to perform operations not performed by processor 1802 quickly enough for special purposes. Examples of application specific ICs include graphics accelerator cards for generating images for display 1814, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1800 also includes one or more instances of a communications interface 1870 coupled to bus 1810. Communication interface 1870 provides a two-way communication coupling to a variety of external devices that operate with their own processors, such as printers, scanners and external disks. In general the coupling is with a network link 1878 that is connected to a local network 1880 to which a variety of external devices with their own processors are connected. For example, communication interface 1870 may be a parallel port or a serial port or a universal serial bus (USB) port on a personal computer. In some embodiments, communications interface 1870 is an integrated services digital network (ISDN) card or a digital subscriber line (DSL) card or a telephone modem that provides an information communication connection to a corresponding type of telephone line. In some embodiments, a communication interface 1870 is a cable modem that converts signals on bus 1810 into signals for a communication connection over a coaxial cable or into optical signals for a communication connection over a fiber optic cable. As another example, communications interface 1870 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1870 sends and receives electrical, acoustic or electromagnetic signals, including infrared and optical signals, that carry information streams, such as digital data.

The term computer-readable medium is used herein to refer to any medium that participates in providing information to processor 1802, including instructions for execution. Such a medium may take many forms, including, but not limited to, non-volatile media, volatile media and transmission media. Non-volatile media include, for example, optical or magnetic disks, such as storage device 1808. Volatile media include, for example, dynamic memory 1804. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1802, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1802, except for carrier waves and other signals.

Logic encoded in one or more tangible media includes one or both of processor instructions on a computer-readable storage media and special purpose hardware, such as ASIC 1820.

Network link 1878 typically provides information communication through one or more networks to other devices that use or process the information. For example, network link 1878 may provide a connection through local network 1880 to a host computer 1882 or to equipment 1884 operated by an Internet Service Provider (ISP). ISP equipment 1884 in turn provides data communication services through the public, world-wide packet-switching communication network of networks now commonly referred to as the Internet 1890. A computer called a server 1892 connected to the Internet provides a service in response to information received over the Internet. For example, server 1892 provides information representing video data for presentation at display 1814.

The invention is related to the use of computer system 1800 for implementing the techniques described herein. According to one embodiment of the invention, those techniques are performed by computer system 1800 in response to processor 1802 executing one or more sequences of one or more instructions contained in memory 1804. Such instructions, also called software and program code, may be read into memory 1804 from another computer-readable medium such as storage device 1808. Execution of the sequences of instructions contained in memory 1804 causes processor 1802 to perform the method steps described herein. In alternative embodiments, hardware, such as application specific integrated circuit 1820, may be used in place of or in combination with software to implement the invention. Thus, embodiments of the invention are not limited to any specific combination of hardware and software.

The signals transmitted over network link 1878 and other networks through communications interface 1870, carry information to and from computer system 1800. Computer system 1800 can send and receive information, including program code, through the networks 1880, 1890 among others, through network link 1878 and communications interface 1870. In an example using the Internet 1890, a server 1892 transmits program code for a particular application, requested by a message sent from computer 1800, through Internet 1890, ISP equipment 1884, local network 1880 and communications interface 1870. The received code may be executed by processor 1802 as it is received, or may be stored in storage device 1808 or other non-volatile storage for later execution, or both. In this manner, computer system 1800 may obtain application program code in the form of a signal on a carrier wave.

Various forms of computer readable media may be involved in carrying one or more sequence of instructions or data or both to processor 1802 for execution. For example, instructions and data may initially be carried on a magnetic disk of a remote computer such as host 1882. The remote computer loads the instructions and data into its dynamic memory and sends the instructions and data over a telephone line using a modem. A modem local to the computer system 1800 receives the instructions and data on a telephone line and uses an infra-red transmitter to convert the instructions and data to a signal on an infra-red a carrier wave serving as the network link 1878. An infrared detector serving as communications interface 1870 receives the instructions and data carried in the infrared signal and places information representing the instructions and data onto bus 1810. Bus 1810 carries the information to memory 1804 from which processor 1802 retrieves and executes the instructions using some of the data sent with the instructions. The instructions and data received in memory 1804 may optionally be stored on storage device 1808, either before or after execution by the processor 1802.

Figure 19:
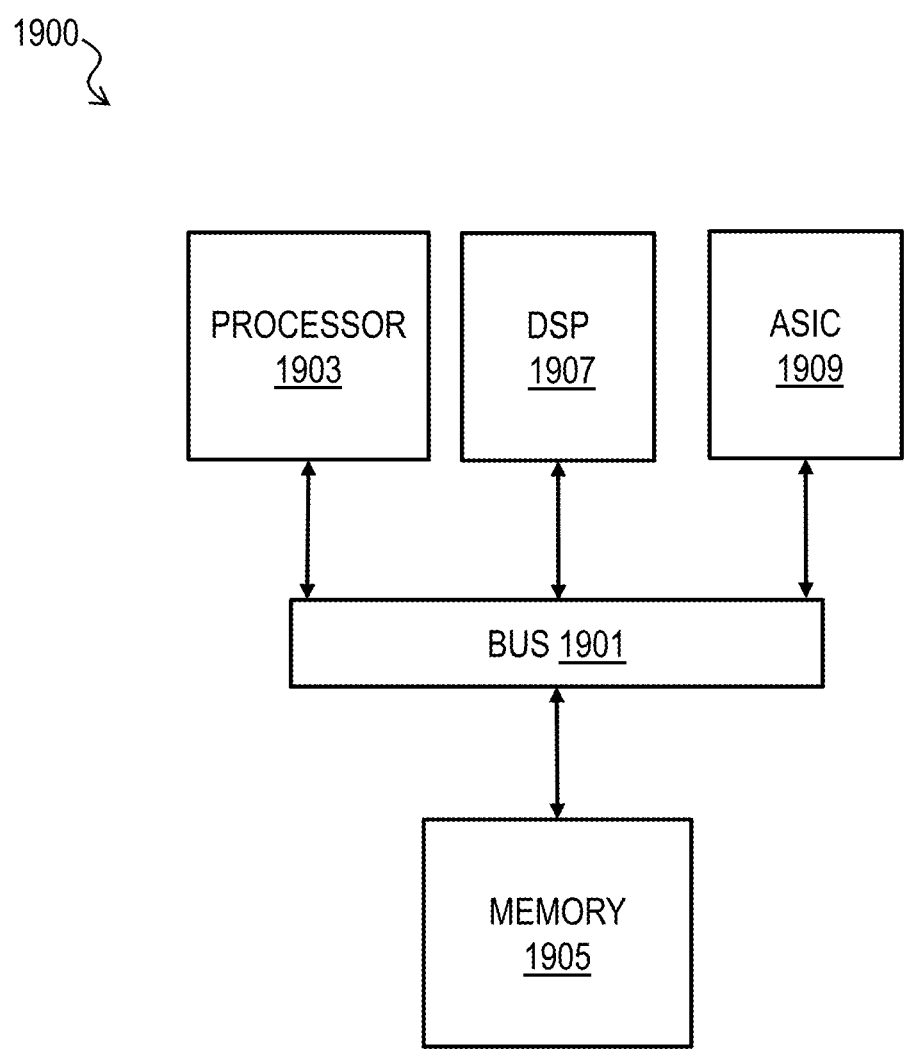
FIG. 19 illustrates a chip set upon which an embodiment of the invention may be implemented.

FIG. 19 illustrates a chip set 1900 upon which an embodiment of the invention may be implemented. Chip set 1900 is programmed to perform one or more steps of a method described herein and includes, for instance, the processor and memory components described with respect to FIG. 18 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1900, or a portion thereof, constitutes a means for performing one or more steps of a method described herein.

In one embodiment, the chip set 1900 includes a communication mechanism such as a bus 1901 for passing information among the components of the chip set 1900. A processor 1903 has connectivity to the bus 1901 to execute instructions and process information stored in, for example, a memory 1905. The processor 1903 may include one or more processing cores with each core configured to perform independently. A multi-core processor enables multiprocessing within a single physical package. Examples of a multi-core processor include two, four, eight, or greater numbers of processing cores. Alternatively or in addition, the processor 1903 may include one or more microprocessors configured in tandem via the bus 1901 to enable independent execution of instructions, pipelining, and multithreading. The processor 1903 may also be accompanied with one or more specialized components to perform certain processing functions and tasks such as one or more digital signal processors (DSP) 1907, or one or more application-specific integrated circuits (ASIC) 1909. A DSP 1907 typically is configured to process real-world signals (e.g., sound) in real time independently of the processor 1903. Similarly, an ASIC 1909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1903 and accompanying components have connectivity to the memory 1905 via the bus 1901. The memory 1905 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1905 also stores the data associated with or generated by the execution of one or more steps of the methods described herein.

6. Extensions and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

What is claimed is:

1. A method comprising:
    determining a plurality of models for motion of particles in a biological sample, each model including a corresponding set of one or more parameters;
    obtaining measured data based on measurements at one or more voxels of an imaging system sensitive to motion of particles in the biological sample;
    determining, at least in part on a first hardware processor, noise correlation of the measured data;
    determining, at least in part on a second hardware processor, based at least in part on the noise correlation, a marginal likelihood of the measured data for each model of the plurality of models;
    determining a relative probability for each model of the plurality of models based on the marginal likelihood; and
    determining, based at least in part on the relative probability for each model, a value for a parameter of the set of one or more parameters corresponding to a selected model of the plurality of models.

2. A method as recited in claim 1, wherein determining noise correlation of the measured data further comprises determining a covariance matrix of the measured data.

3. A method as recited in claim 2, wherein determining the noise correlation further comprises regularizing the covariance matrix of the measured data using a shrinkage estimator.

4. A method as recited in claim 1, wherein determining the marginal likelihood of the measured data for each model further comprises determining, based on the noise correlation, a multivariate Gaussian function that describes probability $P(y|\beta, M)$ of the measured data y given a set of values $\beta$ for the set of one or more parameters corresponding to each model M.

5. A method as recited in claim 4, wherein determining the marginal likelihood of the measured data for each model further comprises determining, based on the noise correlation, a posterior probability $P(\beta|y, M)$ for values of a set of one or more parameters corresponding to each model M given the data y using generalized least squares, wherein the posterior probability indicates a most likely set of values $\beta$post and a covariance matrix $\Sigma_\beta$.

6. A method as recited in claim 5, wherein determining the marginal likelihood of the measured data for each model further comprises;
    determining, based on $\beta$post and $\Sigma_\beta$, a prior probability $P(\beta|M)$ for values of a set of one or more parameters corresponding to each model; and
    determining the marginal likelihood $P(y|M)$ of the measured data y for each model M by performing Monte Carlo integration, over a range of particular parameter values for the set of one or more parameters, of a product of a probability $P(y|\beta, M)$ of the measured data for one set of particular parameter values for the set of one or more parameters corresponding to each model and a prior probability $P(\beta|M)$ of the one set of particular parameter value for each model.

7. A method as recited in claim 5, wherein determining the marginal likelihood of the measured data for each model further comprises;
    determining that the posterior probability $P(\beta|y, M)$ for a model M approaches a Gaussian distribution; and
    determining the marginal likelihood $P(y|M)$ of the measured data y for each model M by evaluating the Laplace approximation based on $\beta$post and $\Sigma_\beta$.

8. A method as recited in claim 6, wherein determining the prior probability $P(\beta|M)$ further determining a constant probability density function normalized to 1.0 in a range centered at $\beta$post and extending to extreme values separated by more than about ten times a standard deviation based on $\Sigma_\beta$.

9. A method as recited in claim 6, further comprising determining the prior probability of a parameter of a model by determining equal probability per decade for the parameter normalized to 1.0 in a range centered at $\beta$post and extending to extreme values separated by more than about ten times a standard deviation based on $\Sigma_\beta$.

10. A method as recited in claim 1, wherein the selected model is the one most likely model.

11. A method as recited in claim 1, wherein determining the value for the parameter further comprises determining an average of values of the parameter over all models wherein each value is weighted by the relative probability for each model.

12. A method as recited in claim 1, wherein determining the value for the parameter of the set of one or more parameters corresponding to the selected model further comprises selecting the model based on a ratio of the relative probability for any two models of the plurality of models exceeding a threshold of about 10.

13. A method as recited in claim 1, wherein the measured data is fluorescence correlation spectroscopy (FCS) data comprising one or more temporal autocorrelation function (TACF) curves based on measurements of fluorescence intensity time series at one or more voxels of a confocal microscope fluorescence measurement system.

14. A method as recited in claim 13, wherein determining the noise level and the noise correlation of the measured data further comprises determining a covariance matrix for a plurality of TACF curves.

15. A method as recited in claim 14, wherein,
    obtaining measured data further comprises determining a mean TACF curve from the plurality of TACF curves; and
    determining the noise level and the noise correlation of the measured data further comprises determining the noise level and the noise correlation for the mean TACF curve based on the covariance matrix for the plurality of TACF curves divided by a number of members in the plurality of TACF curves.

16. A method as recited in claim 13, wherein determining the noise level and the noise correlation of the measured data further comprises determining the noise level and the noise correlation of a single fluorescence intensity time series by determining a covariance matrix for deviations of individual time-lagged intensity products from a mean of time-lagged intensity products over a duration of the single fluorescence intensity time series.

17. A method as recited in claim 16, wherein determining the noise level and the noise correlation of a single fluorescence intensity time series further comprises performing a block transform on the individual time-lagged intensity products to yield independent samples of the individual time-lagged intensity products before determining the covariance matrix.

18. A method as recited in claim 1, wherein the measured data is mean square displacement (MSD) data based on one or more single particle trajectories (SPT) that each indicate voxel positions in the imaging system where an individual particle is detected as a function of time.

19. A method as recited in claim 18, wherein the measured data is a mean MSD curve based on a plurality of SPT from different particles undergoing the same physical process or from sub-trajectories of a single particle trajectory or both.

20. A method as recited in claim 18, wherein determining the noise correlation of the measured data further comprises determining a covariance matrix for the MSD data.

21. A method as recited in claim 18, wherein.
  obtaining measured data further comprises determining a mean MSD curve from a plurality of MSD curves; and
  determining the noise correlation of the measured data further comprises determining the noise correlation for the mean MSD curve based on the covariance matrix for the plurality of MSD curves divided by a number of members in the plurality of MSD curves.

22. A non-transient computer-readable medium carrying one or more sequences of instructions, wherein execution of the one or more sequences of instructions by one or more processors causes an apparatus to perform at least the following:
  determine a plurality of models for motion of particles in a biological sample, each model including a corresponding set of one or more parameters;
  obtain measured data based on measurements at one or more voxels of an imaging system sensitive to motion of particles in the biological sample;
  determine noise correlation of the measured data;
  determine, based at least in part on the noise correlation, a marginal likelihood of the measured data for each model of the plurality of models;
  determine a relative probability for each model of the plurality of models based on the marginal likelihood; and
  determine, based at least in part on the relative probability for each model, a value for a parameter of the set of one or more parameters corresponding to a selected model of the plurality of models.

23. An apparatus comprising:
  at least one processor; and
  at least one memory including one or more sequences of instructions,
  the at least one memory and the one or more sequences of instructions configured to, with the at least one processor, cause the apparatus to perform at least the following,
    determine a plurality of models for motion of particles in a biological sample, each model including a corresponding set of one or more parameters;
    obtain measured data based on measurements at one or more voxels of an imaging system sensitive to motion of particles in the biological sample;
    determine noise correlation of the measured data;
    determine, based at least in part on the noise correlation, a marginal likelihood of the measured data for each model of the plurality of models;
    determine a relative probability for each model of the plurality of models based on the marginal likelihood; and
    determine, based at least in part on the relative probability for each model, a value for a parameter of the set of one or more parameters corresponding to a selected model of the plurality of models.

* * * * *